(12) United States Patent
Zhao et al.

(10) Patent No.: US 8,147,503 B2
(45) Date of Patent: Apr. 3, 2012

(54) METHODS OF LOCATING AND TRACKING ROBOTIC INSTRUMENTS IN ROBOTIC SURGICAL SYSTEMS

(75) Inventors: Wenyi Zhao, Mountain View, CA (US); Christopher J. Hasser, Los Altos, CA (US); William C. Nowlin, Los Altos, CA (US); Brian D. Hoffman, Sunnyvale, CA (US)

(73) Assignee: Intuitive Surgical Operations Inc., Sunnyvale, CA (US)

( * ) Notice: Subject to any disclaimer, the term of this patent is extended or adjusted under 35 U.S.C. 154(b) by 1220 days.

(21) Appl. No.: 11/865,015

(22) Filed: Sep. 30, 2007

(65) Prior Publication Data
US 2009/0088773 A1    Apr. 2, 2009

(51) Int. Cl.
*A61B 17/00*    (2006.01)
(52) U.S. Cl. ........ 606/130; 600/424; 600/427; 600/437; 700/245; 382/128; 382/131; 382/132
(58) Field of Classification Search .................. 600/407, 600/424, 427, 437; 606/130; 700/245
See application file for complete search history.

(56) References Cited

U.S. PATENT DOCUMENTS

| | | | |
|---|---|---|---|
| 4,753,569 A | 6/1988 | Pryor | |
| 4,754,415 A | 6/1988 | George et al. | |
| 4,826,391 A | 5/1989 | Lawrence et al. | |
| 5,047,701 A | 9/1991 | Takarada et al. | |
| 5,078,140 A | 1/1992 | Kwoh | |
| 5,086,401 A | 2/1992 | Glassman et al. | |
| 5,388,059 A | 2/1995 | DeMenthon | |
| 5,487,172 A * | 1/1996 | Hyatt | ............................... 712/32 |
| 5,572,999 A | 11/1996 | Funda et al. | |
| 5,579,444 A | 11/1996 | Dalziel et al. | |
| 5,630,431 A | 5/1997 | Taylor | |
| 5,649,021 A | 7/1997 | Matey et al. | |
| 5,797,849 A | 8/1998 | Vesely et al. | |
| 5,820,545 A | 10/1998 | Arbter et al. | |
| 5,950,201 A * | 9/1999 | Van Huben et al. | .................. 1/1 |
| 5,959,425 A | 9/1999 | Bieman et al. | |
| 6,036,637 A | 3/2000 | Kudo | |
| 6,106,511 A | 8/2000 | Jensen | |
| 6,167,296 A | 12/2000 | Shahidi | |
| 6,231,526 B1 | 5/2001 | Taylor et al. | |
| 6,235,038 B1 | 5/2001 | Hunter et al. | |

(Continued)

FOREIGN PATENT DOCUMENTS

EP        1854425        11/2007

(Continued)

OTHER PUBLICATIONS

PCT/US08/77611 Invitation to Pay Additional Fees with Results of the Partial International Search, mailed Feb. 24, 2009, 5 pages.

(Continued)

*Primary Examiner* — David A Vanore

(57) ABSTRACT

In one embodiment of the invention, a method is disclosed to locate a robotic instrument in the field of view of a camera. The method includes capturing sequential images in a field of view of a camera. The sequential images are correlated between successive views. The method further includes receiving a kinematic datum to provide an approximate location of the robotic instrument and then analyzing the sequential images in response to the approximate location of the robotic instrument. An additional method for robotic systems is disclosed. Further disclosed is a method for indicating tool entrance into the field of view of a camera.

25 Claims, 29 Drawing Sheets

U.S. PATENT DOCUMENTS

| | | | |
|---|---|---|---|
| 6,278,906 B1 | 8/2001 | Piepmeier et al. | |
| 6,292,715 B1* | 9/2001 | Rongo | 700/249 |
| 6,346,072 B1 | 2/2002 | Cooper | |
| 6,425,865 B1 | 7/2002 | Salcudean et al. | |
| 6,434,416 B1 | 8/2002 | Mizoguchi et al. | |
| 6,459,926 B1 | 10/2002 | Nowlin et al. | |
| 6,468,265 B1 | 10/2002 | Evans et al. | |
| 6,470,207 B1 | 10/2002 | Simon et al. | |
| 6,490,475 B1 | 12/2002 | Seeley et al. | |
| 6,529,765 B1 | 3/2003 | Franck et al. | |
| 6,533,737 B1 | 3/2003 | Brosseau et al. | |
| 6,587,750 B2 | 7/2003 | Gerbi et al. | |
| 6,591,130 B2 | 7/2003 | Shahidi | |
| 6,665,554 B1 | 12/2003 | Charles et al. | |
| 6,668,677 B2* | 12/2003 | Knappe et al. | 74/490.01 |
| 6,671,581 B2 | 12/2003 | Niemeyer et al. | |
| 6,690,963 B2 | 2/2004 | Ben-Haim et al. | |
| 6,725,080 B2 | 4/2004 | Melkent et al. | |
| 6,741,911 B2* | 5/2004 | Simmons | 700/245 |
| 6,770,081 B1 | 8/2004 | Cooper et al. | |
| 6,782,287 B2 | 8/2004 | Grzeszczuk et al. | |
| 6,785,593 B2* | 8/2004 | Wang et al. | 700/258 |
| 6,799,065 B1 | 9/2004 | Niemeyer | |
| 6,799,088 B2* | 9/2004 | Wang et al. | 700/258 |
| 6,804,581 B2* | 10/2004 | Wang et al. | 700/251 |
| 6,816,755 B2 | 11/2004 | Habibi et al. | |
| 6,858,003 B2 | 2/2005 | Evans et al. | |
| 6,871,117 B2* | 3/2005 | Wang et al. | 700/245 |
| 6,951,535 B2* | 10/2005 | Ghodoussi et al. | 600/101 |
| 6,978,167 B2 | 12/2005 | Dekel et al. | |
| 7,008,373 B2 | 3/2006 | Stoianovici et al. | |
| 7,074,179 B2* | 7/2006 | Wang et al. | 600/101 |
| 7,155,316 B2 | 12/2006 | Sutherland et al. | |
| 7,162,338 B2 | 1/2007 | Goncalves et al. | |
| 7,272,467 B2 | 9/2007 | Goncalves et al. | |
| 7,283,654 B2 | 10/2007 | McLain | |
| 7,359,746 B2 | 4/2008 | Arata | |
| 7,413,565 B2* | 8/2008 | Wang et al. | 606/1 |
| 7,453,227 B2 | 11/2008 | Prisco et al. | |
| 7,458,936 B2* | 12/2008 | Zhou et al. | 600/437 |
| 7,464,596 B2* | 12/2008 | Bui et al. | 73/618 |
| 7,545,965 B2* | 6/2009 | Suzuki et al. | 382/128 |
| 7,571,025 B2 | 8/2009 | Bischoff | |
| 7,612,805 B2* | 11/2009 | Solomon | 348/222.1 |
| 7,664,571 B2 | 2/2010 | Gonzalez-Banos et al. | |
| 7,689,321 B2 | 3/2010 | Karlsson | |
| 2003/0055410 A1 | 3/2003 | Evans et al. | |
| 2003/0210812 A1 | 11/2003 | Khamene et al. | |
| 2005/0102063 A1* | 5/2005 | Bierre | 700/247 |
| 2005/0234679 A1 | 10/2005 | Karlsson | |
| 2006/0058919 A1 | 3/2006 | Sommer | |
| 2006/0258938 A1 | 11/2006 | Hoffman et al. | |
| 2007/0265527 A1 | 11/2007 | Wohlgemuth | |
| 2008/0255445 A1 | 10/2008 | Neubauer et al. | |
| 2009/0037278 A1* | 2/2009 | Cohen et al. | 705/14 |
| 2009/0088634 A1* | 4/2009 | Zhao et al. | 600/427 |
| 2009/0088897 A1* | 4/2009 | Zhao et al. | 700/250 |
| 2009/0324009 A1 | 12/2009 | Schulz | |

FOREIGN PATENT DOCUMENTS

| | | |
|---|---|---|
| EP | 1886640 | 2/2008 |
| WO | WO-0057767 A3 | 1/2001 |

OTHER PUBLICATIONS

Loy, Gareth et al., "An Adaptive Fusion Architecture for Target Tracking," Proceedings of the 5th IEEE International Conference on Automatic Face and Gesture Recognition (FGR'02), May 20-21, 2002, Washington, D.C., 6 pages.

Lee, M.F. Ricky et al., "Implementation of Sensor Selection and Fusion Using Fuzzy Logic," Joint 9th IFSA World Congress and 20th NAFIPS International Conference, Jul. 25-28, 2001, Vancouver, BC. Canada, vol. 1, pp. 328-333.

Luo, Ren C. and Min-Hsiung Lin, "Robot Multi-Sensor Fusion and Integration: Optimum Estimation of Fused Sensor Data," Proceedings of 1988 IEEE International Conference on Robotics and Automation, Apr. 24-29, 1988, Philadelphia, PA, vol. 2, pp. 1076-1081.

Nakamura, Yoshihiko and Yingti Xu, "Geometrical Fusion Method for Multi-Sensor Robotic Systems," Proceedings of the 1989 IEEE International Conference on Robotics and Automation, May 14-19, 1989, Scottsdale, AZ, vol. 2, pp. 668-673.

Oh, Paul Y. and Peter K. Allen, "Visual Servoing by Partitioning Degrees of Freedom," IEEE Transactions on Robotics and Automation, Feb. 2001, vol. 17, No. 1, pp. 1-17

Office Action for U.S. Appl. No. 11/865,016, mailed Dec. 23, 2010, 9 pages.

Casals, A. et al., "Automatic Guidance of an Assistant Robot in Laparoscopic Surgery," 1996 IEEE International Conference on Robotics and Automation (ICRA '96), Minneapolis, MN, Apr. 1996, pp. 895-900.

Corke, Peter I., "Visual Control of Robot Manipulators—A Review," Visual Servoing: Real-Time Control of Robot Manipulators Based on Visual Sensory Feedback, vol. 7 of Series in Robotics and Automated Systems, Ed. Koichi Hashimoto, World Scientific Publishing Ltd., London, 1993, pp. 1-31.

U.S. Appl. No. 11/865,014, Zhao, Wenyi et al.

U.S. Appl. No. 11/865,016, Zhao, Wenyi et al.

Delamarre, Quentin and Olivier Faugeras, "3D Articulated Models and Multi-Tracking with Silhouettes," 7th IEEE International Conference on Computer Vision, Sep. 20-27, 1999, vol. 2, pp. 716-721.

Doignon, C. et al., "Model-based 3-D pose estimation and feature tracking for robot assisted surgery with medical imaging," published in "From Features to Actions: Unifying Perspectives in Computational and Robot Vision," 2007, 10 pages. Internet: http://hal.archives-ouvertes.fr/docs/00/35/06/47/PDF/2007_wkicra_doignon.pdf.

Drummond T. et al., "Real-time tracking of highly articulated structures in the presence of noisy measurements," Proc. Int'l Conf. Computer Vision, 2001, pp. 315-320, IEEE.

Drummond, Tom and Roberto Cipolla, "Real-Time Visual Tracking of Complex Structures," IEEE Transactions on Pattern Analysis and Machine Intelligence (PAMI), Jul. 2002, vol. 24, No. 7, pp. 932-946.

Green, Philip S. et al., "Telepresence Surgery," IEEE Engineering in Medicine and Biology Magazine, May/Jun. 1995, pp. 324-329, vol. 14—Issue 3, IEEE.

Grimson, W.E.L., et al., "An automatic registration method for frameless stereotaxy, image guided surgery, and enhanced reality visualization," IEEE Transactions on Medical Imaging, vol. 15, No. 2, Apr. 1996, pp. 129-140.

Guthart, Gary S. et al., "The IntuitiveTM telesurgery system: overview and application," Proceedings of the 2000 IEEE International Conference on Robotics and Automation, 2000, pp. 618-621, vol. 1, IEEE.

Horn, Berthold K.P., "Closed-form solution of absolute orientation using unit quaternions," Journal of the Optical Society of America A, vol. 4, No. 4, pp. 629-642, Apr. 1987.

Julier, Simon J. and Jeffrey K. Uhlmann, "A New Extension of the Kalman Filter to Nonlinear Systems," The Proceedings of AeroSense: The 11th International Symposium on Aerospace/Defense Sensing, Simulation and Controls, Orlando, FL, USA, 1997. SPIE. Multi Sensor Fusion, Tracking and Resource Management II, vol. 3068, pp. 182-193.

Jung, Soon Ki and Kwang Yun Wohn, "A model-based 3-D tracking of rigid objects from a sequence of multiple perspective views," Pattern Recognition Letters, 1998, vol. 19, pp. 499-512.

Kalman, R.E., "A new approach to linear filtering and prediction problems," Transactions of the American Society of Mechanical Engineers (ASME), Journal of Basic Engineering, vol. 82, Series D, 1960, pp. 35-45.

Liu, Jun S. and Rong Chen, "Sequential Monte Carlo Methods for Dynamic Systems," Journal of the American Statistical Association, 1988, vol. 93, pp. 1032-1044.

Lowe, David G., "Fitting Parameterized Three-Dimensional Models To Images," IEEE Transactions on Pattern Analysis and Machine Intelligence (PAMI), May 1991, vol. 13, Issue 5, pp. 441-450.

Lowe, David G., "Object Recognition from Local Scale-Invariant Features," 7th IEEE International Conference on Computer Vision, Sep. 20-27, 1999, vol. 2, pp. 1150-1157.

Marchand, Eric et al., "Robust real-time visual tracking using a 2D-3D model-based approach," Proc.of the Seventh IEEE International Conference on Computer Vision, 1999, pp. 262-268, vol. 1, IEEE.

Martin, Frederick and Radu Horaud, "Multiple-Camera Tracking of Rigid Objects," International Journal of Robotics Research, Feb. 2002, vol. 21, No. 2, pp. 97-113.

Nitzan, David, "Three-Dimensional Vision Structure for Robot Applications," IEEE Transactions on Pattern Analysis and Machine Intelligence (PAMI), May 1988, vol. 10, No. 3, pp. 291-309.

Papanikolopoulos, N. et al., "Vision and Control Techniques for Robotic Visual Tracking," 1991 IEEE International Conference on Robotics and Automation, Apr. 9-11, 1991, vol. 1, pp. 857-864.

Papanikolopoulos, N. et al., "Visual Tracking of a Moving Target by a Camera Mounted on a Robot: A Combination of Control and Vision," IEEE Transactions on Robotics and Automation, Feb. 1993, vol. 9, No. 1, pp. 14-35.

Plaenkers, Ralf et al., "Model-Based Silhouette Extraction for Accurate People Tracking," Proceedings of the 7th European Conference on Computer Vision-Part II, 2002, pp. 325-339, Springer-Verlag.

Pope, Arthur R. and David G. Lowe, "Learning Appearance Models for Object Recognition," International Workshop on Object Representation in Computer Vision II, 1996, Lecture Notes in Computer Science, vol. 1144, pp. 201-219.

Rasmussen, Christopher et al., "Probabilistic data association methods for tracking complex visual objects," IEEE Transactions on Pattern Analysis and Machine Intelligence, 2001, pp. 560-576, vol. 23, Issue 6, IEEE.

Rehg, James M. and Takeo Kanade, "Model-Based Tracking of Self-Occluding Articulated Objects," 5th International Conference on Computer Vision, Jun. 20-23, 1995. pp. 612-617.

Senior, Andrew, "Real-time articulated human body tracking using silhouette information," IBM T .J. Watson Research Center, May 21, 2004 or earlier, 8 pages. Internet http://www.research.ibm.com/people/a/aws/documents/papers/SeniorVSPETS03.pdf.

Taylor, Russell H. et al., "A Telerobotic Assistant for Laparoscopic Surgery," IEEE Engineering in Medicine and Biology, May/Jun., 1995, pp. 279-288, vol. 14, Issue 3, IEEE.

Triggs, Bill et al., "Bundle Adjustment—A Modern Synthesis," 1999, 71 pages, Internet http://lear.inrialpes.fr/people/triggs/pubs/Triggs-va99.pdf.

Uecker, Darrin R. et al., "Automated Instrument Tracking in Robotically-Assisted Laparoscopic Surgery," Journal of Image Guided Surgery, vol. 1, No. 6, pp. 308-325, 1998.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Welch, Greg and Gary Bishop, "An Introduction to the Kalman Filter," University of No. Carolina at Chapel Hill, Dept. of Computer Science, TR 95-041, Apr. 5, 2004, pp. 1-16, Internet http://www.cs.unc.edu/~welch/media/pdf/kalman_intro.pdf.

West, Jay B. and Calvin R. Maurer, Jr., "Designing Optically Tracked Instruments for Image-Guided Surgery," IEEE Transaction on Medical Imaging, vol. 23, No. 5, May 2004, pp. 533-545.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

Zhao, Wenyi et al., "Alignment of Continuous Video onto 3D Point Clouds," IEEE Transactions on Pattern Analysis and Machine Intelligence (PAMI), Aug. 2005, vol. 27, No. 8, pp. 1305-1318.

Zhao, Wenyi et al., "Face Recognition: A Literature Survey," ACM Computing Surveys, Dec. 2003, vol. 35, No. 4, pp. 399-459.

Zhao, Wenyi, Table 1.1: "Comparison of related object and instrument tool tracking," from White Paper titled "Instrument Tool Tracking through Adaptive Fusion of Vision and Kinematics," Oct. 2006, p. 7.

PCT/US08/77611 International Search Report and Written Opinion of the International Searching Authority, mailed Jun. 12, 2009, 14 pages.

* cited by examiner

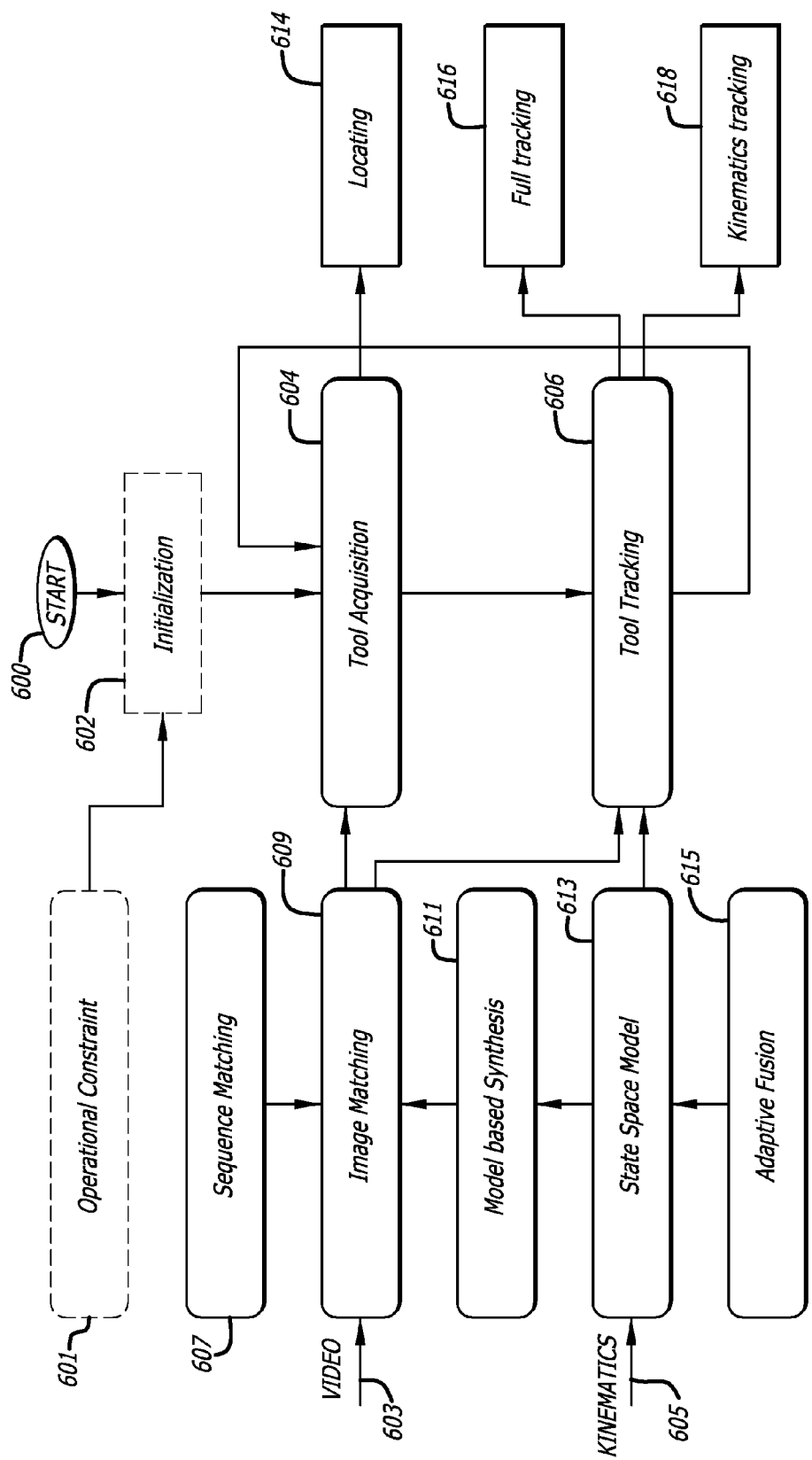

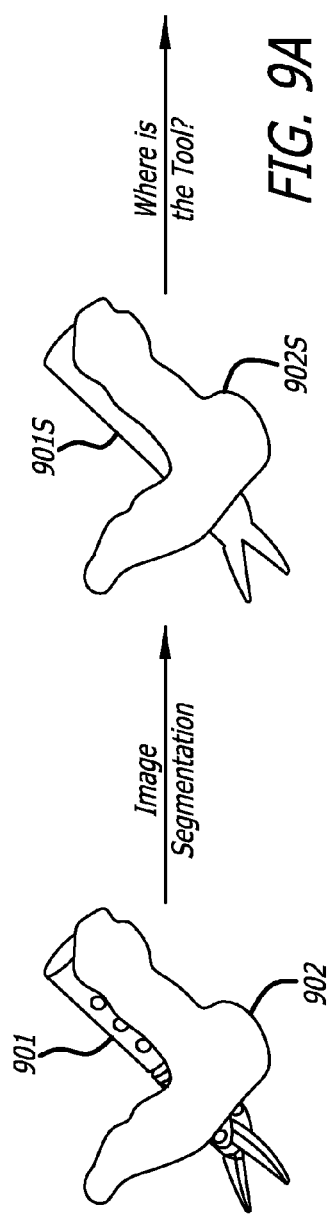
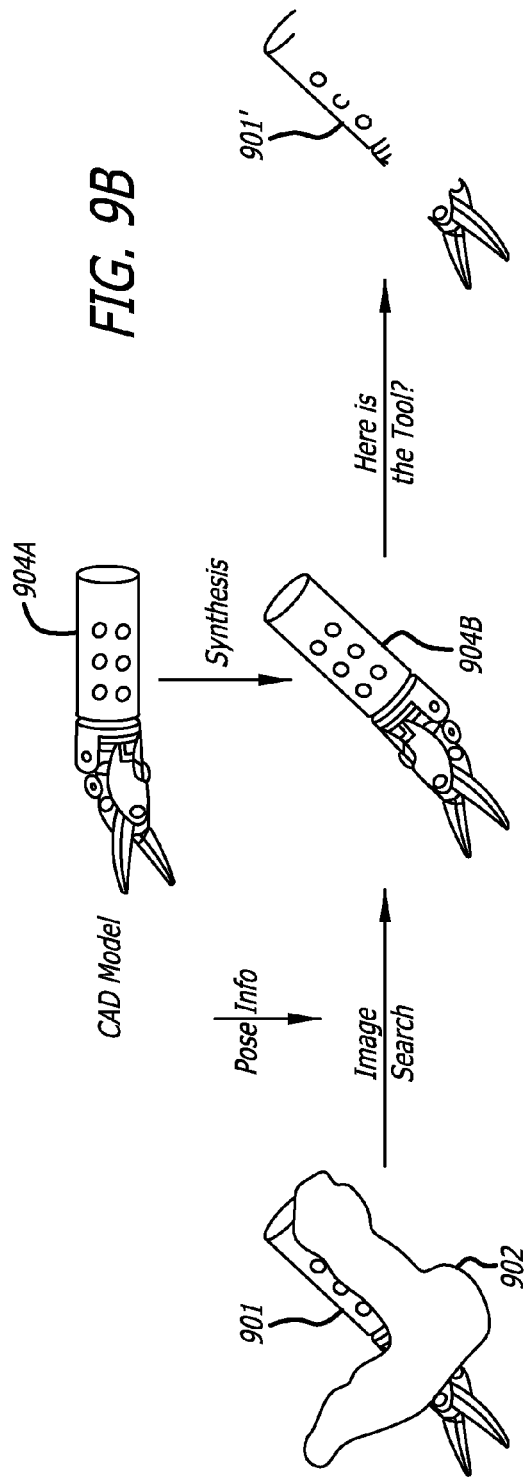
FIG. 9A
FIG. 9B

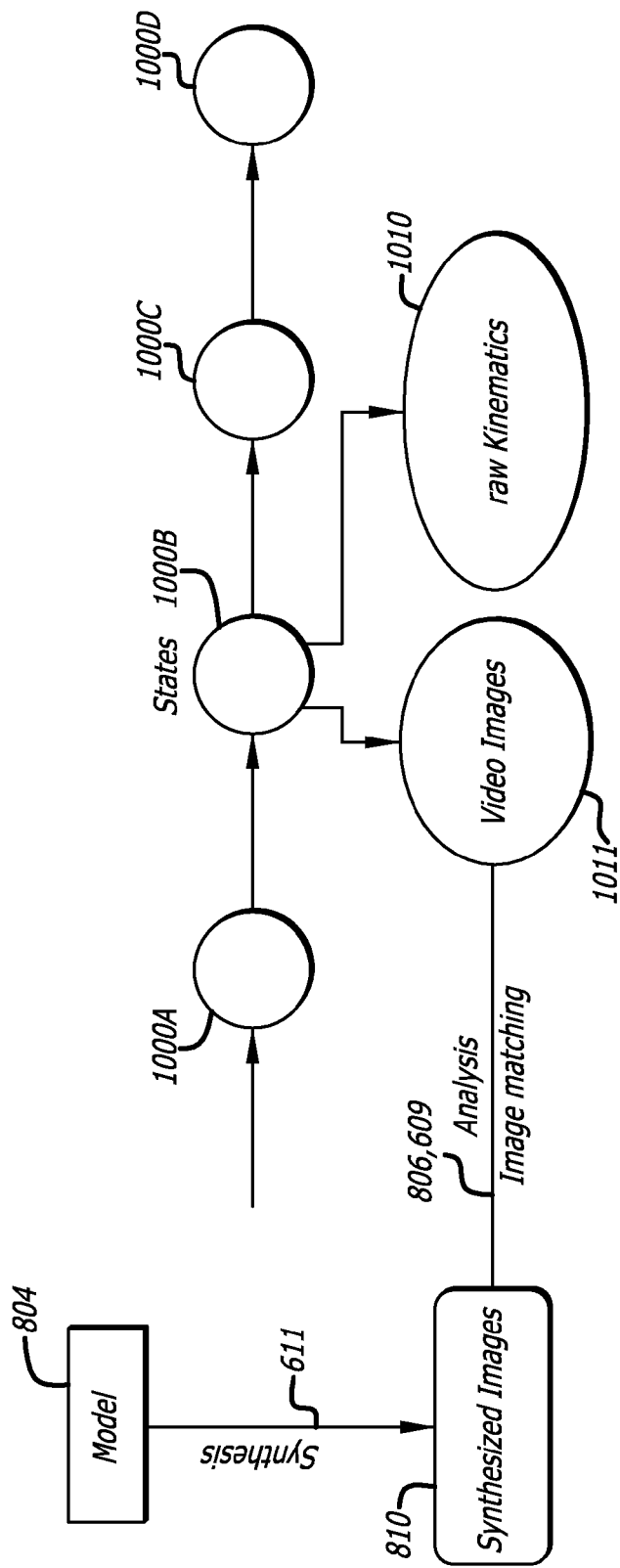

METHODS OF LOCATING AND TRACKING ROBOTIC INSTRUMENTS IN ROBOTIC SURGICAL SYSTEMS

FIELD

The embodiments of the invention relate generally to robots and robotic tools or instruments. More particularly, the embodiments of the invention relate to the acquisition and tracking of the position and orientation of robotic tools or instruments.

BACKGROUND

Minimally invasive surgical (MIS) procedures have become more common using robotic (e.g., telerobotic) surgical systems. An endoscopic camera is typically used to provide images to a surgeon of the surgical cavity so that the surgeon can manipulate robotic surgical tools therein. However if the robotic surgical tool is not in the field of view of the camera or it is otherwise hidden by tissue or other surgical tools, a surgeon may be left guessing how to move the robotic surgical tool when it is obscured from his view.

Moreover, tissue or organs of interest in a surgical cavity are often obscured from view. A surgeon may have to initially guess the location of an organ of interest within a surgical cavity and search around therein to place the organ and the robotic surgical tools within a field view of the endoscopic camera.

To better localize a surgical tool in the field of view, optical devices, such as light emitting diodes, have been attached to robotic surgical tools. However, optical devices can interfere with endoscopic surgical procedures and may not provide sufficiently accurate position and orientation information for a minimally invasive surgical system. A magnetic device may be applied to a robotic surgical tool in an attempt to magnetically sense its location. However, robotic surgical tools are often formed of metal and a magnetic device may not work well due to the interference generated by the movement of metal-tools and electrical motors in a minimally invasive surgical system. Moreover, these may provide only a single clue of the position of a robotic surgical tool.

BRIEF SUMMARY

The embodiments of the invention are summarized by the claims that follow below.

BRIEF DESCRIPTIONS OF THE DRAWINGS

FIG. 6A is a functional block diagram of a tool tracking architecture and methodology for a robotic system including one or more robotic instruments.

FIG. 9A is a figure to illustrate the process of pure image segmentation to localize a tool within an image.

FIG. 9B is a figure to illustrate the process of sequence matching and/or model-based synthesis to localize a tool within an image.

FIGS. 10A-10B illustrates elements of a state-space model to adaptively fuse robot kinematics information and vision-based information together.

Figure 11A:
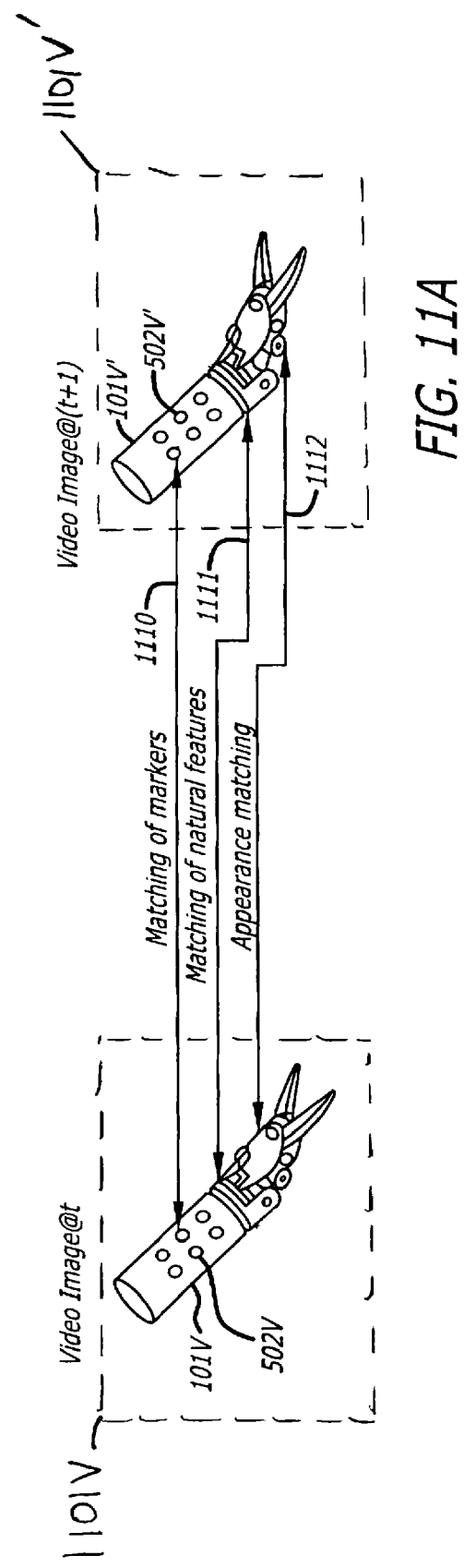
Figure 11B:
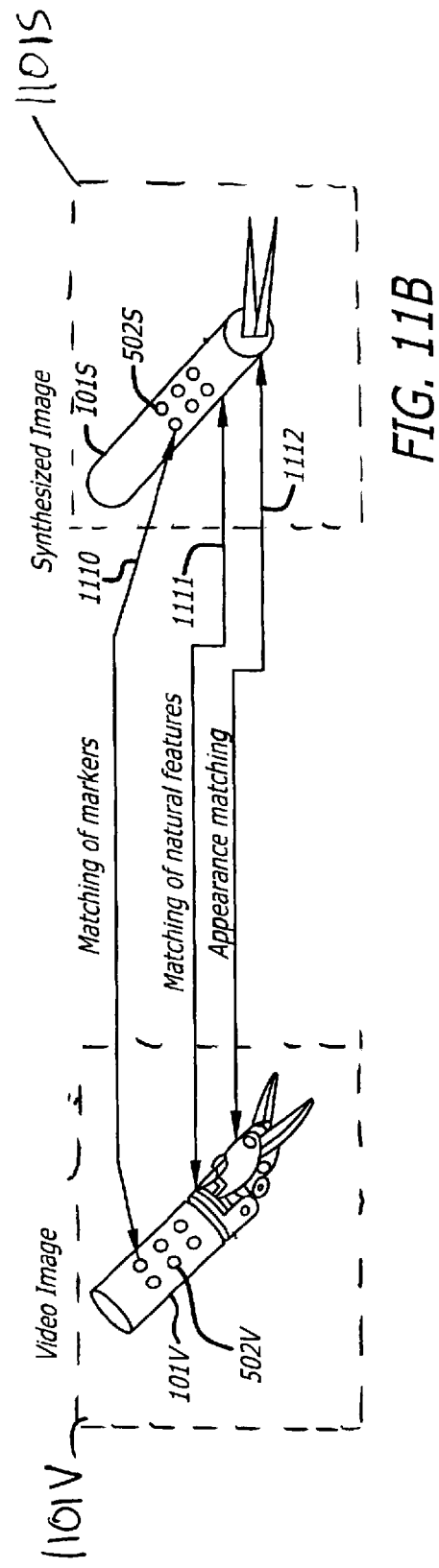
Figure 11C:
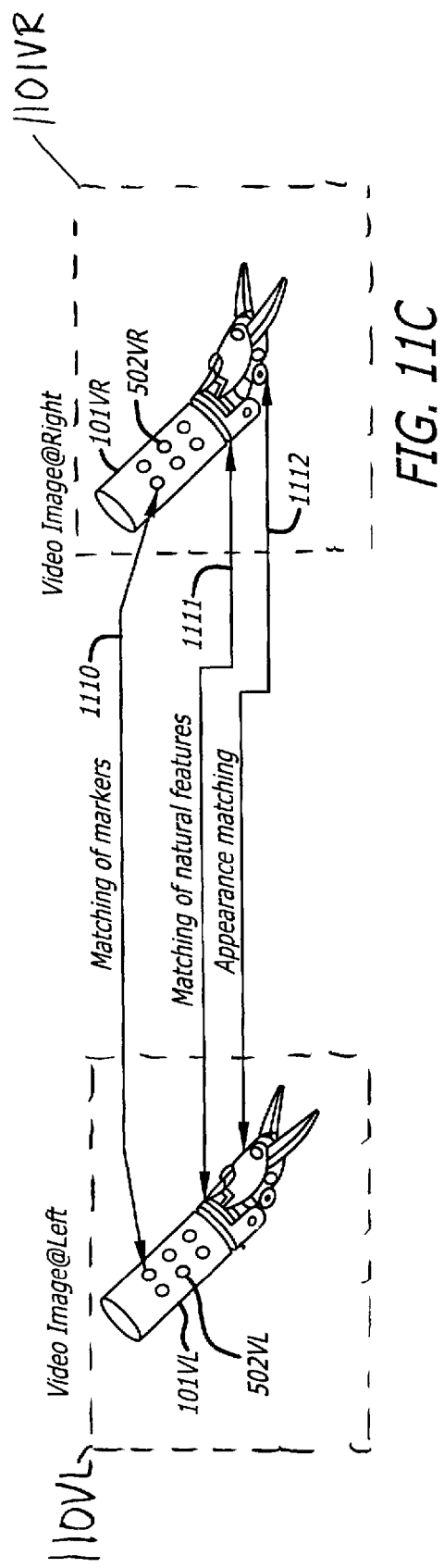

FIG. 11A-C illustrate various image matching techniques that may be used separately or collectively to determine pose information of a tool.

Figure 12A:
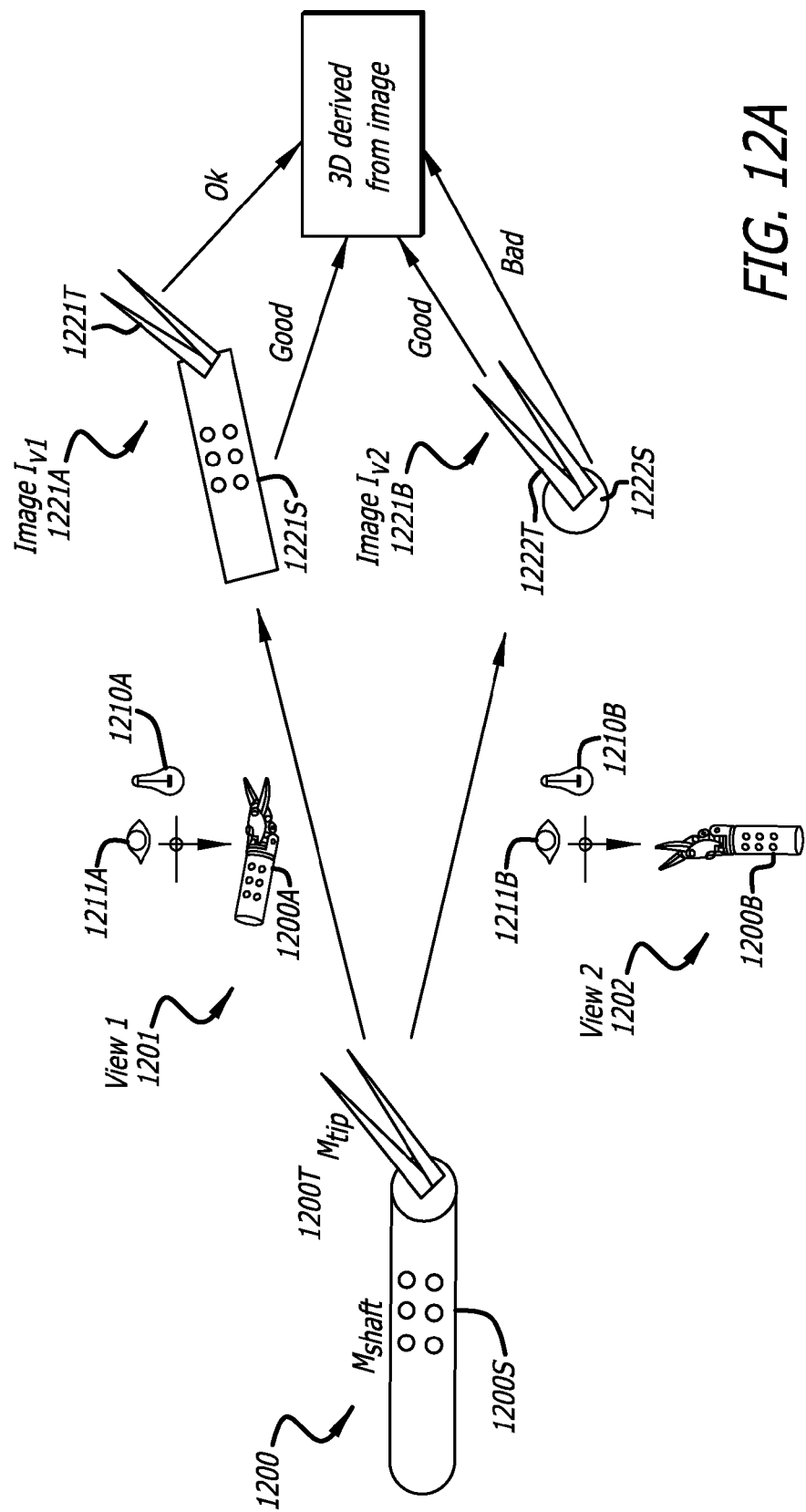

FIG. 12A is a diagram illustrating adaptive fusion under different viewing conditions.

Figure 12B:
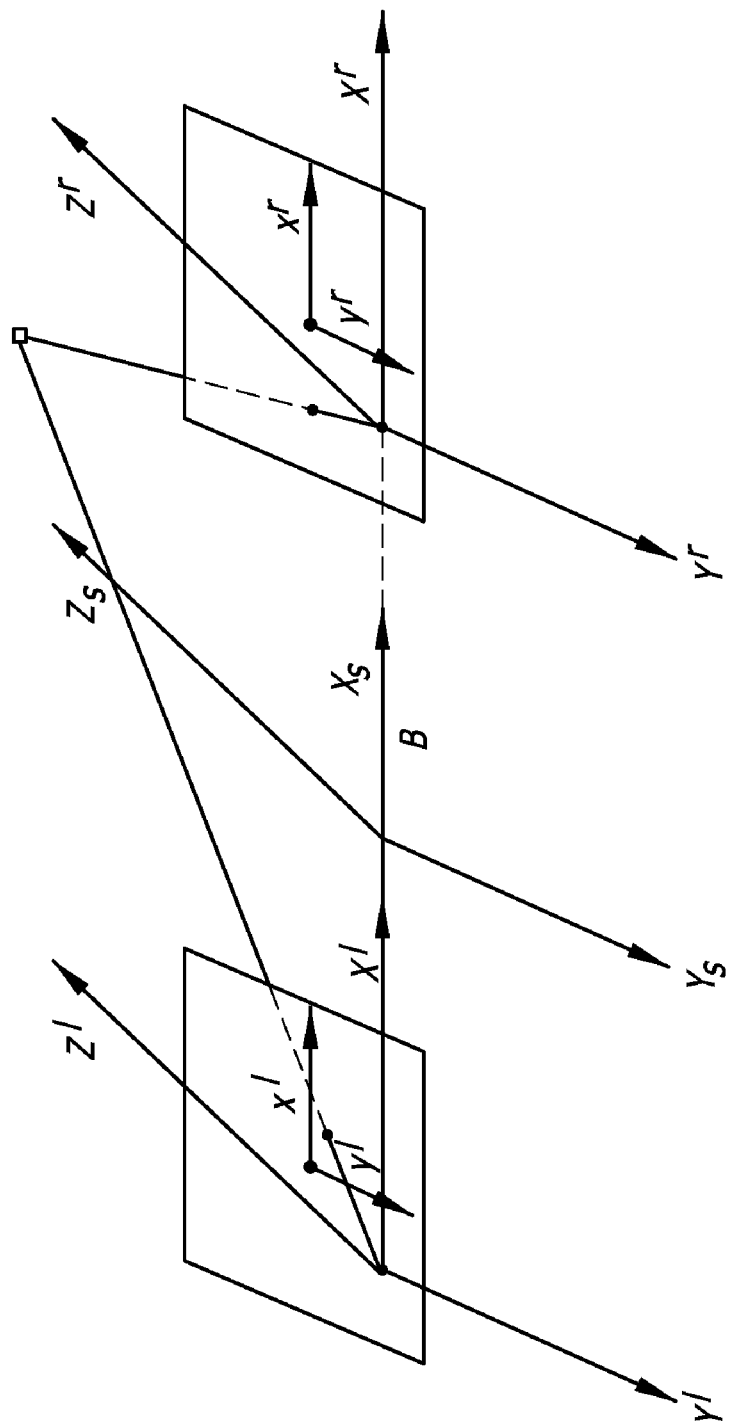

FIG. 12B is a diagram illustrating a set up for parallel stereo.

Figure 12C:
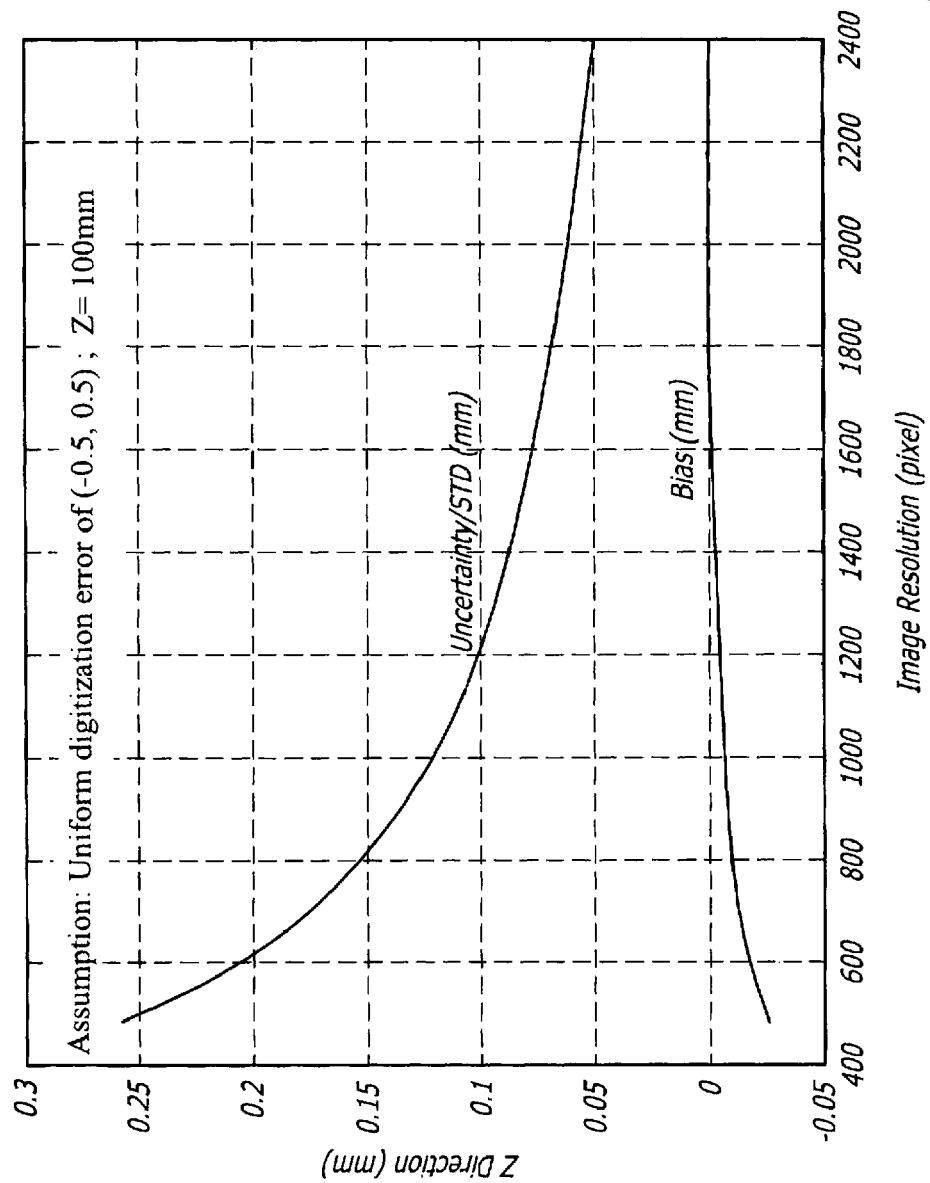
Figure 12D:
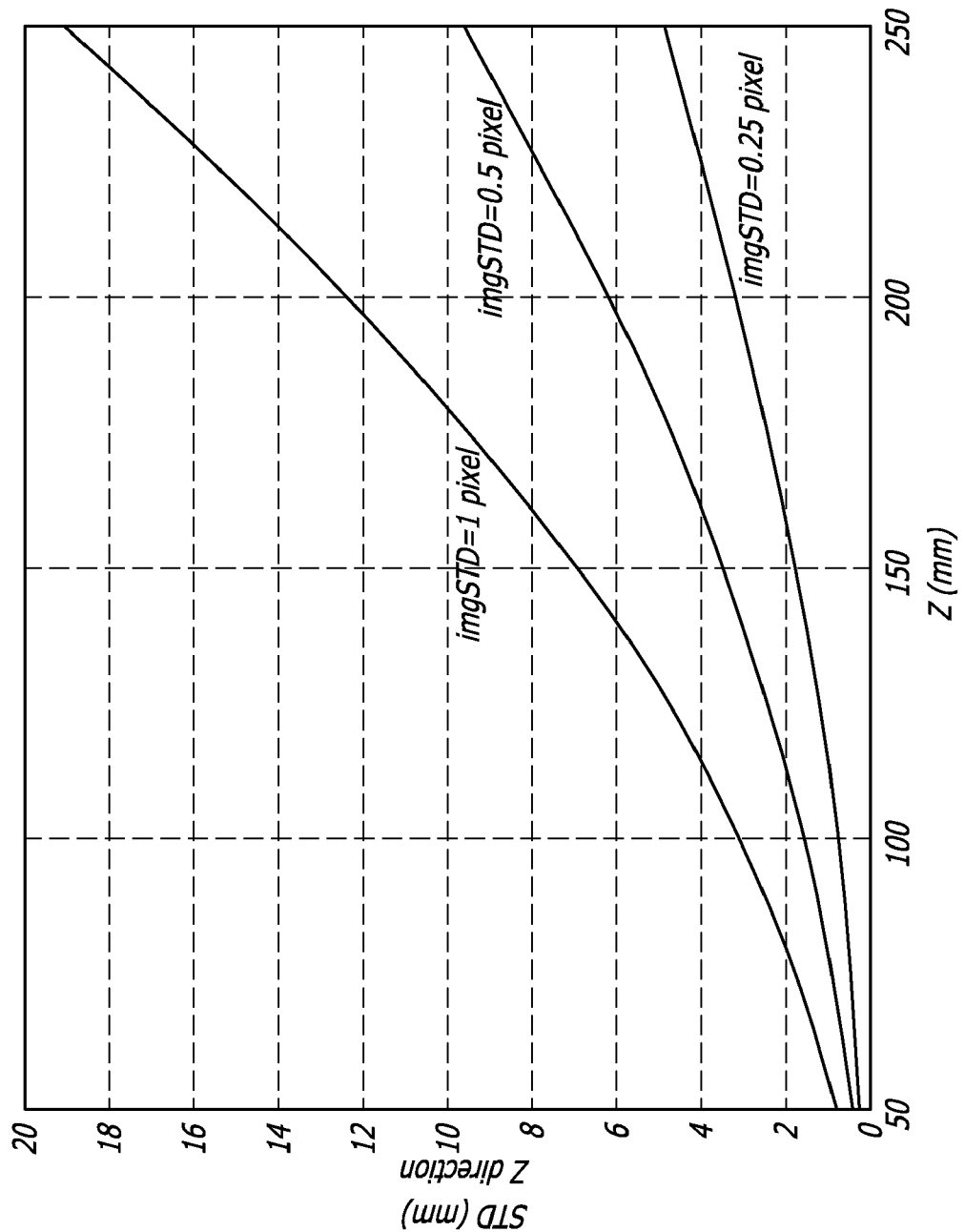
Figure 12E:
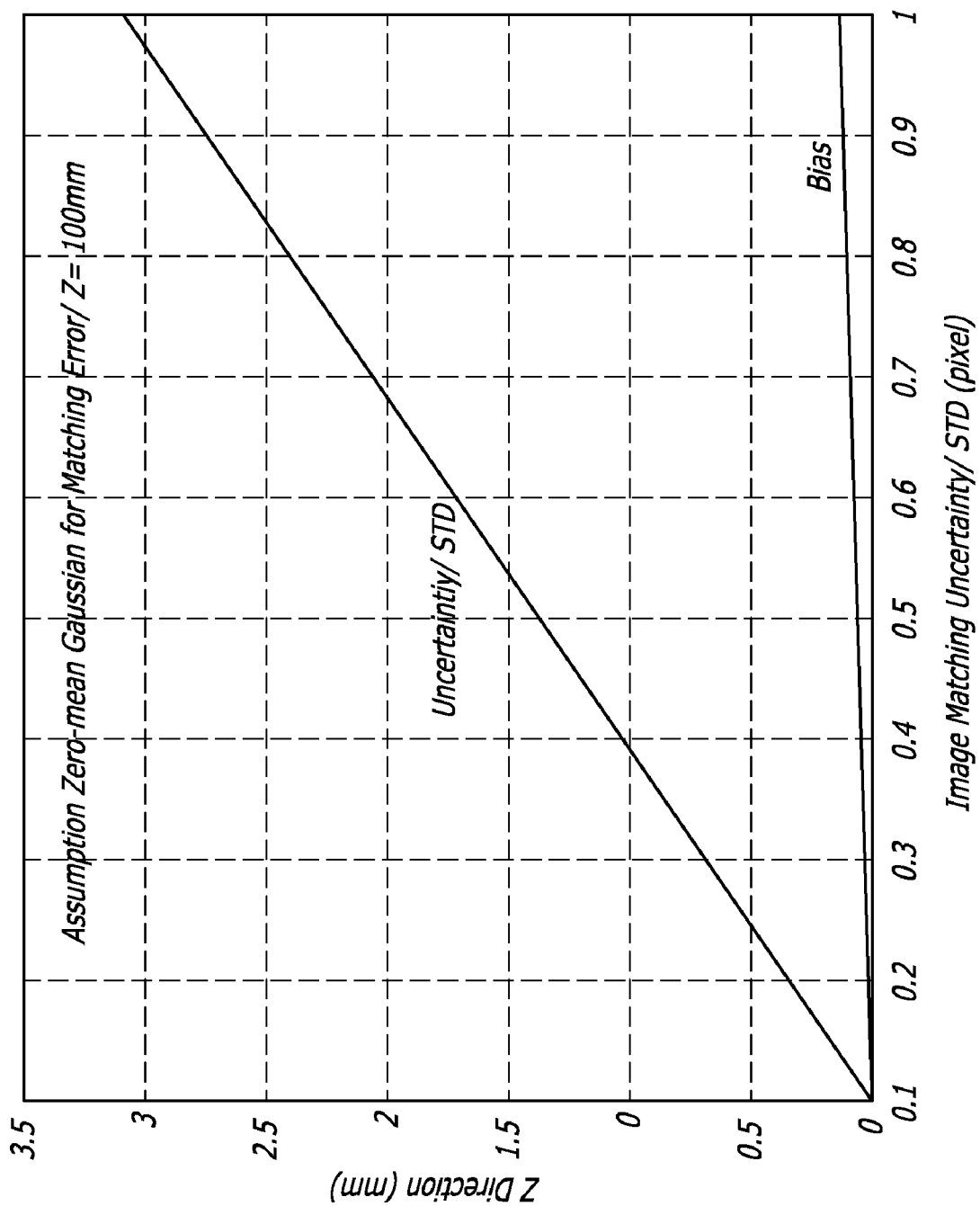

FIGS. 12C-12E are charts illustrating various view geometry statistics that may be used to enhance the performance of the state space model for adaptively fusing information sources together.

Figure 13A:
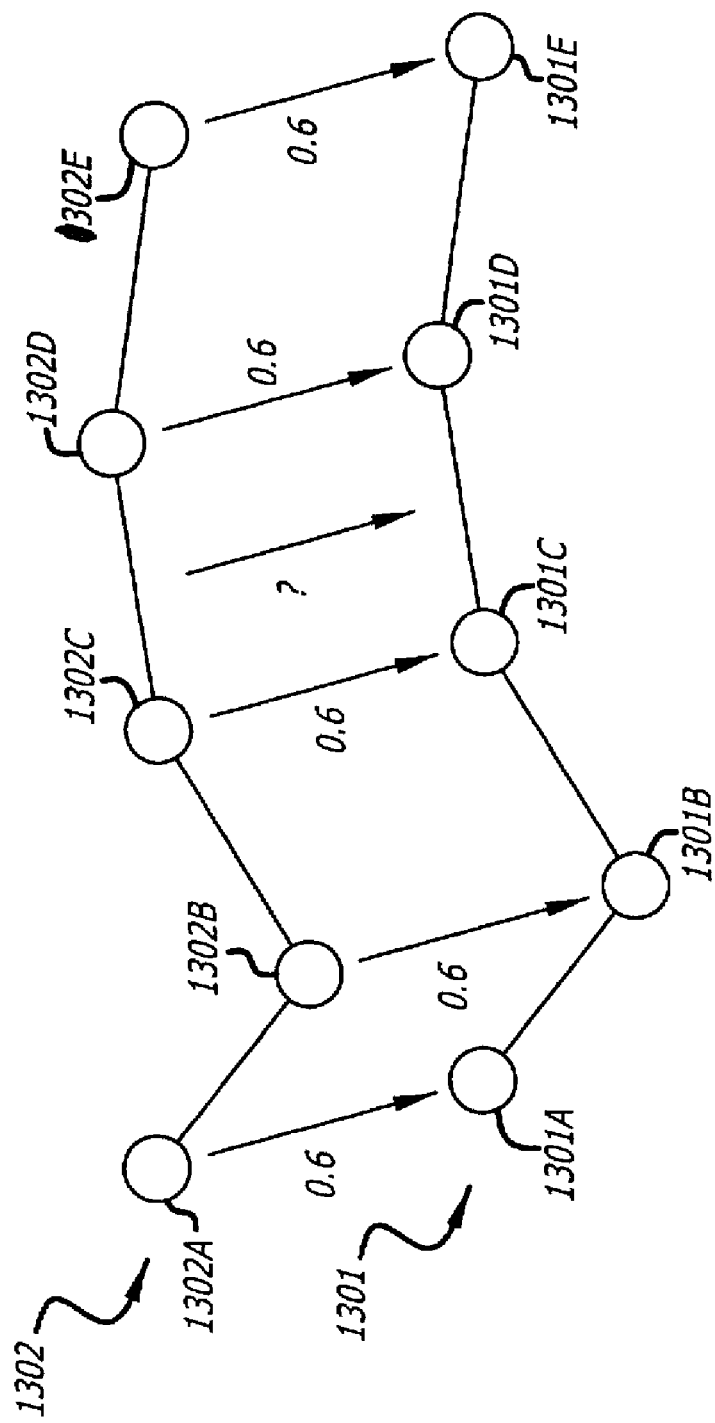
Figure 13B:
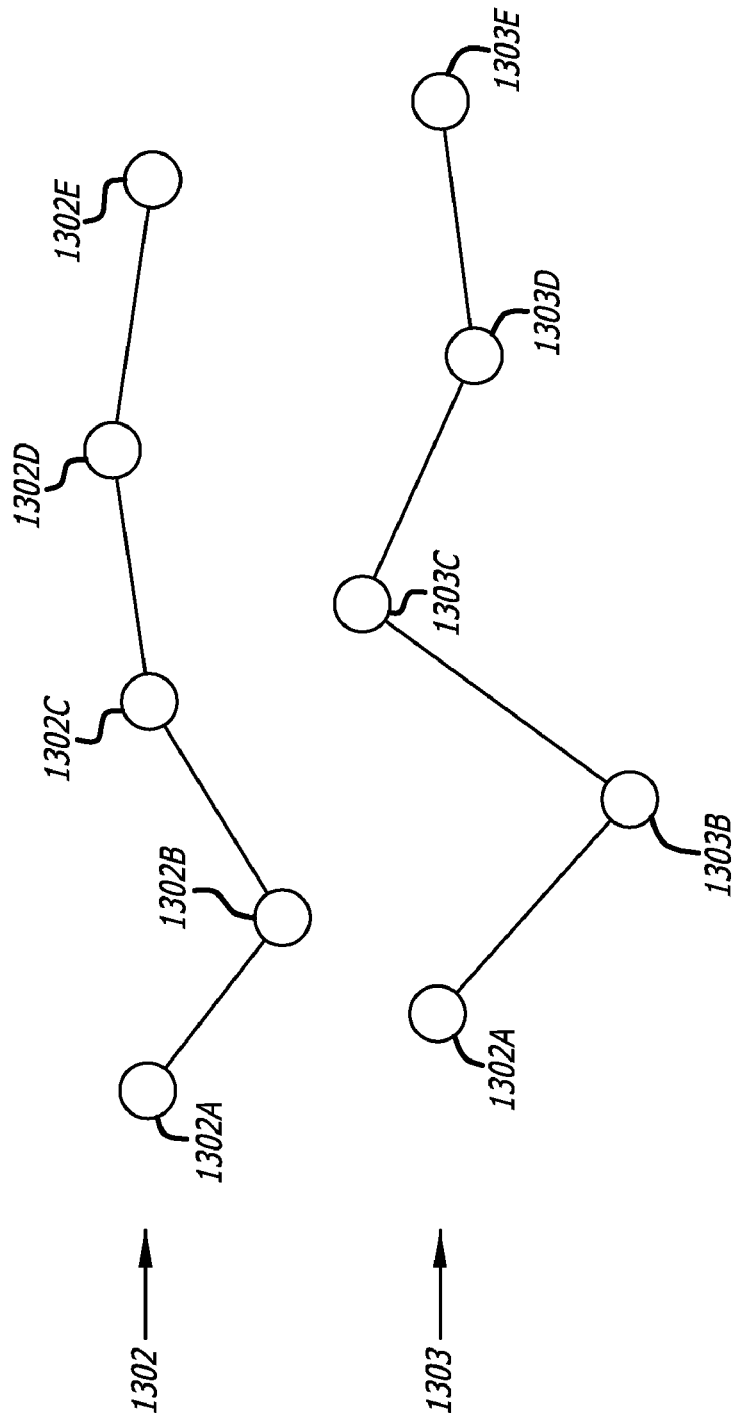

FIGS. 13A-13B are diagrams illustrating sequence matching of a feature in a sequence of one or more images from different sources.

Figure 14:
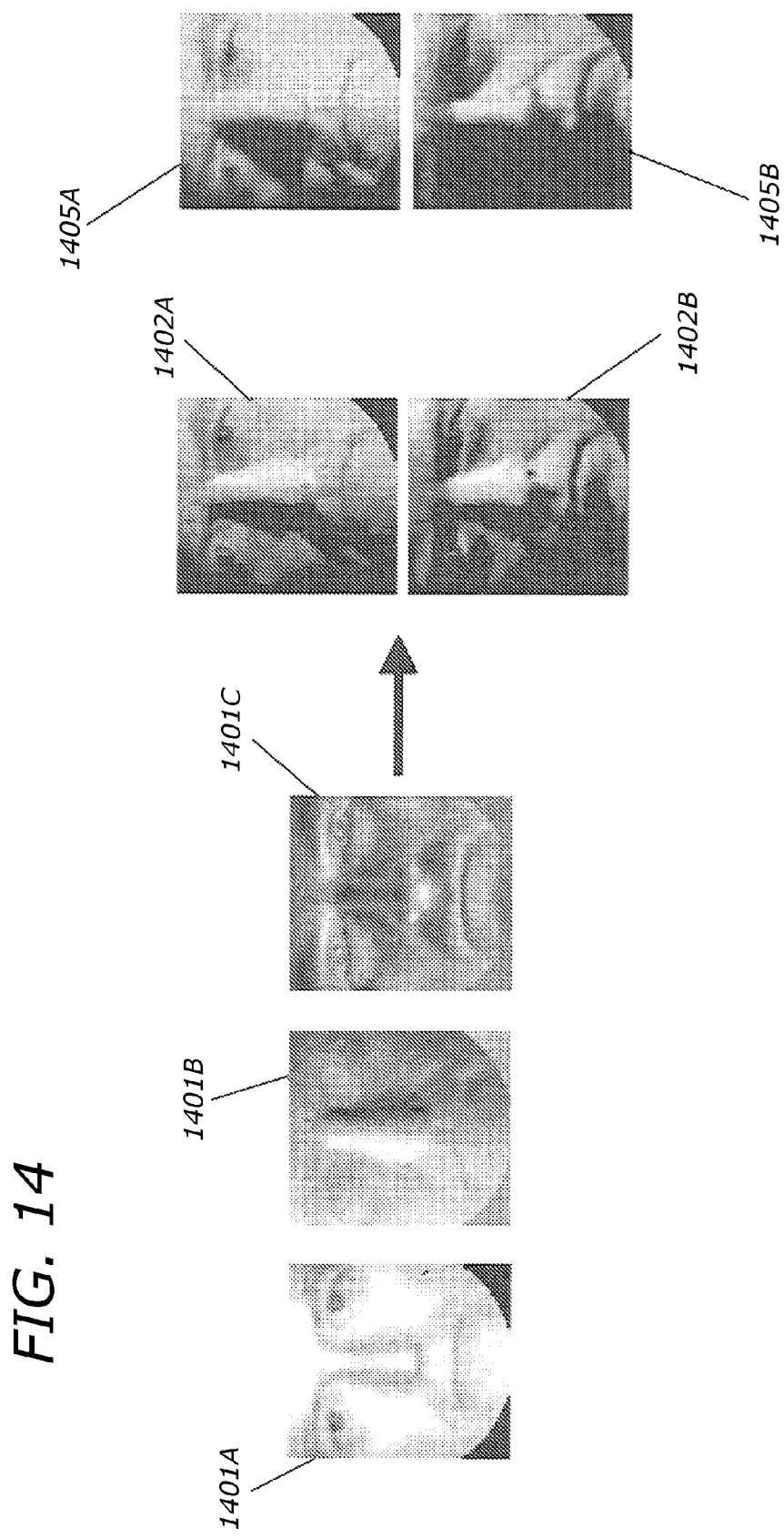

FIG. 14 is a diagram illustrating appearance learning of objects within an image.

Figure 15:
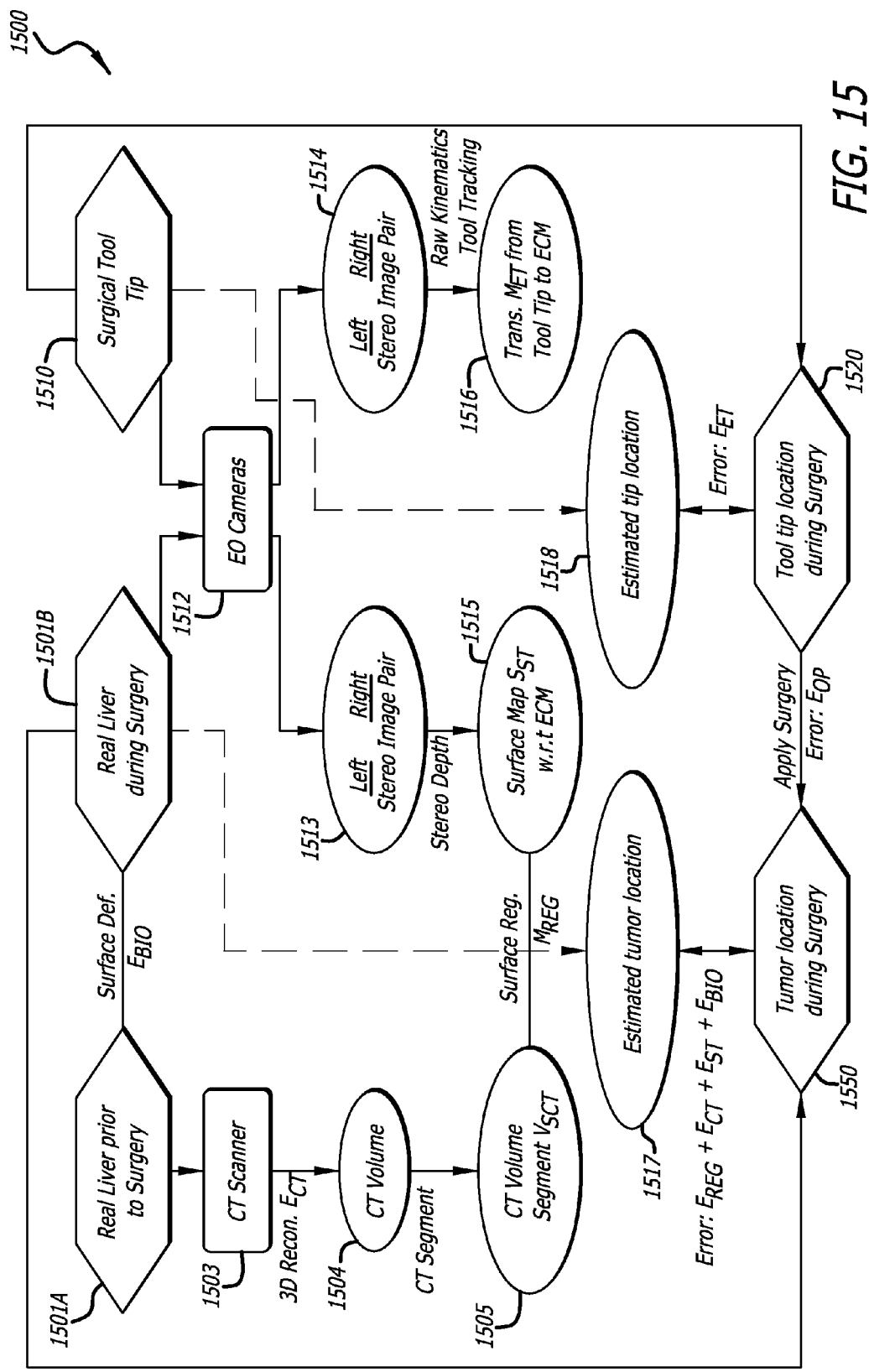

FIG. 15 is a flow chart of the application of tool tracking to image guided surgery.

Figure 16:
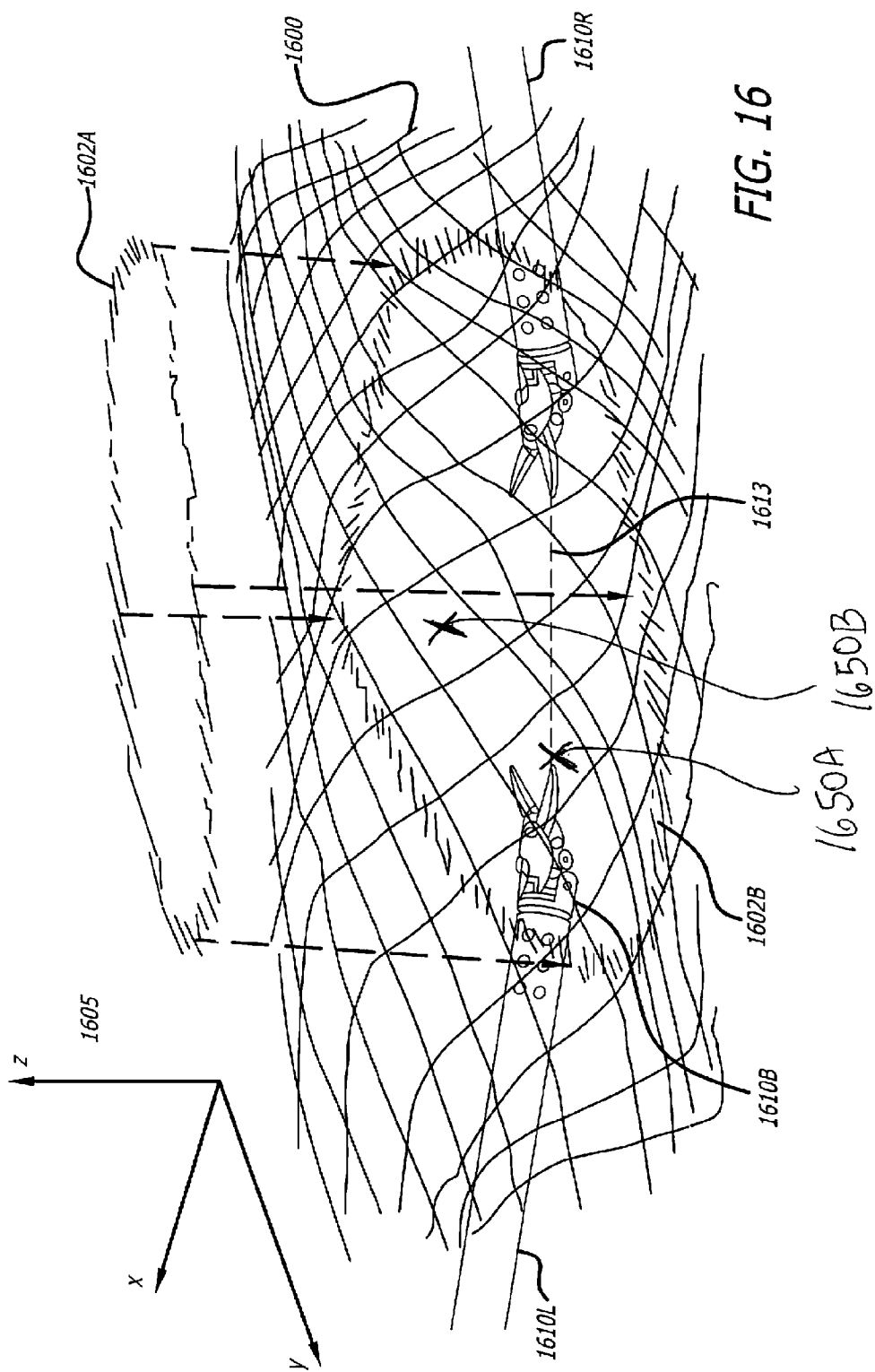

FIG. 16 is a perspective view of overlaying a pre-scanned image of tissue onto a depth map of a surgical site to provide image-guided surgery.

Figure 17:
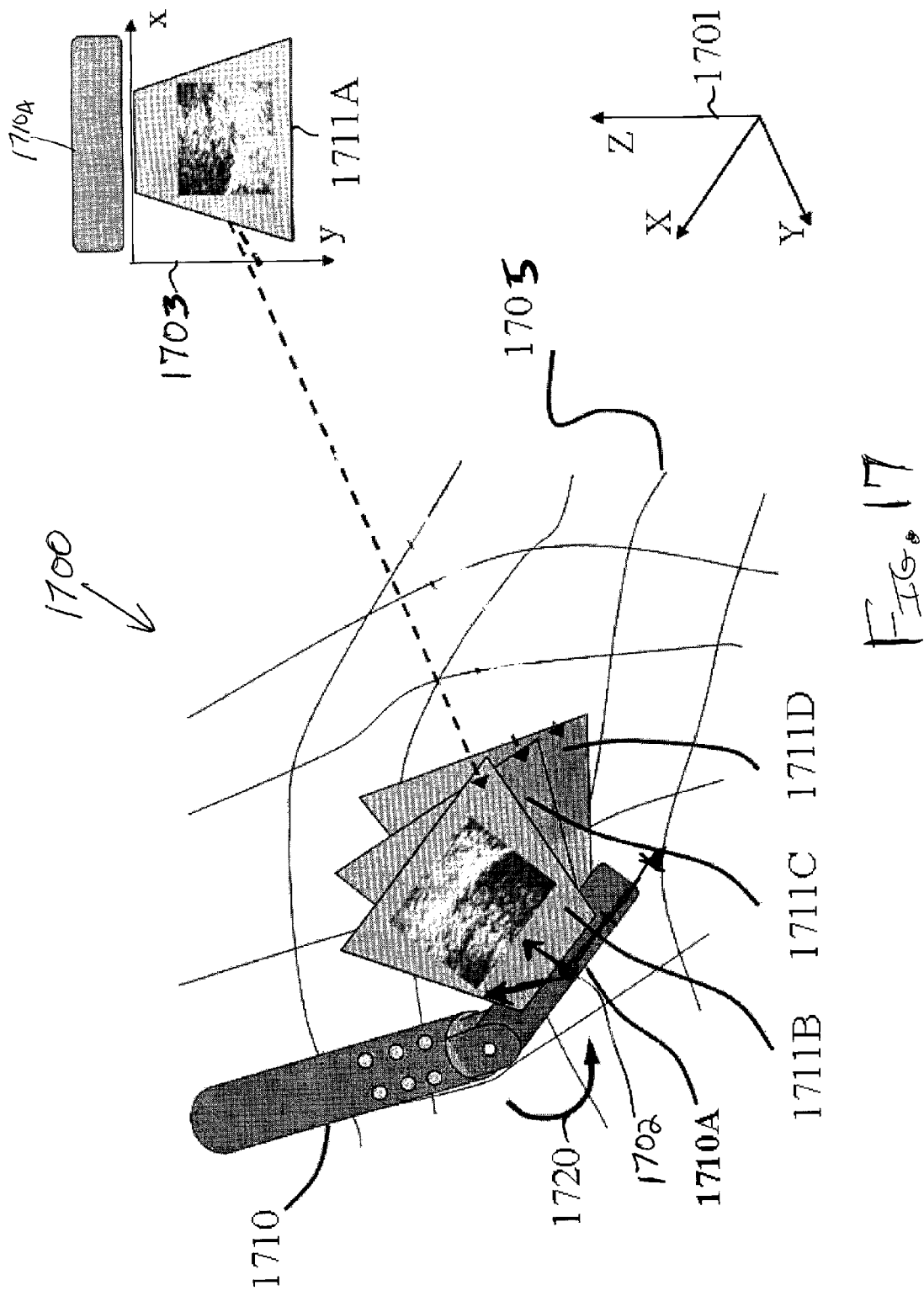

FIG. 17 is a perspective view of a surgical site with an ultrasound tool capturing ultrasound images for overlay onto a display.

DETAILED DESCRIPTION

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

Introduction

Aspects of the invention include methods, apparatus and integrated systems for tool acquisition (locating) and tool tracking (kinematics-tracking (pose predicting) and full-tracking) of robotic medical tools. The method/system for tool tracking systematically and efficiently integrates robot kinematics and visual information to obtain pose (position/orientation) information, which can be used to obtain a more accurate pose of a robotic surgical tool than robot kinematics or visual information alone, in either a camera coordinate system or a base coordinate system. Known kinematics transformation can be applied to the pose correction to achieve improved pose in any related coordinate system. A camera coordinate system is a coordinate system based on a chosen camera (for example, $(X^r, Y^r, Z^r)$ in FIG. 12B), or a common reference coordinate system for multiple cameras (for example, $(X_S, Y_S, Z_S)$ in FIG. 12B). In some aspects, tool tracking explores prior available information, such as the CAD models of tools, and dynamically learns the image appearances of the robotic instruments. In some aspects, tool tracking may be markerless so as not to interfere with normal robotic surgical procedures. Furthermore, tool tracking may provide continuous pose information of the robotic instruments including their relationships (e.g. tool A is on top of tool B and hence partially occluding tool B) with other tools so that image-based segmentation of the tools may be avoided.

Robotic Medical System

Figure 1A:
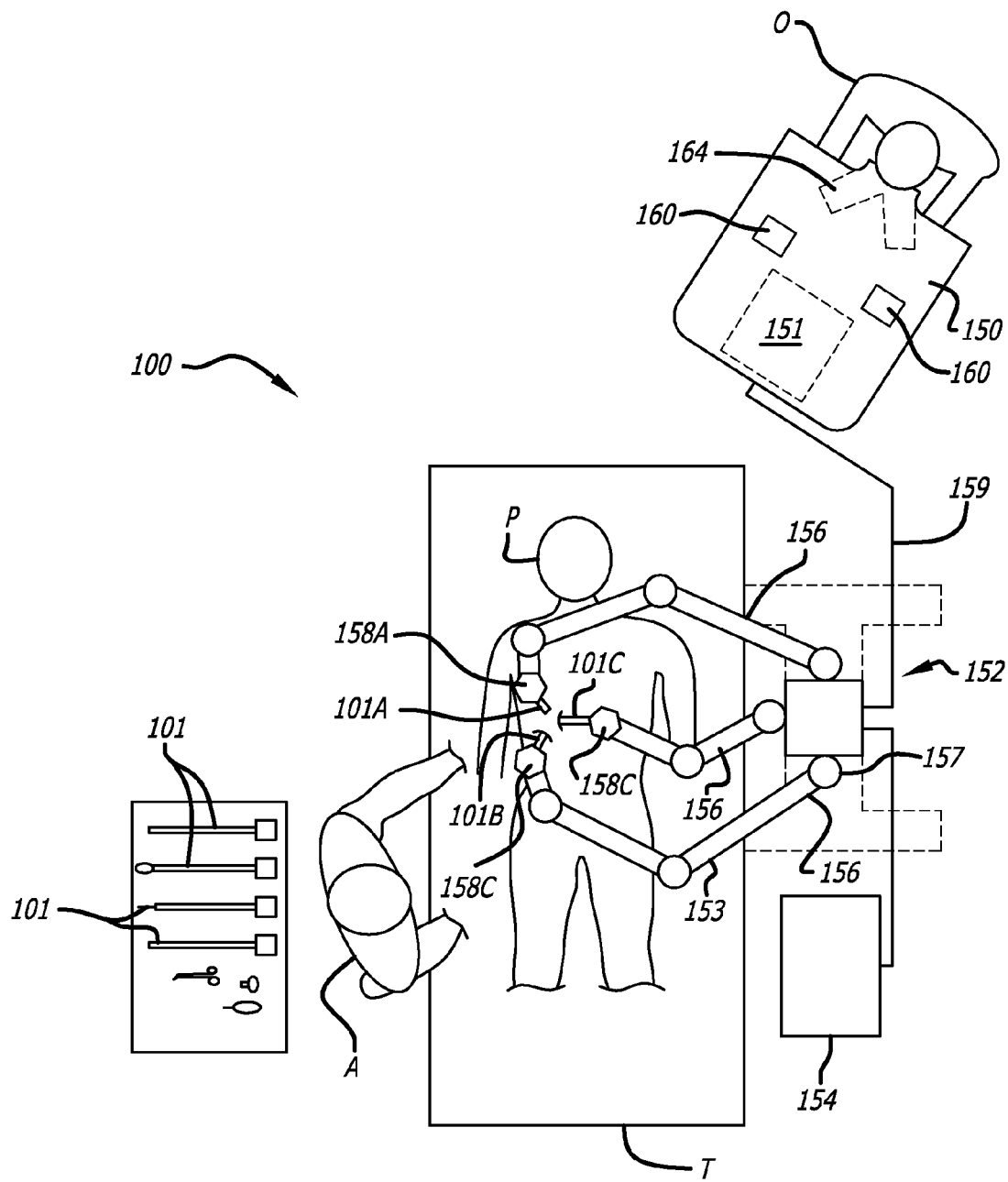
FIG. 1A is a block diagram of a robotic medical system including a stereo viewer and an image guided surgery (IGS) system with a tool tracking sub-system.

Referring now to FIG. 1A, a block diagram of a robotic surgery system 100 is illustrated to perform minimally invasive robotic surgical procedures using one or more robotic arms 158. Aspects of system 100 include telerobotic and autonomously operating features. These robotic arms often support a robotic instrument. For instance, a robotic surgical arm (e.g., the center robotic surgical arm 158C) may be used to support a stereo or three-dimensional surgical image capture device 101C such as a stereo endoscope (which may be any of a variety of structures such as a stereo laparoscope, arthroscope, hysteroscope, or the like), or, optionally, some other imaging modality (such as ultrasound, fluoroscopy, magnetic resonance imaging, or the like). Robotic surgery may be used to perform a wide variety of surgical procedures, including but not limited to open surgery, neurosurgical procedures (e.g., stereotaxy), endoscopic procedures (e.g., laparoscopy, arthroscopy, thoracoscopy), and the like.

A user or operator O (generally a surgeon) performs a minimally invasive surgical procedure on patient P by manipulating control input devices 160 at a master control console 150. A computer 151 of the console 150 directs movement of robotically controlled endoscopic surgical instruments 101A-101C via control lines 159, effecting movement of the instruments using a robotic patient-side system 152 (also referred to as a patient-side cart).

The robotic patient-side system 152 includes one or more robotic arms 158. Typically, the robotic patient-side system 152 includes at least three robotic surgical arms 158A-158C (generally referred to as robotic surgical arms 158) supported by corresponding positioning set-up arms 156. The central robotic surgical arm 158C may support an endoscopic camera 101C. The robotic surgical arms 158A and 158B to the left and right of center may support robotic instruments 101A and 101B, respectively, that may manipulate tissue.

Robotic instruments are generally referred to herein by the reference number 101. Robotic instruments 101 may be any instrument or tool that couples to a robotic arm that can be manipulated thereby and can report back kinematics information to the robotic system. Robotic instruments include, but are not limited to, surgical tools, medical tools, bio-medical tools, and diagnostic instruments (ultrasound, computer tomography (CT) scanner, magnetic resonance imager (MRI)).

Generally, the robotic patient-side system 152 includes a positioning portion and a driven portion. The positioning portion of the robotic patient-side system 152 remains in a fixed configuration during surgery while manipulating tissue. The driven portion of the robotic patient-side system 152 is actively articulated under the direction of the operator O generating control signals at the surgeon's console 150 during surgery. The driven portion of the robotic patient-side system 152 may include, but is not limited or restricted to robotic surgical arms 158A-158C.

The instruments 101, the robotic surgical arms 158A-158C, and the set up joints 156,157 may include one or more displacement transducers, positional sensors, and/or orientational sensors 185,186 to assist in acquisition and tracking of robotic instruments. From instrument tip to ground (or world coordinate) of the robotic system, the kinematics information generated by the transducers and the sensors in the robotic patient-side system 152 is reported back to the robotic system and a tool tracking and image guided surgery (IGS) system 351.

As an exemplary embodiment, the positioning portion of the robotic patient-side system 152 that is in a fixed configuration during surgery may include, but is not limited or restricted to set-up arms 156. Each set-up arm 156 may include a plurality of links and a plurality of joints. Each set-up arm may mount via a first set-up-joint 157 to the patient side system 152.

An assistant A may assist in pre-positioning of the robotic patient-side system 152 relative to patient P as well as swapping tools or instruments 101 for alternative tool structures, and the like, while viewing the internal surgical site via an external display 154. The external display 154 or another external display 154 may be positioned or located elsewhere so that images of the surgical site may be displayed to students or other interested persons during a surgery. Images with additional information may be overlaid onto the images of the surgical site by the robotic surgical system for display on the external display 154.

Figure 1B:
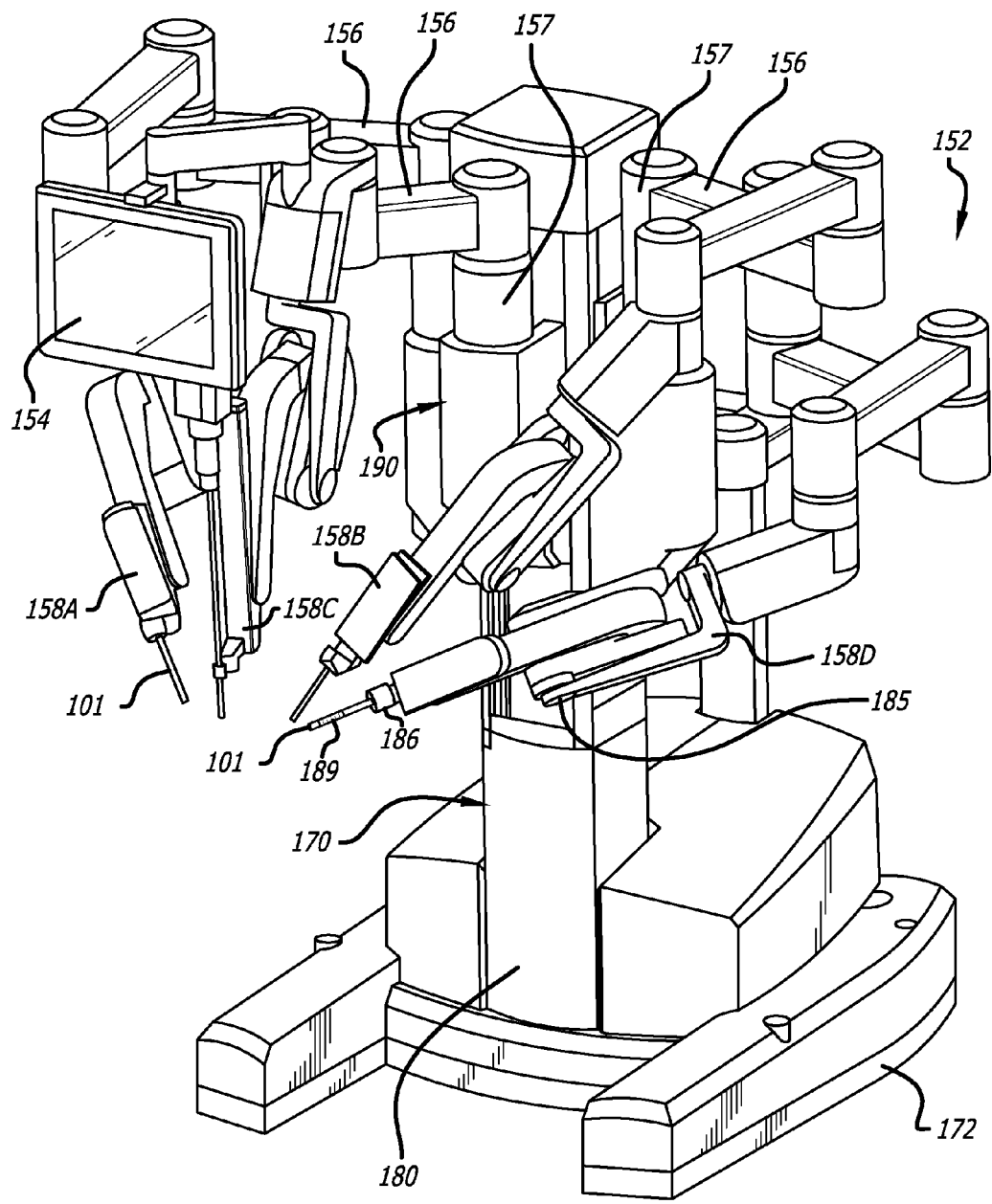
FIG. 1B is a block diagram of a patient side cart including robotic surgical arms to support and move robotic instruments.

Referring now to FIG. 1B, a perspective view of the robotic patient-side system 152 is illustrated. The robotic patient-side system 152 comprises a cart column 170 supported by a base 172. One or more robotic surgical arms 158 are respectively attached to one or more set-up arms 156 that are a part of the positioning portion of robotic patient-side system 152. Situated approximately at a central location on base 172, the cart column 170 includes a protective cover 180 that protects components of a counterbalance subsystem and a braking subsystem (described below) from contaminants.

Excluding a monitor arm 154, each robotic surgical arm 158 is used to control robotic instruments 101A-101C. Moreover, each robotic surgical arm 158 is coupled to a set-up arm 156 that is in turn coupled to a carriage housing 190 in one embodiment of the invention, as described below with reference to FIG. 3. The one or more robotic surgical arms 158 are each supported by their respective set-up arm 156, as is illustrated in FIG. 1B.

The robotic surgical arms 158A-158D may each include one or more displacement transducers, orientational sensors, and/or positional sensors 185 to generate raw uncorrected kinematics data, kinematics datum, and/or kinematics information to assist in acquisition and tracking of robotic instruments. The robotic instruments may also include a displacement transducer, a positional sensor, and/or orientation sensor 186 in some embodiments of the invention. Moreover, one or more robotic instruments may include a marker 189 to assist in acquisition and tracking of robotic instruments.

Endoscopic Video System

Figure 2:
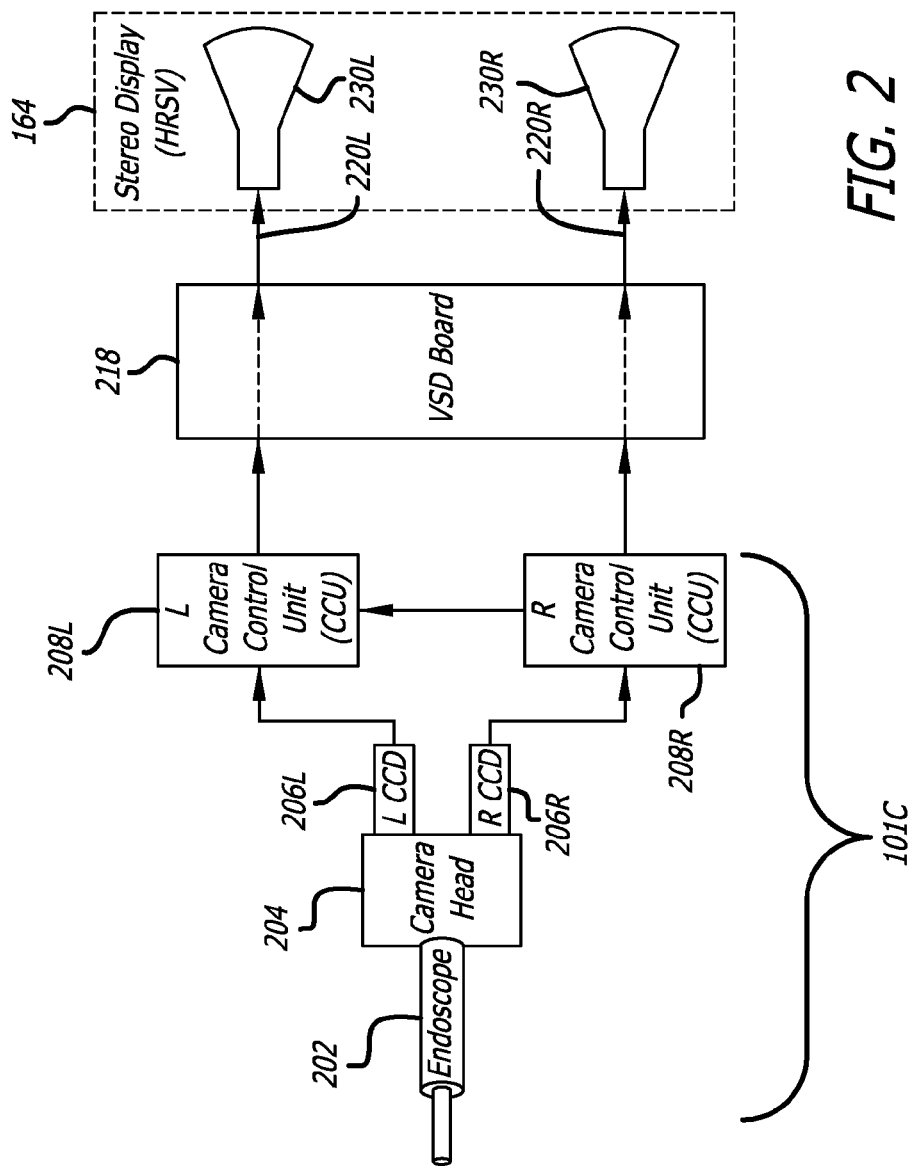
FIG. 2 is a functional block diagram of the video portion of the IGS system to provide a stereo image in both left and right video channels to provide three-dimensional images in a stereo viewer.

Referring now to FIG. 2, the stereo endoscopic camera 101C includes an endoscope 202 for insertion into a patient, a camera head 204, a left image forming device (e.g., a charge coupled device (CCD)) 206L, a right image forming device 206R, a left camera control unit (CCU) 208L, and a right camera control unit (CCU) 208R coupled together as shown. The stereo endoscopic camera 101C generates a left video channel 220L and a right video channel 220R of frames of images of the surgical site coupled to a stereo display device 164 through a video board 218. To initially synchronize left and right frames of data, a lock reference signal is coupled between the left and right camera control units 208L,208R. The right camera control unit generates the lock signal that is coupled to the left camera control unit to synchronize the left view channel to the right video channel. However, the left camera control unit 208L may also generates the lock reference signal so that the right video channel synchronizes to the left video channel.

The stereo display 164 includes a left monitor 230L and a right monitor 230R. As discussed further herein with reference to FIG. 4, the viewfinders or monitors 230L,230R may be provided by a left display device 402L and a right display device 402R, respectively. The stereo images may be provided in color by a pair of color display devices 402L,402R.

Additional details of a stereo endoscopic camera and a stereo display may be found in U.S. Pat. No. 5,577,991 entitled "Three Dimensional Vision Endoscope with Position Adjustment Means for Imaging Device and Visual Field Mask" filed on Jul. 7, 1995 by Akui et al; U.S. Pat. No. 6,139,490 entitled "Stereoscopic Endoscope with Virtual Reality Viewing" filed on Nov. 10, 1997 by Breidenthal et al; and U.S. Pat. No. 6,720,988 entitled "Stereo Imaging System and Method for use in Telerobotic Systems" filed on Aug. 20, 1999 by Gere et al.; all of which are incorporated herein by reference. Stereo images of a surgical site may be captured by other types of endoscopic devices and cameras with different structures. For example, a single optical channel may be used with a pair of spatially offset sensors to capture stereo images of the surgical site.

Figure 3:
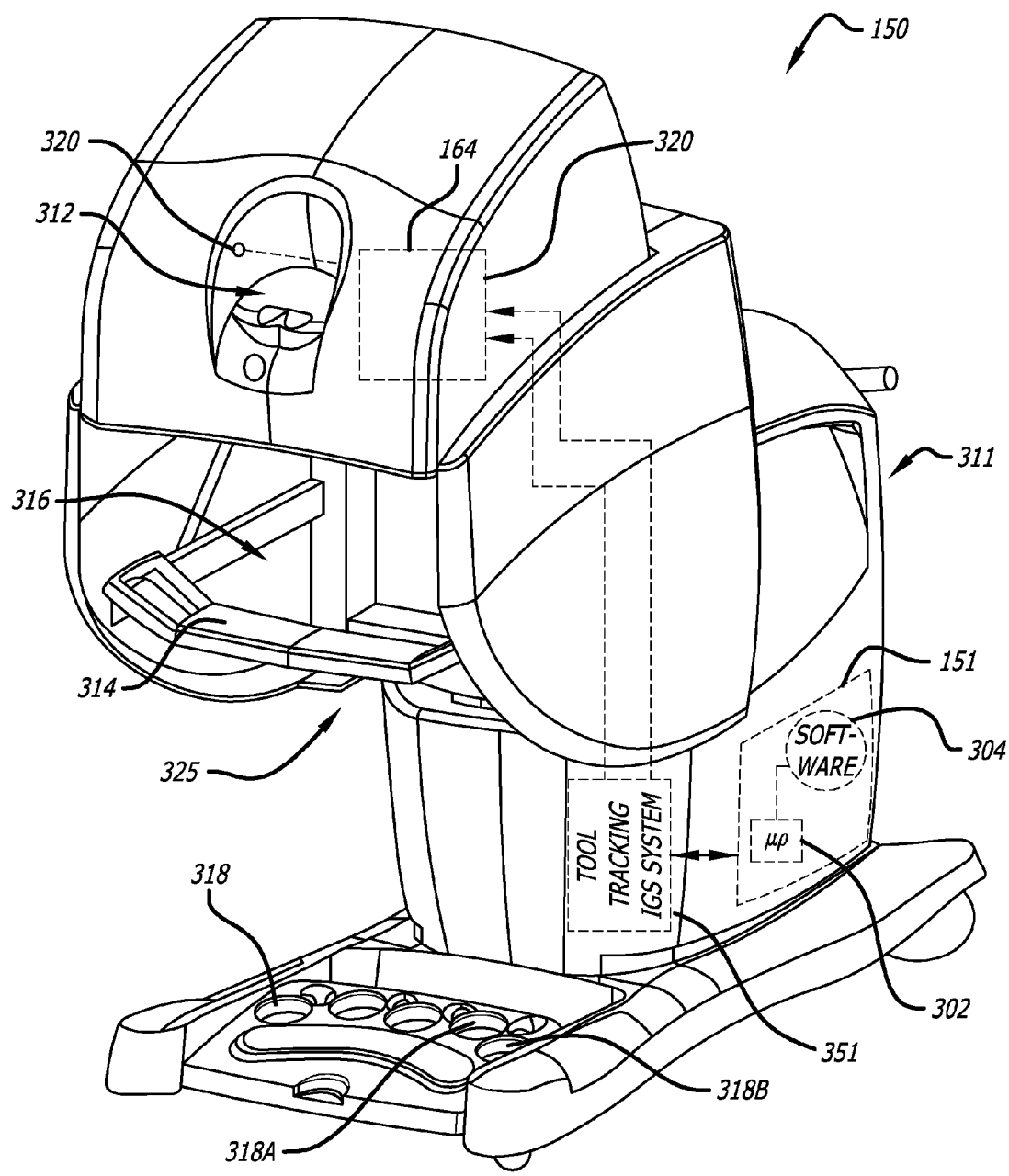
FIG. 3 is a perspective view of a robotic surgical master control console including a stereo viewer and an IGS system with tool tracking sub-system.

Referring now to FIG. 3, a perspective view of the robotic surgical master control console 150 is illustrated. The master control console 150 of the robotic surgical system 100 may include the computer 151, a binocular or stereo viewer 312, an arm support 314, a pair of control input wrists and control input arms in a workspace 316, foot pedals 318 (including foot pedals 318A-318B), and a viewing sensor 320. The master control console 150 may further include a tool tracking and image guided surgery system 351 coupled to the computer 151 for providing the tool images and tissue images overlaid on the visible surgical site images. Alternatively, the tool tracking and image guided surgery system 351 may be located elsewhere in the robotic surgical system 100, such as the patient side cart 152 or a separate computer system.

The stereo viewer 312 has two displays where stereo three-dimensional images of the surgical site may be viewed to perform minimally invasive surgery. When using the master control console, the operator O typically sits in a chair, moves his or her head into alignment with the stereo viewer 312 to view the three-dimensional annotated images of the surgical site. To ensure that the operator is viewing the surgical site when controlling the robotic instruments 101, the master control console 150 may include the viewing sensor 320 disposed adjacent the binocular display 312. When the system operator aligns his or her eyes with the binocular eye pieces of the display 312 to view a stereoscopic image of the surgical worksite, the operator's head sets off the viewing sensor 320 to enable the control of the robotic instruments 101. When the operator's head is removed the area of the display 312, the viewing sensor 320 can disable or stop generating new control signals in response to movements of the touch sensitive handles in order to hold the state of the robotic instruments. Alternatively, the processing required for tool tracking and image guided surgery may be entirely performed using computer 151 given a sufficiently capable computing platform.

The arm support 314 can be used to rest the elbows or forearms of the operator O (typically a surgeon) while gripping touch sensitive handles of the control input wrists, one in each hand, in the workspace 316 to generate control signals. The touch sensitive handles are positioned in the workspace 316 disposed beyond the arm support 314 and below the viewer 312. This allows the touch sensitive handles to be moved easily in the control space 316 in both position and orientation to generate control signals. Additionally, the operator O can use his feet to control the foot-pedals 318 to change the configuration of the surgical system and generate additional control signals to control the robotic instruments 101 as well as the endoscopic camera.

The computer 151 may include one or more microprocessors 302 to execute instructions and a storage device 304 to store software with executable instructions that may be used to generate control signals to control the robotic surgical system 100. The computer 151 with its microprocessors 302 interprets movements and actuation of the touch sensitive handles (and other inputs from the operator O or other personnel) to generate control signals to control the robotic surgical instruments 101 in the surgical worksite. In one embodiment of the invention, the computer 151 and the stereo viewer 312 map the surgical worksite into the controller workspace 316 so it feels and appears to the operator that the touch sensitive handles are working over the surgical worksite. The computer 151 may couple to the tool tracking and image guided surgery system 351 to execute software and perform computations for the elements of the image guided surgery unit.

The tool tracking system described herein may be considered as operating in an open-loop fashion if the surgeon operating the master console is not considered part of the system. If the robotic instrument is to be automatically controlled with the tool tracking system, such as in visual servoing systems used to control the pose of a robot's end-effector using visual information extracted from images, the tool tracking system may be considered to be operating in a closed visual-feedback loop.

Figure 4:
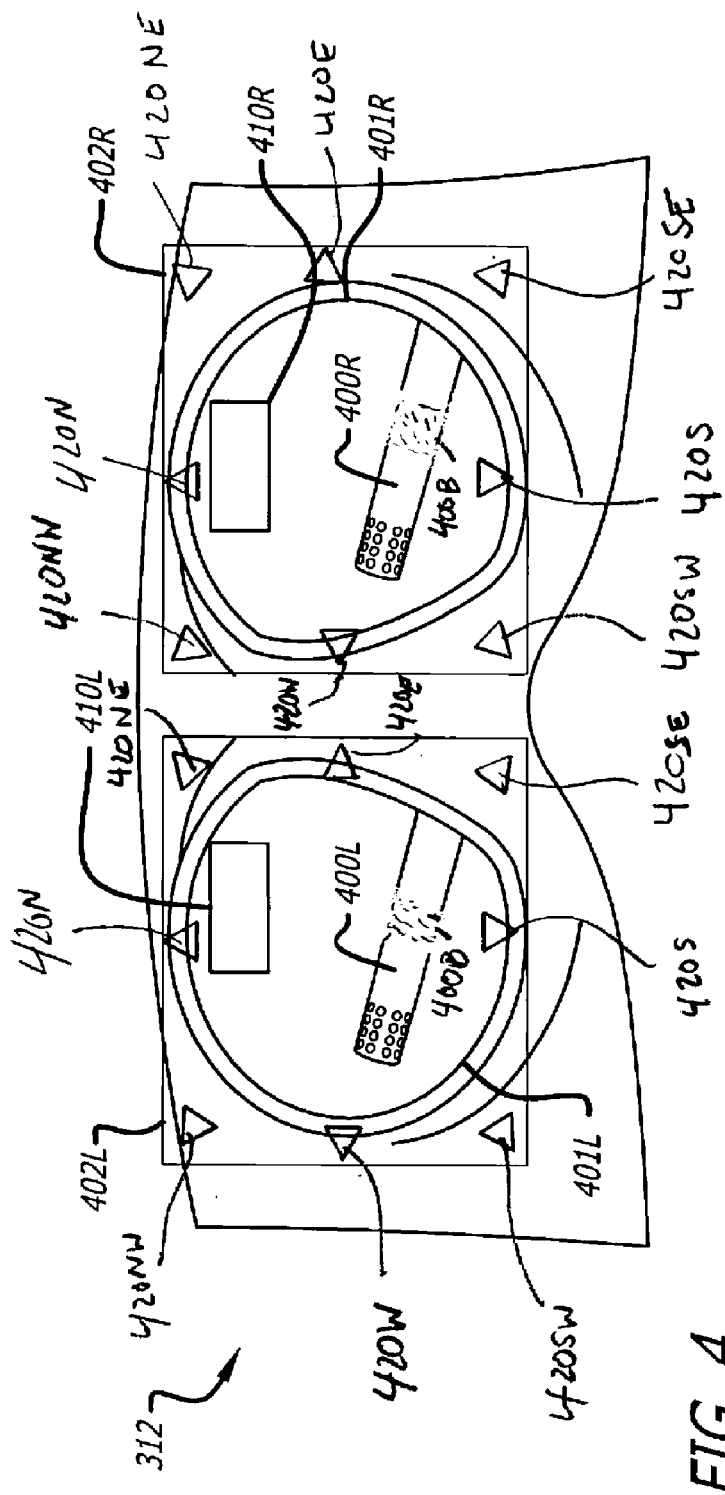
FIG. 4 is a perspective view of the stereo viewer of the robotic surgical master control console.

Referring now to FIG. 4, a perspective view of the stereo viewer 312 of the master control console 150 is illustrated. To provide a three-dimensional perspective, the viewer 312 includes stereo images for each eye including a left image 400L and a right image 400R of the surgical site including any robotic instruments 400 respectively in a left viewfinder 401L and a right viewfinder 401R. The images 400L and 400R in the viewfinders may be provided by a left display device 402L and a right display device 402R, respectively. The display devices 402L,402R may optionally be pairs of cathode ray tube (CRT) monitors, liquid crystal displays (LCDs), or other type of image display devices (e.g., plasma, digital light projection, etc.). In the preferred embodiment of the invention, the images are provided in color by a pair of color display devices 402L,402R; such as color CRTs or color LCDs.

In the stereo viewer, three dimensional maps (a depth map with respect to a camera coordinate system or equivalently a surface map of an object with respect to its local coordinate system is a plurality of three-dimensional points to illustrate a surface in three dimensions) of the anatomy, derived from alternative imaging modalities (e.g. CT scan, XRAY, or MRI), may also be provided to a surgeon by overlaying them onto the video images of the surgical site. In the right viewfinder 401R, a right image 410R rendered from a three dimensional map such as from a CT scan, may be merged onto or overlaid on the right image 400R being displayed by the display device 402R. In the left viewfinder 401L, a rendered left image 410L is merged into or overlaid on the left image 400L of the surgical site provided by the display device 402L. In this manner, a stereo image may be displayed to map out organ location or tissue location information in the surgical site to the operator O in the control of the robotic instruments in the surgical site, augmenting the operator's view of the surgical site with information that may not be directly available or visible by an endoscopic camera in the surgical site.

While a stereo video endoscopic camera 101C has been shown and described, a mono video endoscopic camera generating a single video channel of frames of images of the surgical site may also be used in a number of embodiments of the invention. Rendered images can also be overlaid onto the frames of images of the single video channel.

Tool Tracking

Tool tracking has a number of applications in robotic surgical systems. One illustrative application of tool tracking is to automatically control the motion of the endoscopic camera so that a surgeon automatically views regions of interest in a surgical site, thus freeing the surgeon from the camera control task. For example, robotic instruments are tracked so that the endoscopic camera is centered in the field of view of the surgical site. Another illustrative application for accurate tool tracking may be used to move a robotic instrument to reach a surgical target (e.g., a tumor) either automatically or by a surgeon. For a target such as a tumor that may be occluded, other real-time imaging modalities, such as ultra-sound or pre-scanned images, may be used with real-time tool tracking to move a robotic instrument to the tumor and remove it. Other illustrative applications of tool tracking include a graphic user interface (GUI) that facilities the entrance and re-entrance of robotic instrument during surgery. Tool tracking is very useful when robotic instruments are not in the field of view of the endoscopic camera or are otherwise obscured in the field of view of the camera. In such scenarios, robotic kinematics provides information through the proposed state-space model.

In one embodiment of the invention, a tool tracking system and architecture is provided that fully integrates kinematics information and visual information for robust and accurate tool tracking performance. Results of tool localization and tracking are made accurate and reliable by adaptively combining together robust kinematics information and accurate geometric information derived from video. The tool tracking system performs locating (determining absolute locations/poses with stereo video), tracking (integrating visual and kinematics) and predicting (kinematics while the tool or a portion thereof is not visible) functions.

Technical capabilities in the tool tracking system include an analysis-by-synthesis for image matching and a sequential Bayesian approach which fuses together visual and kinematic information.

An analysis-by-synthesis capability makes it possible to explore the prior information that is of concern, such as information about the tools and not the tissue and surrounding environment. The basic procedure in analysis-by-synthesis is to synthesize an image based on the model (geometry and texture) and the current pose (position/location and orientation) of a tool and then compare it against real images. The error between the real and synthesized images is the driving force for better estimation of tool pose. To make this approach more robust, e.g., handling varying illumination and the natural wear of a tool; appearance-based learning may be applied to update the model for a specific tool. Alternatively, matching may be performed using features, such as edges and/or corners, that are more robust to lighting variation.

To obtain the absolute pose (location and orientation), stereo imaging may be used along with the analysis-by-synthesis (ABS) techniques. Instead of just a feature point based stereo that may require markers, a stereo approach may be provided based on the tool (or some of its parts). To further improve the robustness, stereo and ABS techniques may be applied to a sequence of images (e.g., the same location and different orientations or different locations and different orientation). Sequence-based matching makes the procedure less vulnerable to local minimum in the process of optimization/estimation.

A sequential Bayesian approach may be applied to fuse visual information and robot kinematics to efficiently track tools. In this approach, the states provide zero-order kinematics of the tools (e.g. current position and orientation, or pose), and the first-order kinematics of the tools (e.g. translational and angular velocity). Depending upon the complexity of the underlying physical system, higher-order or lower-order state space model may be adopted. For a linear space model, a linear Kalman filtering may be applied when the noise can be approximated as Gaussian. For a nonlinear state space model, an extended Kalman filtering may be used to filter out noise from observations and state dynamics. For a complex state space model that requires a point distribution function (pdf), sequential Monte Carlo method (e.g., particle filtering) can be applied where the point distribution function may be represented by a set of representative samples.

One challenge in fusing information from the various sources is that the sources should be correctly characterized, for example, in terms of observation noise characteristics. Taking the simplest case of Gaussian noises that can be characterized by means and co-variance, we can estimate the co-variance matrices quite robustly since we know the geometry of the robotic instruments (location and orientation) and their relative positions. For example, observation (e.g., pixel location of a feature point) from a robotic instrument that is under a slanted viewing angle or is occluded by other tools has a large variance.

Figure 5A:
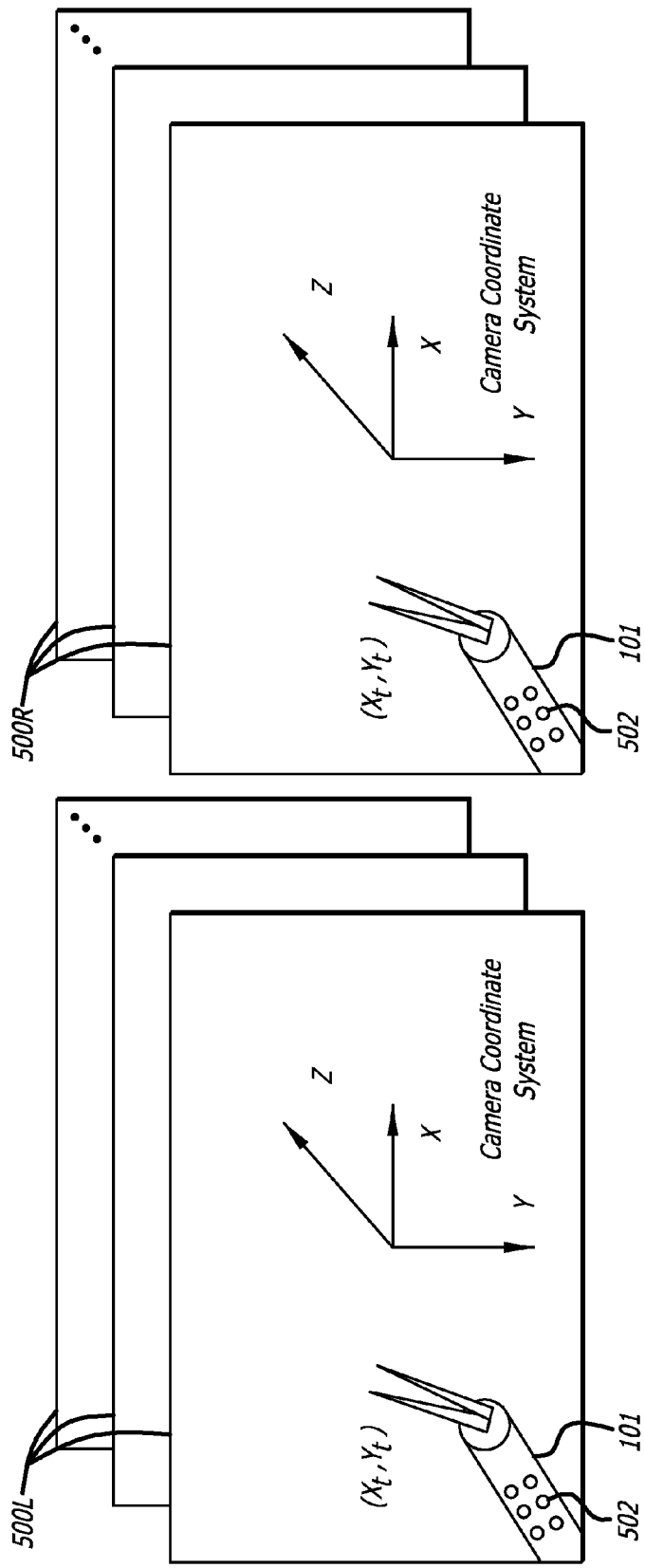
FIG. 5A is a perspective view of a sequence of video frames including video images of a robotic medical tool that may be used to perform tool tracking.

Referring now to FIG. 5A, tool tracking involves determining a pose of a robotic instrument 101 including its position or location ($X_t, Y_t, Z_t$) and its orientation in the camera coordinate system as it moves in, around, and out of the surgical site. A full pose description may not only include the location and orientation of a robotic instrument in a three dimensional space but may further include the pose of an end-effector, if any. Positional information or pose as used herein may be used to refer to one or both the location and orientation of a robotic instrument.

A sequence of left video frames 500L within a camera coordinate system and a sequence of right video frames 500R within another camera coordinate system (or one pair of video frames/images from left and rights views) may be used for tool tracking in one embodiment of the invention. Alternatively, a single view with a single sequence of video frames may be used for tool tracking in another embodiment of the invention. Alternatively, a single video frame may be used for tool tracking in yet another embodiment of the invention providing partially corrected pose estimates.

A marker 502 on the robotic instrument 101 may be used to assist in the tool tracking if visible or otherwise sensible. In one embodiment of the invention, the marker 502 is a painted marker minimally altering the robotic instruments. In other embodiments of the invention, markerless tool tracking is provided with no modification of the robotic instruments. For example, natural image features of a robotic tool may be detected as natural markers and/or image appearance of the tools and the CAD model of tools may be used to provide tool tracking.

In one embodiment of the invention, video information from an endoscopic camera and kinematics of the robotic arm and robotic instrument are used as cues to determine the pose of the robotic instrument in the surgical site. If the robotic instrument is not visible to the camera, the video information alone is insufficient to determine position but the kinematics adds the missing information to determine robotic instrument pose. Moreover, even if the video information is available, the addition of the kinematics information makes the computation of pose more robust. A tool tracking system is provided based on robot kinematics and vision that requires little to no modifications to the robotic instruments 101 and the preexisting surgical system 100.

Kinematics information provided by the surgical system 100 may include kinematic position $k_t^P$, kinematic orientation $k_t^\Omega$, kinematic linear velocity $\dot{k}_t^P$, and kinematic angular velocity $\dot{k}_t^\Omega$ of one or more robotic instruments 101. The kinematics information may be the result of movement of the robotic surgical arm 158, the robotic instrument 101, or both the robotic surgical arm 158 and robotic instrument 101 at a given time. The kinematics information provided by the surgical system 100 may also include the kinematic position $k_t^P$, kinematic orientation $k_t^\Omega$, kinematic linear velocity $\dot{k}_t^P$, and kinematic angular velocity $\dot{k}_t^\Omega$ of the endoscopic camera to provide a frame of reference.

Referring now to FIG. 6A, a functional block diagram of a tool tracking architecture and methodology for a surgical system is illustrated in accordance with embodiments of the invention. The main operational stages of tool tracking are illustrated in the middle column of FIG. 6A. Key technical capabilities associated with tool tracking are illustrated in the left column of FIG. 6A but for operational constraints 601. The end results of the tool tracking methodology are illustrated in the right column of FIG. 6A.

The key technical components of the methodology and architecture may be further categorized into basic building blocks and supporting blocks. The basic building blocks including image matching 609 and a state-space model 613 that are used to provide efficient tool tracking, each of which are responsive to visual information. The supporting blocks include model-based synthesis 611, adaptive fusion 615, and sequence matching 607 to support the implementation of robust and accurate tool tracking.

Adaptive fusion 615 fully explores prior information that may be available, including prior kinematics information and prior visual information.

In a robotic surgery system, vision information and kinematics information are typically available with known characteristics. Robot kinematics information is usually stable and often accurate but may drift during long periods of time. Vision-based information is very accurate when it can be reliably estimated. Otherwise vision-based information may be very inaccurate.

In embodiments of the invention, adaptive fusion is used to obtain accurate information fusion from different sources of information as well as similar sources of information. With adaptive fusion, if the vision-based information is known to be accurate then the information fusion is heavily biased towards the vision-based information. If the vision-based information is known to be unreliable or inaccurate, robot kinematics information is used over the vision-based information to generate a more robust fusion of information. While the quality of robot kinematics is typically uniform, the quality of vision information in terms of image matching and 3D post estimation varies a lot. View geometry statistics may be used to determine the reliability and accuracy of video-based information. Adaptive fusion may also be used to obtain accurate information fusion from similar sources of information.

Model-based synthesis is used herein to generally refer to generation or rendering of a template image for use in subsequent matching operations, and includes full synthesis, geometry only synthesis, and implicit synthesis. Full synthesis, as the name implies, is a complete synthesis of an image of the robotic instrument. For example, robotic instrument images are generated from a computer aided design (CAD) model based on its geometry and texture. Other prior information (the location/orientation of the model), not necessarily accurate, is presented along with the synthesized robotic instrument images for image matching 609. Geometry-only synthesis is the case where the geometry of the robotic instrument is used to synthesize geometry-only images (e.g., edge images). Texture of the model is not used in geometry-only synthesis. Implicit synthesis is the case where images are not actually synthesized. Instead the model (either geometry or texture or both) is implicitly used to perform image matching. For example, the geometric properties (e.g., width, length, shape) of a marker and the geometric relationship among them (e.g., markers forming a line) when available in a marker-based tracking system may be used to improve image matching.

In one embodiment of the invention, sequence matching is where objects or features in a sequence of images captured from one camera view are matched against objects or features in a sequence of images captured from a different camera view. In another embodiment of the invention, sequence matching is where objects or features in a sequence of images from a camera view are matched against objects or features in a sequence of synthesized images.

There are two main operational stages in a tool tracking system. The two main operational stages are tool acquisition 604 and tool tracking 606. Tool acquisition may also be referred to as localization herein.

The goal of the tool acquisition stage 604 is to obtain the absolute pose information (location and orientation) of the one or more robotic instruments within the field of view of one or more cameras, such as the stereo endoscopic camera 101C. The tool acquisition stage 604 performs a locating function 614 resulting in the location and orientation of the tool.

The goal of the tool tracking stage 606 is to dynamically update the absolute pose (location and orientation) of a moving robotic instrument. The tool tracking stage 606 may perform a full-tracking function 616 or a kinematics-tracking (pose prediction) function 618 respectively resulting in either a full-tracking state when both visual information and robot kinematics information are available or a kinematics-tracking state when visual information is not utilized (e.g., tool outside the field of view or occluded).

The mode/stage of the tool tracking system changes from tool acquisition to tool tracking after the tool is initially located within the field of view. Provided that the tool remains in the field of view, the tool tracking system may remain in the tool tracking mode/stage. However, the tool tracking system may change from a tool tracking mode/stage into a tool acquisition mode/stage if the tool is removed from the field of view and then returns into the field of view. The tool tracking system may optionally begin operation with an initialization procedure if there is only a single tool in the field of view. If additional tools are to be tracked, the optional initialization procedure may be skipped as other tools have been located and tracked. If the tools have no markers, the optional initialization procedure may involve tools moving around in order to obtain a robust localization via sequence matching.

The methodology of the tool tracking is now further described with reference to FIG. 6A which starts at block 600 and goes to block 602.

At block 602, an optional initialization of the tool tracking system may occur. Mono or stereo video 603 may be used in the tool tracking system and is initialized to begin generation of digital video frames of image data of the surgical site. Kinematics information 605 may also be used in the tool tracking system during initialization to form an initial pose of the robotic instrument. The kinematics information 605 may include positional information, including angular or linear information for example, from sensors located at various places along a robotic arm and the robotic instrument. The kinematics information 605 may be for both the endoscopic camera and robotic instruments such that the relationship between positional information for the robotic instruments and the camera may be determined.

Initialization begins with a single tool in the field of view without any occlusions. The system may be initialized for additional robotic instruments in the field of view. If tools have already been located and tracked and a new tool is being added, the new tool can be initialized by placing it into the field of view with the previously located and tracked tools. If no tool has been located and tracked, each tool may be initialized by placing it within the field of view with all other tools outside the field of view. The robotic instrument being initialized may be placed in the center of the surgical site for optimal estimation across the whole space or as close to stereo endoscopic camera 101C as possible that will allow for accurate stereo computation. With a markerless system, the robotic instrument may be moved and rotated for reliable sequence matching.

At block 604, the tool tracking system enters a tool acquisition stage/mode in the surgical site. FIG. 9B graphically illustrates the tool acquisition stage in a surgical site. Stereo video images 500L, 500R of the surgical site, such as illustrated in FIG. 5A, are captured by the endoscopic camera 101C, including one or more robotic instruments 101 in the surgical site. Stereo video may be used to obtain an absolute initial pose of the one or more robotic instruments 101 in one embodiment of the invention. In another embodiment of the invention, mono video may be used with kinematics information to estimate absolute initial pose (position and orientation) of the one or more robotic instruments 101. The one or more robotic instruments 101 may include painted markers 502 to assist in tool acquisition and tool tracking in the surgical site. The tool acquisition stage performs a locating function 614 resulting in the initial pose of the one or more robotic instruments 101 in the surgical site.

After the robotic instruments have been acquired, the methodology goes to block 606.

At block 606, the tool tracking system enters a tool tracking mode or stage in the surgical site. The goal of tool tracking is to update the absolute pose information (location and orientation) based on incremental and/or partial information (visual and robot kinematics). In the tool tracking stage 606, the tool tracking system is at a full-tracking state 616 when visual and kinematics information is available. If a robotic instrument is not visible (e.g., tools inside an organ or occluded by other tools) in the surgical site, the tool tracking system is at a kinematics-tracking state 618 for estimating tool pose.

The tool tracking system may transition from tool tracking 606 and return to tool acquisition 604 if a tracked tool gets out of field of view and then comes back into the field of view of the camera.

Figure 6B:
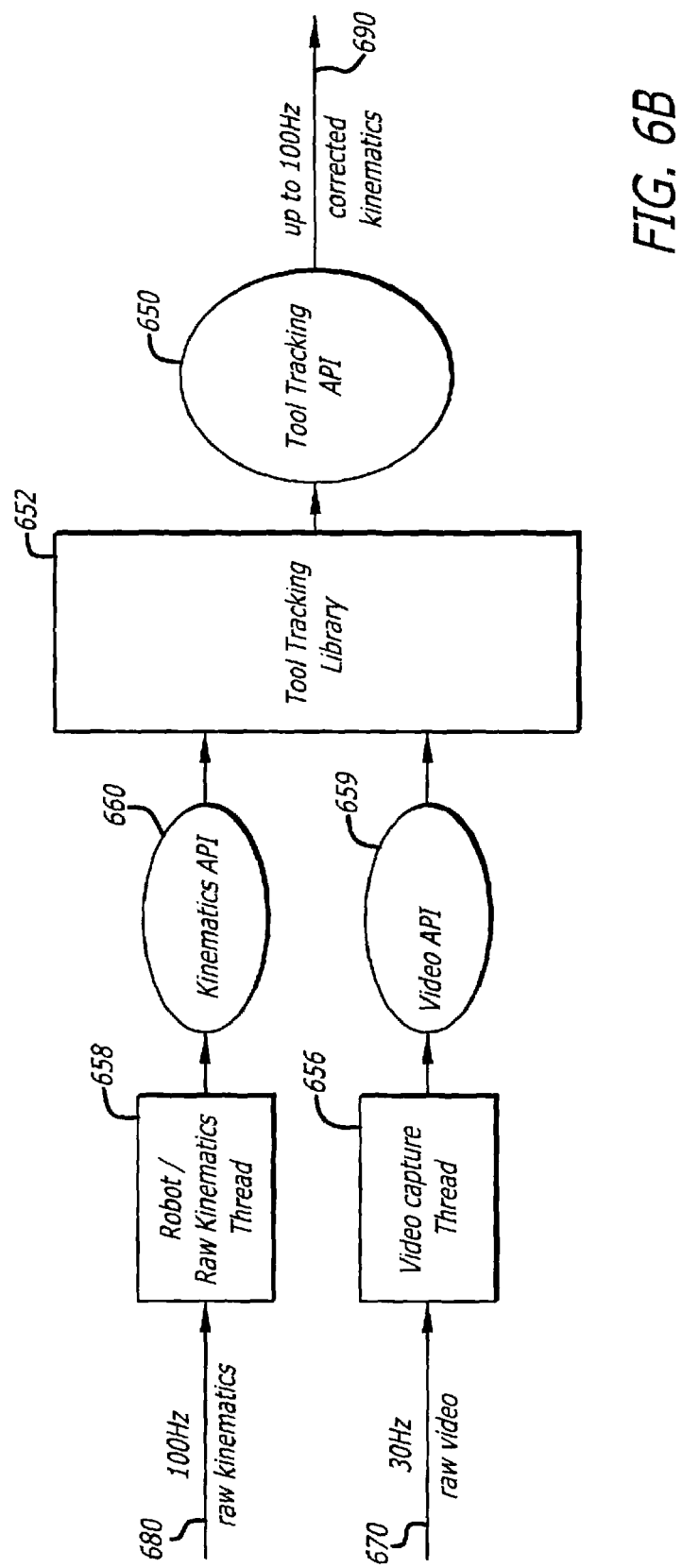
FIG. 6B is a flow chart of a tool tracking library and its application.

Referring now to FIG. 6B, a flow chart of a tool tracking library and its application is illustrated. A tool tracking application 650 is executed by a system 351 of the robotic surgical system 100. The video board 218 illustrated in FIG. 2 may be a part of the IGS system 351 in order to receive the video images from the endoscopic camera over the surgical site. A kinematics application programming interface (API) 660 provides a software interface to receive the raw kinematics data from the surgical system 100. The kinematics API 660 couples the kinematics information to the tool tracking application 650 and a tool tracking library 652. The raw kinematics data 680 is received by an API streamer thread 658 which provides the physical interface to a communication channel (for example, fiber optic cable or Ethernet, and may buffer the raw kinematics data by storing it into a memory, a hard disk, or other data storage device). The tool tracking library 652 may issue data requests to the API streamer thread 658.

A video capture thread 656 is coupled to the endoscopic camera to receive the raw endoscopic video feed 670. The raw video 670 may be mono video of a single channel or stereo video of left and right channels. The video capture thread 656 may buffer the raw video data by storing it into a frame buffer memory, a hard disk, or other data storage device. A video application programming interface (API) 659 provides the software interface to receive the raw video data from the surgical system into the tool tracking system. The tool tracking library 652 may issue data requests to the video capture thread 656.

The tool tracking library 652 contains the core functionality of combining kinematics (through kinematics API 660) and video (through video API 659) for accurate tracking of tools. The library also provides application program interface so it can be invoked in a certain way by a customer-designed tool tracking application 650

In response to the video data and the kinematics data, the tool tracking library 652 generates corrected kinematics data for the pose of a robotic instrument. The raw kinematics data is corrected for orientation and position of the tools. The corrected kinematics data may be used in a number of applications, such as image guided surgery.

As shown in FIG. 6B, the speed of raw kinematics 680 may be 100 to 200 Hertz (Hz) and the speed of raw video 670 may be 30 Hz to 60 hz and the speed of tool tracking maybe even slower. However, the speed of the corrected kinematics 690 should be substantially similar to the speed of the raw kinematics 680 for medical applications. To maintain the speed in the kinematics information, the raw kinematics may be passed through. A correction matrix (rotation and translation) may then be used to correct the raw kinematics information from the tool tracking library. Alternatively the corrected kinematics 690 may be directly output from the tool tracking library 652 where a correction matrix is applied to the raw kinematics. Either way is feasible because the correction matrix corrects the bias in the raw kinematics and the bias changes slowly, for example, slower than 1 Hz.

Algorithm Architecture to Address Natural & Technical Challenges

Figure 7:
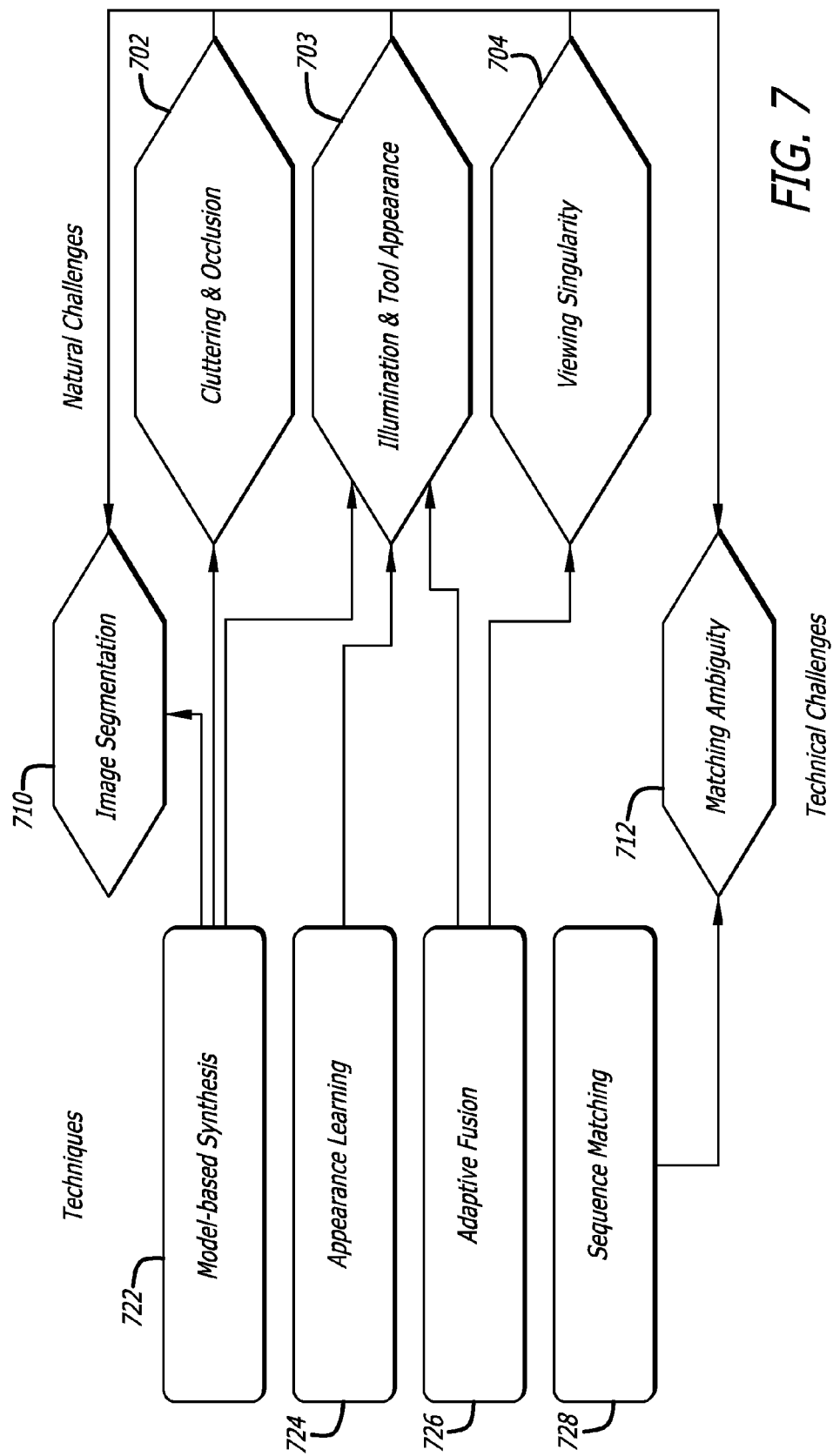
FIG. 7 is a block diagram illustrating various techniques that may be combined together to meet the challenges in tool tracking.
Figure 8:
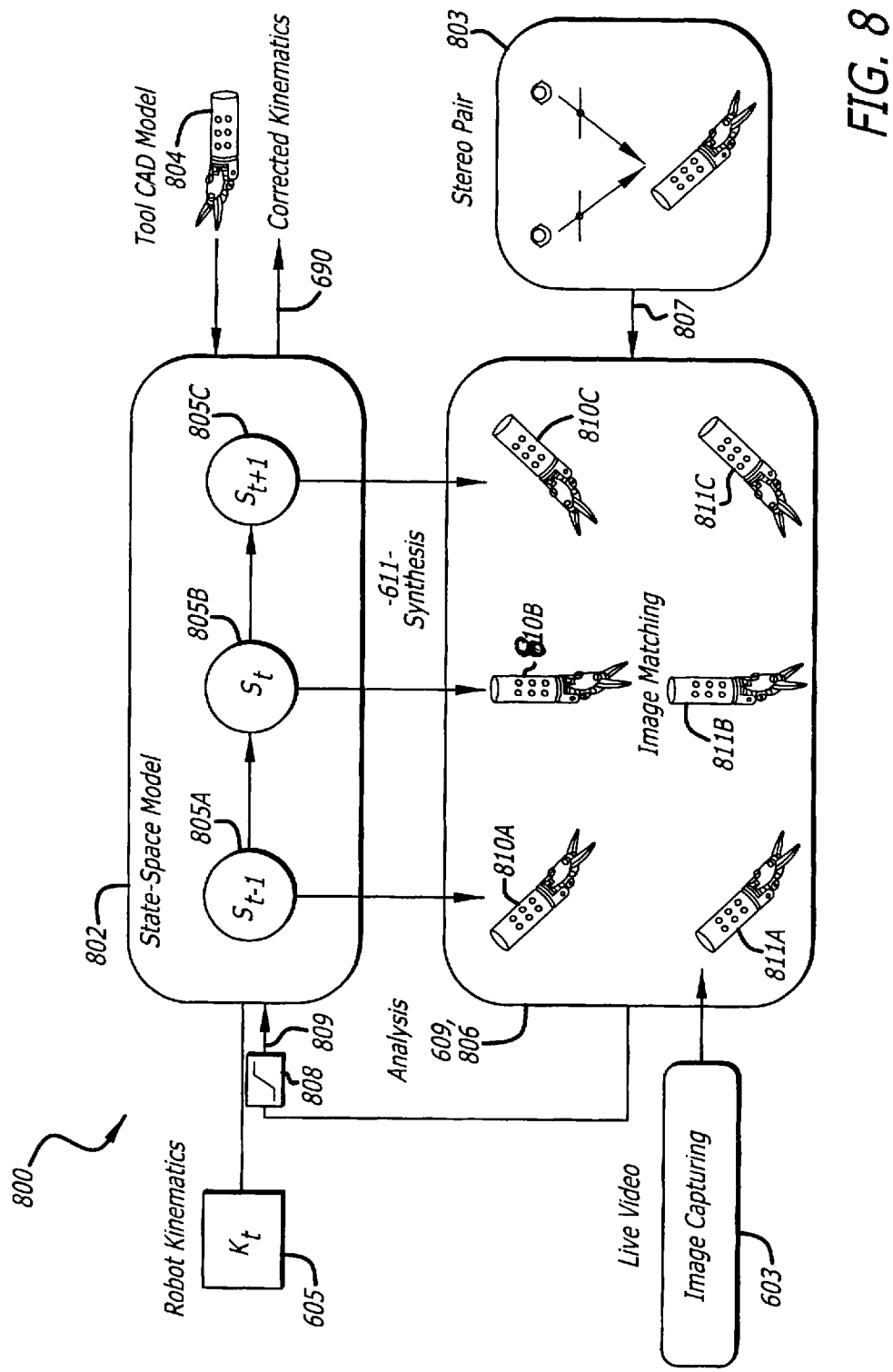
FIG. 8 is a functional flow-chart of a tool tracking system.

Reference is now made to FIGS. 6A, 7, and 8. FIG. 6A, described previously, illustrates a functional block diagram including operational stages of a tool tracking system. FIG. 7 is a block diagram illustrating the challenges of performing tool tracking. FIG. 8 graphically illustrates a functional block diagram of a tool tracking system 800.

Referring now to FIG. 8, the tool tracking system 800 adaptively fuses visual information and robot kinematics in order to achieve robust, accurate and efficient tool tracking. The unknown full pose of a robotic instrument, at a time instant t, is represented as a state $s_t$ 805B in a Bayesian state-space model 802. The state-space model 802 may use a plurality of posed states 805A-805C to perform tool tracking in the surgical site. The state-space model 802 may generate the corrected kinematics information 690 of the robotic instrument. A CAD tool model 804 (geometry only or both geometry and texture) is used for synthesizing (explicitly or implicitly) an image under a given pose (i.e. state).

For updating the state information of a robotic instrument, the relative robot kinematics $\dot{k}_t$ 605 (where the dot above the k being used to represent that the relative or first-derivative measurements of the kinematics information) between time instances t to t+1 can be coupled into the state-space model 802. Visual information 603 from captured images may be amplified and analyzed by an amplifier/filter 808 to control the influence of visual feedback 809 on the fusion of visual information and kinematics information. The amplifier/filter 808 generally implements how view geometry statistics are applied for adaptive fusion. If stereo images 803 are available, the spatial constraints 807 between left and right image pairs may also be explicitly or implicitly explored to assist in tool tracking.

As illustrated in FIG. 7, there are natural challenges and technical challenges to provide tool tracking. The natural challenges are those imposed by realistic operational scenarios. The technical challenges are those caused by proposed tool tracking algorithms when facing natural challenges. The natural challenges for example include cluttering and occlusion 702, illumination variation and image appearance change 703, and viewing singularity 704. The technical challenges include image segmentation 710 and matching ambiguity 712, for example.

The natural challenge of illumination and image appearance 703 is where the same scene changes dramatically along with the motion of directional light sources. For endoscopic operations, the image intensity of the same object can be different, depending on the distance of the object from the lighting source and the angle between the lighting source and local surface normal. This makes image-based processing less reliable. In addition, specularities from organs, blood that under directional endo-illumination make image processing more challenging.

The natural challenge of viewing singularity 704 may occur when three dimensional geometry information is derived from two dimensional images. Three dimensional geometry information derived from two dimensional images is not reliable when the two dimensional projection of a three dimensional object is degenerated. For example, a three dimensional cylindrical tool is projected onto an image plane as a circle.

The natural challenge of scene cluttering and occlusion 702 is the case where there could be more than one robotic instrument in the field of view. Additionally, the robotic instruments may be partially or fully submerged with complex and dynamic background of organ tissues, blood and smoke caused by electro-dissection.

As previously mentioned, the technical challenges include image segmentation 710 and matching ambiguity 712. Moreover while efficiency is of concern, a big technical challenge for tool tracking may be reliability and accuracy under realistic situations.

Consider now for example, pure image segmentation 710, i.e., segmentation of tools from a 2D image only, is a challenging task when the background is cluttered and/or objects are occluded. To handle this particular technical challenge, prior information is explored as a known robotic instrument is being tracked. More specifically, model based synthesis techniques 722 may be used. With model based synthesis 722, a CAD model of a robotic instrument may be used to render a clean tool image as a pattern to match against or search within a limited region constrained by the pose information of tool. As a result, pure image segmentation from the real images is avoided. Because the states of all robotic instruments are tracked, mutual occlusions of all these robotic instruments can be calculated thereby making image matching more reliable.

Another technical challenge in tool tracking, especially markerless tool tracking, is the matching ambiguity of a pair of images 712, either between left and right images or between real and synthesized images. Fundamentally, many areas in an image look alike and non-corresponding areas of two images may appear to be more alike than two corresponding areas (for example, due to illumination variations), making region-based matching ambiguous. To reduce such ambiguity, sequence matching 728 may be applied where a sequence of images will be matched against another sequence of images. Such a method is useful when we use robust and accurate relative kinematics information $\dot{k}_t$.

For example, consider a sequence of three real images 811A-811C. $[I_{t-1}, I_t, I_{t+1}]$ and three corresponding states 805A-805C $[s_{t-1}, s_t, s_{t+1}]$. For each state, one image can be rendered such that a sequence of three synthesized images $[I^S_{t-1}, I^S_t, I^S_{t+1}]$ may be formed. Under a regular analysis-by-synthesis scheme, the real images $I_t$ and the synthesized images $I^S_t$ are compared. The difference determined by the comparison is used to update the corresponding state $s_t$. For a three-state sequence, three independent computations are used to update three states. Now if we use sequence matching 728 for the same three-state sequence, the situation changes significantly. For ease of explanation, suppose that the perfect or error-less relative kinematics information is a two-sequence $$[\dot{k}_{t-1}, \dot{k}_t]$$

of kinematics information. This suggests that there is only one unknown (any one of the three states) for the three-state sequence $[s_{t-1}, s_t, s_{t+1}]$ because $s_t = s_{t-1} + \dot{k}_{t-1}$. With one known state of kinematic information, the respective sequence of three images 811A-811C. $[I_{t-1}, I_t, I_{t+1}]$ and the respective sequence of three synthesized images $[I^S_{t-1}, I^S_t, I^S_{t+1}]$ may be used to determine the unknown states. That is, if we know any one of the three states in the three-state sequence [$s_{t-1}$, $s_t$, $s_{t+1}$], we can obtain other missing states through perfect or error-less relative kinematics.

The sequence of five real images 811A-811C. [$I_{t-1}$, $I_t$, $I_{t+1}$] and the sequence of three synthesized images [$I^S_{t-1}$, $I^S_t$, $I^S_{t+1}$] are then compared to determine a difference to update the current state $s_t$ so that its underlying kinematics information is more accurate and reliable for use in tool acquisition and tool tracking. Thus, sequence matching 728 can provide a more robust and more reliable matching as the number of unknowns is reduced and the same number of observations (real images) are kept.

Additionally, appearance learning techniques 724 may be used to handle image or appearance changes 703 such as from illumination variations and natural wear of a tool, for example. Generally, appearance learning techniques handle appearance changes by training the tool tracking system on image samples of the same tool under different viewing conditions. Appearance learning techniques have been used extensively in object tracking to handle appearance change due to illumination variations. For example, parametric models have been built to handle illumination variations. Appearance learning techniques are further illustrated herein with reference to FIG. 14 with the use of face images instead of tool images.

Moreover, adaptive fusion techniques 726 may be used to handle the challenges of singularity of viewing geometry or viewing singularity 704. The technique of adaptive fusion is used to explore the available pose information, i.e., predicted state (before correction) when feeding geometric information derived from video into the Bayesian state-space model 802. More specifically, video-derived information has much less weight when fused with robot kinematics information under such conditions. In a Bayesian state-space model 802, this manifests itself as large noise variance in the observation equation.

Adaptive Fusion of Vision and Kinematics

Adaptive fusion may be used to handle the challenges of singularity of viewing geometry in order to provide robust and accurate kinematics information of the tools in a surgical, medical, or other type of robotic system.

Analysis-by-Synthesis for Tool Localization

Pure image segmentation may be used by a tool tracking algorithm to localize tools. Pure image segmentation of tools from a two dimensional image is straightforward if the tools have distinctive features, such as color marks that may be used to identify a tool. However, operational conditions may make pure image segmentation techniques difficult if not impossible to perform.

Referring now to FIG. 9A, an image has a tool 901 hidden by an occlusion 902. The occlusion 902 is so severe that it breaks key steps (e.g., color- and/or shape-based analysis) of pure image segmentation of the image such that the tool 901 cannot be found therein. The tool shape 901S is substantially covered over by the occlusion shape 902S in the image illustrated in FIG. 9A. In the case of markerless tool tracking where the tools have no markings, an occlusion can only make it more difficult for pure image segmentation techniques to localize a tool.

Referring now to FIG. 9B, the image of the tool 901 is again hidden by an occlusion 902. Techniques of sequence matching and/or model-based-synthesis matching may be used to localize the robotic instruments instead of pure image segmentation. Sequence matching was briefly discussed previously. Model based synthesis uses a priori knowledge regarding kinematics and appearance that may be available for the tools that are being tracked.

With model based synthesis, a CAD model 904A of the tool 901 is used to synthesize an image of the tool given the known or hypothesized pose information for the tool. The pose information for the tool may be determined from kinematics information or otherwise and a posed synthesized image 904B may then be generated. The posed synthesized image 904B of the tool 901 may then be used to perform image matching or an image search within the overall image of a surgical site to find the location of the tool 901 therein even though it may be partially occluded. This technique of tool localization may generally be referred to herein as an analysis-by-synthesis approach. Using the synthesized 904B image as a pattern to search for the tool 901 within an image of the surgical site helps overcome the difficulty of an occlusion 902 that may cover the tool 901. Tool image fragments 901' left over after the occlusion 902 is subtracted from the tool image is sufficient to use to determine tool localization. However if the occlusion 902 completely covers over the tool 901, image analysis alone cannot localize tools.

Alternatively in another embodiment of the invention, image segmentation may be guided by exploring the available prior kinematics and image information. That is, image segmentation may be constrained to be performed within a limited region of the image of the surgical site based on rough pose information of the tool in response to the prior robot kinematics and the CAD model 904A of the tool 901. This technique of tool localization may generally be referred to herein as aided image segmentation in contrast to pure image segmentation that has no constraints.

Image Synthesis and Image Analysis/Search

Figure 9C:
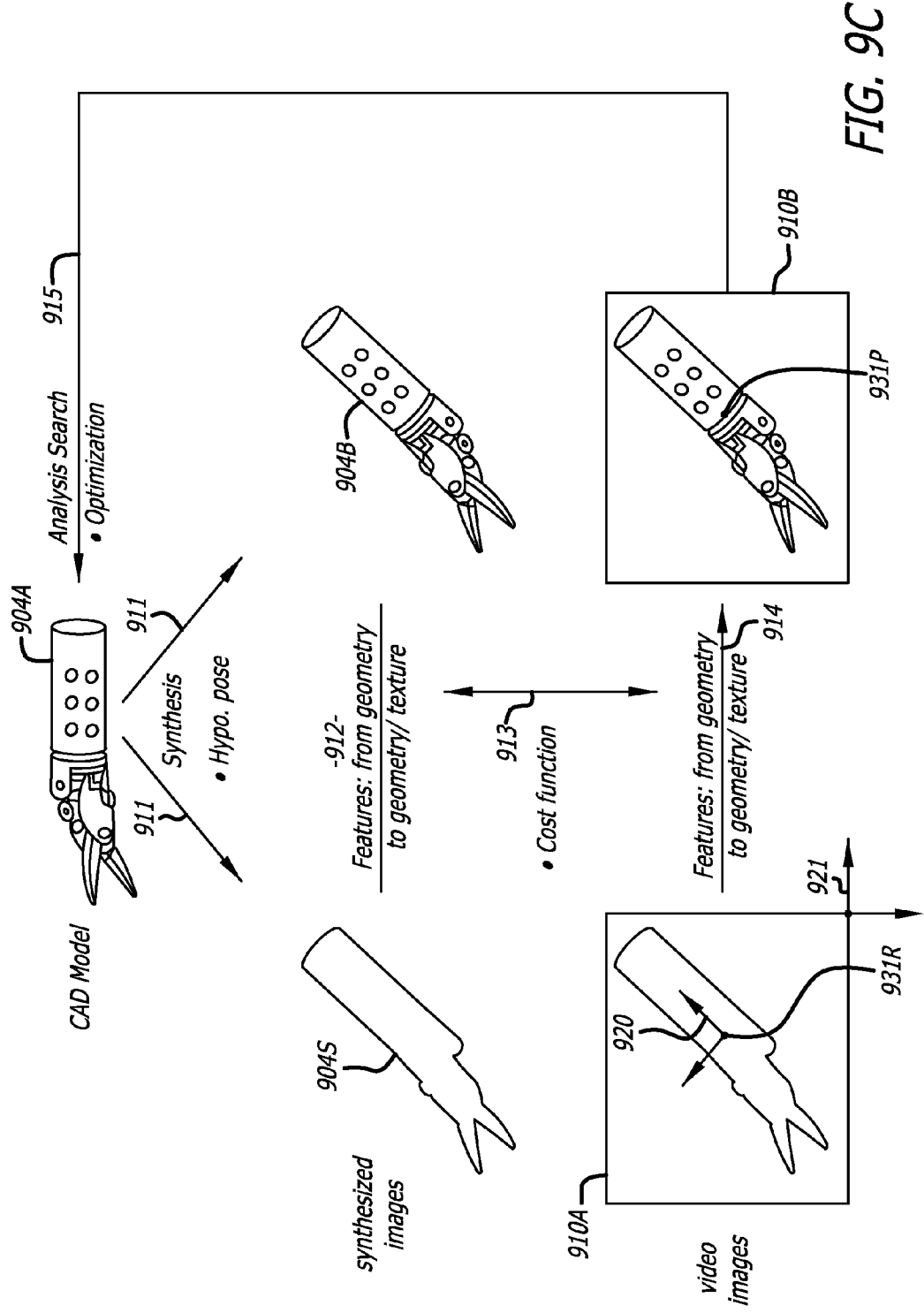
FIG. 9C is a more detailed figure to illustrate the process of model-based synthesis to localize a tool within an image.

Referring now to FIG. 9C, image synthesis (also referred to herein as model-based synthesis) and image analysis/search are key steps in using analysis-by-synthesis methods for tool localization and tool tracking. The image synthesis 911 and image analysis/search 915 processes may be repeatedly performed in an iterative optimization approach to find the best tool pose parameter in response to a given cost function CF 913. With an iterative optimization approach, an initial pose hypothesis may be formulated to generate the initial synthesized model tool for computation of an initial cost function. The cost function CF 913 is a function of what corresponding features 912,914 are used for matching and how an image is synthesized during image synthesis 911. For example, a synthesize edge image 904S of the tool may be synthesized during image synthesis 911 in response to the CAD geometry of the CAD model 904A of the tool. Alternatively, a synthesized regular image 904B of the tool may be synthesized during image synthesis 911 in response to the CAD geometry and CAD texture of the CAD model 904A of the tool. The synthesize edge image 904S of the tool may be used to perform image matching with edges in a video image 910A of the tool. The synthesized regular image 904B of the tool may be used to perform image matching with a regular video image 910B of the tool. If the appearance of the tool has changed in the images, e.g., 910B, appearance learning may be used to augment the analysis-by-synthesis process for tool localization and tool tracking. Note that an edge image, such as illustrate in video image 910A, is typically robust against lighting variations.

With a synthesized tool image $I^s$ being synthesized in response to a given tool pose in the camera coordinate system and the CAD model $\hat{I}$ (with geometry 1 g and texture $\hat{I}_t$); the synthesis process may be expressed by an equation as $$I^s[x] = L(M_t[\Phi;(P,\Omega,M_g)]) \quad \text{(Eq. 1)}$$

where x=[x, y] is the image coordinate and $\Phi$ is the homogeneous camera geometric projection from three dimensions (3D) into two dimensions (2D). Thus, the model texture $\hat{I}_t$ can be mapped to the coordinate of image $I^s[x]$ as a function of the homogeneous camera geometric projection $\Phi$ and a combination of tool pose (position P and orientation $\Omega$ of the tool), and the geometry $\hat{I}_g$ of the tool model. For presentation clarity, we omit the nonlinear mapping step from the 2D homogeneous coordinates $[x_w, y_w, w]$ after $\Phi$ projection to 2D inhomogeneous image coordinates $$\psi: [x,y] = [x_w/w, y_w/w]. \quad \text{(Eq. 1A)}$$

In an example image synthesis pipeline, the model will be decomposed into triangles, the 3D vertex coordinates of which will be described in a coordinate system attached to the model. The model coordinates will first be transformed to a world coordinate system, before being projected to a 2D display coordinate system by applying the camera model. Once in the 2D display coordinate system, each triangle will be rasterized. The synthesis of the final per-pixel color values may be computed via interpolation of color specified on a per-vertex basis, texture mapping and filtering, and the application of lighting models. (Reference: Computer Graphics: Principals and Practice, by James D. Foley, Andries van Dam, et. al, Addison-Wesley Professional; 2 edition, Aug. 4, 1995, ISBN: 978-0201848403).

The function L is a mapping function that maps the model texture $\hat{I}_t$ into the real image/appearance $I^s[x]$ because the real image varies with lighting conditions and other factors, such as occlusions.

The tool pose may be represented by the position $P=[P_X, P_Y, P_Z]^T$ of a chosen reference point 931R (e.g., the control point before the tool wrist) and the orientation $\Omega$ of its local coordinate system 920 originated in the reference point 931R with respect to the camera coordinate system 921. Camera coordinates of a 3D point 931P on the tool that maps to x may be represented by $[X,Y,Z]^T$. A local coordinate of the 3D point 931P on the tool that is internal to the tool model may be represented as $[X_M, Y_M, Z_M]^T$. A transformation $T_{\{P,\Omega\}}$ of the local coordinate of the 3D point 931P on the tool to the camera coordinate of the tool as a function of the tool pose may be written as $$[X,Y,Z,1]^T = T_{\{P,\Omega\}} [X_M, Y_M, Z_M, 1]^T \quad \text{(Eq. 2)}$$

where $T_{\{P,\Omega\}}$ is a four by four 3D-to-3D rigid transformation matrix that can be further decomposed into translational and rotational parts.

After image synthesis of the synthesized tool image $I^s$, an image analysis or image search is performed to find the best estimate of the tool pose. Mathematically this is an optimization problem that may be written in equation form as $$T^*_{\{P,\Omega\}} = \arg\min_{T_{\{P,\Omega\}}} C(I^s, I), \quad \text{(Eq. 3)}$$

Where C is a cost function of comparing images. The synthesized tool image $I^s$ may be repeatedly generated in an iterative manner using updated pose information so that the cost function C of comparing the synthesized tool image $I^s$ with the video images of the surgical site are minimized and the tool pose is optimized.

One of the simplest cost functions is a sum of squared differences (SSD) that may be used to compare the synthesized tool image $I^s$ with the video images of the surgical site. However even though an SSD is a simple cost function, it is nonlinear (e.g., higher than quadratic) in terms of the pose parameters due to the camera geometric projection $\Phi$ that is nonlinear and the mapping function L to map model texture to real image/appearance that varies with lighting conditions that may be non-linear. Minimizing a nonlinear cost function C is a complex optimization problem.

Different strategies can be applied to solve a problem of minimizing a nonlinear cost function C. For example, random optimization methods may be used to solve and minimize a nonlinear cost function C problem in order to avoid an exhaustive parameter search. On the other hand, a quadratic approximation of the cost function may be use to iteratively solve the nonlinear problem.

In one embodiment of the invention, the complex optimization problem may be broken up into two different steps to more efficiently minimize the cost function C. The first step entails performing an image matching where the raw image pixels or extracted image features of I are used for matching against those of the respective synthesized tool image $I^s$. The second step involves performing a geometry-only optimization in response to the result of the image matching between the raw image pixels or extracted image features and corresponding ones from the respective synthesized tool image $I^s$. Mathematically, these two steps to solve the optimization problem of Eq. 3 may be formulated into the following two equations:

$$(\{x^m, X^m\}) = \arg\min_{(x,X)} C(I^s, I), \text{ for a given } T_{\{P,\Omega\}} \quad \text{(Eq. 4)}$$

and the best $T_{\{P,\Omega\}}$ is determined as $$T^*_{\{P,\Omega\}} = \arg\min_{T_{\{P,\Omega\}}} \sum (x^m - f(X^m))^2. \quad \text{(Eq. 5)}$$

Eq.4 represent the step of finding the corresponding 2D feature points $x^m$ from I and 3D points $X^m$ on the tool via image matching of $I^s$ and I. Eq. 5 represents the geometry-only optimization where optimal 3D-2D mapping $T_{\{P,\Omega\}}$ can be found given the matched 2D-3D pairs. The function f( ) is a nonlinear function in the following form $\psi(\Phi T_{\{P,\Omega\}})$.

In cases where the initial pose hypothesis is not close to the true pose or in case where it is desirable to obtain a very accurate pose estimate, the foregoing steps to solve the optimization problem (Eqs. 4 and 5) combined with the synthesis step (Eq. 1) can be repeated in an iterative procedure.

The image matching and analysis-by-synthesis processes may be incorporated into a sequential framework for fusion of vision and kinematics information to obtain more accurate positional information of a tool than would otherwise be available from each alone.

Appearance Learning

Referring now to FIG. 14, a diagram illustrating appearance learning of objects within an image is illustrated. As discussed previously, appearance learning techniques may be used to handle image and appearance changes, such as from illumination variations and natural wear of a tool, for example. The appearance variations due to changes in illumination may exhibit illumination subspace/cone phenomena or spherical harmonics for example. Appearance learning techniques generally train the tool tracking system on image samples of the same tool under different viewing conditions. Pose specific learning techniques may be used as well as clustering or manifold learning techniques may be used to train the tool tracking system over a large number of samples.

In FIG. 14, basis images for illumination variations 1401A, 1401B, 1401C may be used to train the tool tracking system to generate one or more synthesized images 1402A-1402B which are more closely matched to the respective real images 1045A-1405B that may be captured under different lighting conditions.

Appearance learning techniques have been used extensively in object tracking to handle appearance change due to illumination variations (reference: G. Hager and P. Belhumeur, "Efficient Region Tracking with Parametric Models of Geometry and Illumination," IEEE Trans. Pattern Analysis and Machine Intelligence, Vol. 20, pp. 1025-1039, 1998). For example, parametric models have been built to handle illumination variations (reference: H. Murase, S. Nayar, "Learning and Recognition of 3-D Objects from Brightness Images," Proc. AAAI Fall Symposium, Machine Learning in Computer Vision, pp. 25-29, 1993.

Sequential Adaptive Fusion of Vision and Kinematics

After image matching, such as through analysis-by-synthesis for example, the next step to obtain more accurate positional information is the fusion of image positional information and kinematics positional information of the robotic instruments. In general, the purpose of information fusion is to provide more robust and/or more accurate positional information for the robotic instruments in the surgical site such that tool tracking information may be applied in various ways to obtain accurate results, e.g., measurements of certain physical entities within a surgical site. Key to successfully fusing information together from similar sources or from different sources is determining how to adjust the contributions of each to the fusion. The contribution of sources to the information fusion may be adjusted in different ways, such as by a winner-take-all or a weighted averaging method, for example.

Ideally, all sources of information should be fused together so that the information fusion constantly provides the best accuracy and the most robust tool tracking. However due to the dynamic nature of systems, there typically is a trade-off between accuracy and robustness in information fusion. As a result of the tradeoffs, the typical practical approaches to information fusion tend to have compromised results.

State-Space Model for Incorporating Vision and Kinematics

Figure 10B:
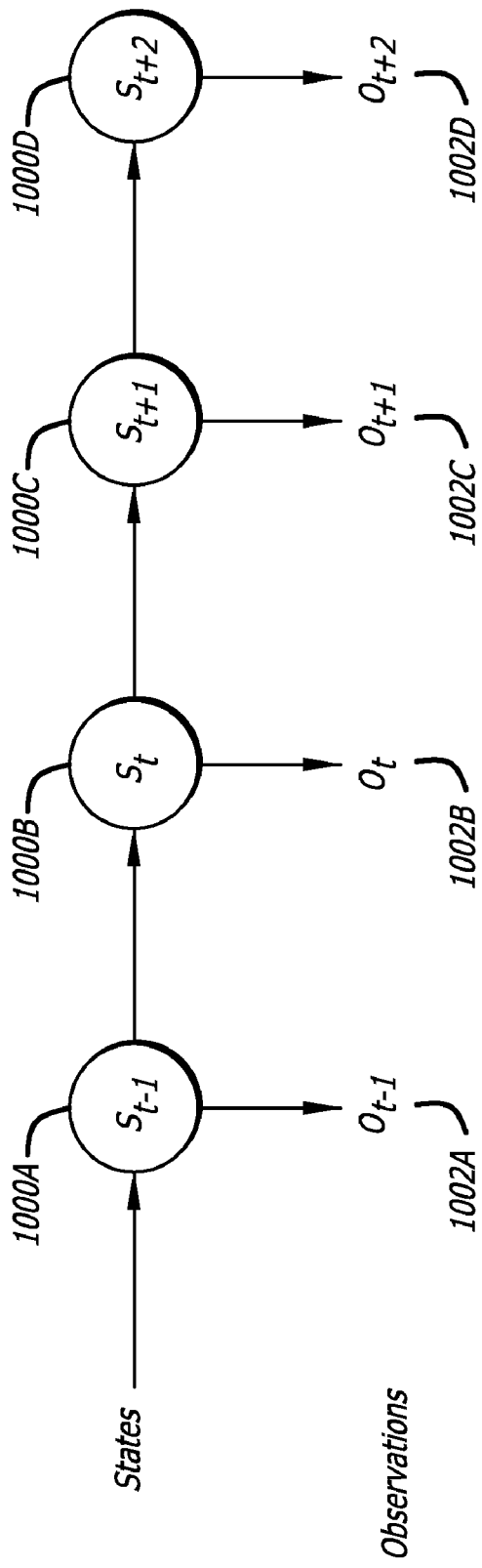

Referring now to FIGS. 10A-10B, a state-space model is now described to adaptively fuse together robot kinematics information and vision-based information. Both raw robotic kinematics information 1010 of the robotic instrument and vision-based information 1101 can be used to generate the state variables 1000A-1000D. A tool model 804 may be used to synthesize 611 the synthesized images 810 in response to the state variables 1000A-1000D. An image analysis 806, 609 is performed comparing the synthesized images 810 of the robotic instrument with the observed images 1101.

Some real-world data analysis tasks involve estimating unknown quantities from given observations. Moreover, a priori knowledge about phenomenon of a number of applications may be available to allow us to formulate Bayesian models involving probability and statistics.

The unknown quantities of information fusion at corresponding time instances can be defined as state variables 1000A-1000D (of the system) and a Markov chain model can be assumed among states at different time instances, then a state-space model may be formed. The state-space model may include 1) a dynamic/state model that relates state variables 1000A-1000D at different time instances (t−1, t, t+1, t+2) and 2) an observation model that relates state variables S 1000A-1000D to observations O 1002A-1002D. In the case of Gaussian noise, the state-space model (a discrete version is shown—a continuous version is similar and involves temporal integration) may be described by the following set of mathematical equations, $$\begin{cases} \text{Initial estimate} & s_0 \\ \text{Dynamic model} & s_t = Ds_{t-1} + v_t \\ \text{Observation model} & o_t = Hs_t + w_t \end{cases} \quad \text{(Eq. 5A)}$$

Where D and H are the dynamic matrix and observation matrix respectively. $v_t$ and $w_t$ are respectively the dynamic noise and the observation noise that have Gaussian distributions $N(\mu_s, C_d)$ and $N(\mu_o, C_o)$ respectively. $C_d$ and $C_o$ are covariance matrices for dynamic model and observation model respectively.

State-space models have been used in many disciplines of science and engineering, and may be referred to by different names such as Bayesian filtering, optimal filtering, stochastic filtering, on-line inference, for example.

If the state-space model is linear and the modeling noises of the system are Gaussian, then a substantially exact analytic expression can be derived to solve the on-line estimation problem for the state variables of information fusion. In this case, the analytic expression that is well-known and widely used is a Kalman filter (see R. E. Kalman, "A New Approach to Linear Filtering and Prediction Problems," Trans of the ASM—Journal of Basic engineering, Vol. 82, pp. 35-45, 1960.). In the case of a non-linear system and Gaussian noise, Extended Kalman Filtering (EKF) (reference: Greg Welch and Gary Bishop, An Introduction to Kalman Filter, Dept. Computer Science Tech Report 95-041, University of North Carolina, updated 2006.) can be applied where the non-linear system is approximated by linearizing the models (either non-linear dynamic model or non-linear observation model or non-linear both) based on previous estimate and applying Kalman filtering.

However, for more complex problems that do not obey linear model and Gaussian noise assumption, a set of more general methods are required. The general method for estimating the state variables is often referred to as Sequential Monte Carlo (SMC) methods (reference: J. Liu and J. R. Chen, "Sequential Monte Carlo Methods for Dynamic Systems," Journal of American Statistical Association, Vol. 93, pp. 1032-1044, 1998. In SMC methods (also referred to as particle filter), states are represented by posterior probability density function (pdf) and sampling techniques are used to generate the posterior probability density function (pdf).

In a number of embodiments of the invention, a state-space model based approach is used to adaptively fuse robot kinematics and vision information. In the following discussion, s represents a state vector of the states 1000A-1000D. In practice, s may be a vector version of the matrix $T_{\{P,\Omega\}}$ (Eq. 1), or a collection of point positions $[X, Y, Z]^T$, etc., that are equivalent in theory but may be chosen based on a particular application.

Respective velocity information may be readily added to the state space model by taking the first derivative of the positional information.

Without any loss of generality, consider for example position P and orientation $\Omega$ and first derivatives $\dot{P}$ and $\dot{\Omega}$ of a robotic instrument. Position and velocity may be represented mathematically as $$\begin{cases} \text{Position} & P = [P_X, P_Y, P_Z]^T \\ \text{Linear Velocity} & \dot{P} = [\dot{P}_X, \dot{P}_Y, \dot{P}_Z]^T \end{cases} \quad \text{(Eq. 6)}$$

The orientation and angular velocity of the robotic instrument may be represented mathematically using unit quaternion for its minimal-style representation and operation efficiency as $$\begin{cases} \text{Orientation} & \Omega = [\theta_0, \theta_x, \theta_y, \theta_z]^T \\ \text{Angular Velocity} & [0, \dot{\Omega}^T]^T = [0, \omega_x, \omega_y, \omega_z]^T \end{cases} \quad \text{(Eq. 7)}$$

Combining the position and orientation vectors together, the state vector may be represented mathematically in a covariance matrix as follows:

$$s_t = \begin{bmatrix} P_t \\ \Omega_t \\ \dot{P}_t \\ \dot{\Omega}_t \end{bmatrix} \quad \text{(Eq. 8)}$$

The filter state-space model may be implemented with extended Kalman filtering (simple to implement but maybe not sufficient), unscented Kalman filtering (see S. J. Julier and J. K. Uhlmann. A New Extension of the Kalman Filter to Nonlinear Systems. In *Proc. of AeroSense: The 11th Int. Symp. on Aerospace/Defense Sensing, Simulation and Controls.*, 1997 (easy to implement and maybe sufficient)), or computationally expensive particle filtering.

Extended Kalman filtering or particle filtering may be used for tool tracking because 1) the dynamic state space model is non-linear due to the quaternion representation, and 2) the observation model is non-linear in the case of using 2D images as observations and linear in the case of using stereo-derived 3D points as observations. In one embodiment of the invention, we adopt the following nonlinear equation to model the transfer of the system from state $s_{t-1}$ to $s_t$ (Eq. 9)

$$d(s_{t-1}) = \begin{bmatrix} P_{t-1} + \dot{P}_{t-1} \\ q(\Omega_{t-1}, \dot{\Omega}_{t-1}) \\ \dot{P}_{t-1} \\ \dot{\Omega}_{t-1} \end{bmatrix}$$

where the non-linear part comes from quaternion operation $\Omega_t = q(\Omega_{t-1}, \dot{\Omega}_{t-1})$, The Jacobian matrix for Eq. 9 is as follows:

$$D = \begin{bmatrix} I_{3\times3} & 0_{3\times4} & I_{3\times3} & 0_{3\times3} \\ 0_{4\times3} & Q_{4\times4} & 0_{4\times3} & 0_{4\times3} \\ 0_{3\times3} & 0_{3\times3} & I_{3\times3} & 0_{3\times3} \\ 0_{3\times3} & 0_{3\times3} & 0_{3\times3} & I_{3\times3} \end{bmatrix} \quad \text{(Eq. 10)}$$

where $\Omega$ is a skew-symmetric matrix given by $$Q = \frac{1}{2}\begin{bmatrix} 0 & -\omega_x & \omega_y & \omega_z \\ \omega_x & 0 & -\omega_z & \omega_y \\ -\omega_y & \omega_z & 0 & -\omega_z \\ -\omega_z & -\omega_y & \omega_x & 0 \end{bmatrix}. \quad \text{(Eq. 11)}$$

Observations of Robot Kinematics and Vision

Sets of observations are available to the state space model including robot kinematics ($k_t^P$ and $k_t^\Omega$) 1010 and vision 1011. In one embodiments of the invention, image measurements, the 2D locations of featured points $x_i$, are directly used to construct the observation vector O. Such a choice make the observation equation for the vision part nonlinear due to the perspective projection of a 3D tool onto one 2D image in the case of monocular view, or left and right images in the case of stereo view.

Alternatively, vision-derived (through matching stereo image, for example) 3D points $X_{s,i}$, observations due to vision, may be used to construct the observation vector O. In such case, the observation matrix $C_o$ consists of two parts: one for kinematics (the leading diagonal sub-matrix of Eq. 12) and one sub-matrix, a covariance matrix $C_{o,v}$, for vision as follows:

$$C_o = \begin{bmatrix} \sigma_{k^P}^2 I_{3\times3} & & & & \\ & \sigma_{k^\Omega}^2 I_{3\times3} & & & \\ & & \sigma_{k^P}^2 I_{3\times3} & & \\ & & & \sigma_{k^\Omega}^2 I_{3\times3} & \\ & & & & C_{o,v} \end{bmatrix} \quad \text{(Eq. 12)}$$

In such a case, the observation equation is linear for the vision part and we can construct the observation covariance matrix $C_{o,v}$. For example, we have the following covariance matrix for the case of parallel camera setup (FIG. 12B):

$$C_{o,v} = \begin{bmatrix} C_{o,v,1} & & & \\ & C_{o,v,2} & & \\ & & \ldots & \\ & & & C_{o,v,n} \end{bmatrix} \quad \text{(Eq. 13)}$$

where the view-geometry variance matrices $C_{o,v,i}$ (for each 3D point $X_{s,i}$) are related to 1) the uncertainty (standard deviation) of matching stereo images, 2) the inverse of image resolution (for example, high-definition camera offers better accuracy than standard-definition camera), and 3) the square of the true values of $X_{s,i}$.

In a number of embodiments of the invention, first-order kinematic information (velocity information) ($\dot{k}_t^P$ and $\dot{k}_t^\Omega$) is provided that may provide an extra constraint with respect to the evolution (e.g., changes from state to state) of the dynamic system. In other embodiments of the invention, first-order vision observations may be derived by tracking image points (i.e., temporal image matching) to provide an extra constraint.

In embodiments of the invention with analysis-by-synthesis methodology, estimated states (e.g., tool poses) may be used to synthesize images for image matching against real images to establish correspondence between 3D points on the tool model and 2D points on the tool image. With visual correspondence, observation vectors may be formed for the vision-based information and the observation equation is non-linear due to the perspective projection of 3D points to 2D points.

Bundle Adjustment for Improved Results

In the case of Gaussian noises and linear systems, Kalman filtering provides a perfect sequential solution to a batch least square optimization problem. because of the Markovian assumption that given the present state future states are conditionally independent of the past states. However, tool tracking in reality is a nonlinear problem and it is often not easy to achieve an accurate solution with a sequential approach such as extended Kalman filtering. To achieve accurate results with extended Kalman filtering given a non-linear system, an iterative bundle adjustment process that combines all observations across multiple states may be used starting from initial results provided by the extended Kalman filtering 802. As a general optimization method, bundle adjustment has wide applications.

For example, bundle adjustment can be used for sequential matching to be discussed later. To given a specific example in the case of stereo image matching, we have spatial image matching across two views and temporal image matching within each image sequence. By combining all these redundant information together through bundle adjustment, we can achieve improved results compared single stereo pair based results.

Bundle adjustment, an optimization technique in photogrammetry, refers to the "bundles" of light rays leaving each 3D feature and converging on each camera center which are "adjusted" optimally with respect to both feature and camera positions (reference: C. Salma, C. Theurer, and S. Henrikson, Manual of Photogrammetry, American Society of Photogrammetry, Falls Church, 1980). A bundle adjustment problem is essentially just a large sparse geometric parameter problem that is nonlinear in nature. To implement bundle adjustment iterative procedures may be used, such as the well known Levenberg-Marqudart mathematical algorithm (see "Numerical Recipes in C: The Art of Scientific Computing", William H. Press, Saul A. Teukolsky, William T. Vetterling, Brian P. Flannery, Second edition, Cambridge University Press, 1992).

The following describes one example of applying bundle adjustment to improve the pose estimate for the problem of tool tracking.

In tool tracking, estimates of the poses of a robotic instrument are needed for the state space model. Bundle adjustment is used to optimize the estimated poses of the robotic instrument in a chosen coordinate system, e.g., the camera-centered coordinate system. That is, it is desirous to obtain the relative orientation of the tool with respect to the camera.

There are a number of ways to use bundle adjustment with the state-space model. There is a batch approach, a window-based approach, and a recursive/sequential approach to apply bundle adjustment techniques to the state space model. With a recursive/sequential approach, bundle adjustment is applied whenever there is a new observation, e.g., a new pair of stereo images (see P. McLauchlan, "The Variable State Dimension Filter applied to Surface-Based Structure from Motion," CVSSP Tech Report TR-4/99, University of Survey, 1999). Typically, some approximation is made to make the computations efficient. With a window-based approach, bundle adjustment is applied to a short sequence of states and measurements. With a batch approach, bundle adjustment is applied to all available states and measurements. Generally, a batch process approach may be best, followed by a window-based approach, and finally a recursive/sequential approach in implementing bundle adjustment with the state-space model.

For example, a batch bundle adjustment may be applied at each time instance or at selected time instances based on all the measurements and state estimates that are available from extended Kalman filtering. Applying a batch bundle adjustment in the beginning of time where the state-space model is applied may be preferred because 1) quick convergence to the correct solution to a non-linear optimization problem is desirous from the beginning, and 2) the computation is efficient because there are only a small number of states and observations available.

Image Matching

Image matching is used for incorporating vision information into the tool tracking system and its state space model. Image matching (Eq. 4) in the image analysis steps (Eqs. 4 and 5) finds the corresponding 2D feature image points and 3D points on the tool. Image matching also finds the corresponding image features between the left and right images from a stereo camera.

Image matching may be facilitated by sequence matching of a temporal sequence of frames of video images. Alternatively, image matching may be facilitated by using a 2D or 3D model of a tool and a video image. Implementation of the two dimensional image matching may alternately be performed by simple intensity-based SSD (sum of squared difference), feature-based matching (for example, a point, a scale-invariant-feature-transform feature: D. Lowe, "Object recognition from local scale-invariant features," Proc. Int. Conf. Computer Vision, 1999.), or probabilistic matching. When matching a 2D image with a 3D model synthesized image, more robust features such as edges can be used. In this case, the cost function would be the sum of distance measures from the image edge points to the closest synthesized curves/lines (reference: D. Lowe, "Fitting parameterized three-dimensional models to images," *IEEE Trans. on Pattern Analysis and Machine Intelligence*, Vol. 13, pp. 441-450.).

Image matching can be applied in different scenarios, such as temporal matching of images within sequences of images (FIG. 11A) or spatial matching of images across two stereo views (FIG. 11C). In another embodiment of the invention, real images are used to match against synthesized images in the analysis-by-synthesis approach (FIG. 11B). In another embodiment of the invention, two or more of these image matching techniques (FIGS. 11A-11C) may be used together to perform image matching. In each of these embodiments of the invention, image matching could be applied to corresponding artificial markers attached to instruments, natural image features or image appearances (e.g., instrument tips). The artificial markers are passive visual markers.

Referring now to FIG. 11A, temporal image matching of a pair of video images 1101V-1101V' is illustrated. The video image 1101V of the actual tool 101 (e.g., see FIG. 1A) is taken at time t resulting in a tool image 101V at time t. The video image 1101V' of the same actual tool 101 is taken at a different time, time t+1, by the same camera resulting in a tool image 101V' at time t+1. During the time the images are captured, the camera may be fixed with respect to the robotic surgical system while the tool 101 may move relative to the robotic surgical system.

Various aspects of the video images of the tool taken at different times may be used to perform image matching. That is one or more of a matching of markers 1110, a matching of natural features 1111, and/or an appearance matching 1112 may be performed. For example, markers 502V on the tool image 101V in the first video image 1101V of the tool 101 may be compared with the markers 502V' on the tool image 101V' in the second video image 1101V' to help determine new pose information of the actual tool 101. Besides marker image matching, other information may be used determine pose information of the actual tool 101.

Referring now to FIG. 11B, synthesis image matching of a video image 1101V and a synthesized image 1101S is illustrated. The video image 1101V of the actual tool 101 (e.g., see FIG. 1A) is taken by a camera resulting in a tool image 101V. The synthesized image 1101S of the tool 101 is generated by a computer having prior knowledge of the actual tool 101 resulting in a synthesized tool image 101S. The pose of synthesized tool image 101S in the synthesized image 1101S of the tool 101 attempts to match the pose of the tool represented by the tool image 101V in the video image 1101V at a moment in time.

Various aspects of the video image 1101V and the synthesized image 1101S of the tool may be used to perform image matching. That is, one or more of a matching of markers 1110, a matching of natural features 1111, and/or an appearance matching 1112 may be performed. For example, markers 502V in the first video image 1101V of the tool image 101V may be compared with the synthesized markers 502S on the synthesized tool image 101S in the synthesized image 1101S of the same tool 101 to help determine new pose information of the actual tool 101.

Referring now to FIG. 11C, special image matching of a left video image 1101VL and a right video image 1101VR is illustrated. The left video image 1101VL of the actual tool 101 (e.g., see FIG. 1A) is taken with a camera in a first position with respect to the tool, such as a left side, resulting in a left tool image 101VL. The right video image 1101VR of the same actual tool 101 is taken at a different position with respect to the tool, such as the right side, resulting in a right tool image 101VR. The left video image 1101VL and the right video image 1101VR are captured at substantially the same time by their respective cameras.

Various aspects of the left and right video images of the tool may be used to perform image matching. That is, one or more of a matching of markers 1110, a matching of natural features 1111, and/or an appearance matching 1112 may be performed. For example, markers 502VL on the left tool image 101VL in the left video image 1101VL of the tool 101 may be compared with the markers 502VR on the right tool image 101VR in the right video image 1101VR of the same tool to determine new pose information of the actual tool 101.

As mentioned herein, these image matching techniques may be combined to generate better pose information for the tool. For example, it is natural to combine temporal image matching (FIG. 11A) with spatial image matching (FIG. 11C) or combine temporal image matching (FIG. 11A) with synthesis image matching (FIG. 11D). However, all three techniques may be used all together or flexibly in various combinations to try and obtain the best pose information for the tool.

In another embodiment of the invention, stereo images are used to construct 3D feature points, and these 3D points can be matched (for example, through the popular iterative closest point algorithm, reference: P. Besel and N, McKay, "A method for registration of 3-D shape," IEEE Trans. Pattern Analysis and Machine Intelligence, Vol. 14, pp. 239-256, 1992) against corresponding 3D points, for example, markers, on the robotic instrument. Before we have stereo-derived 3D points, we need to apply a two-step approach: 1) matching of image correspondences, and 2) 3D reconstruction based on the geometry of stereo cameras (FIG. 12B).

Previously, image matching has been described with respect to explicit image synthesis, such as a full image synthesis or a geometry-only image synthesis. However, image matching may be made using implicit image synthesis. That is, images are not actually synthesized. Rather, a computer aided design (CAD) model of the tools and prior pose information of the tools are implicitly used to facilitate image matching.

Moreover, artificial markers may be applied to the tools to assist in image matching as is described below. However, natural markers or features of a tool may be used to assist in image matching. Thus, the following descriptions apply equally well to the case when no artificial markers are present and features of the tool, i.e., natural markers, are detected directly from the instrument images.

Figure 5B:
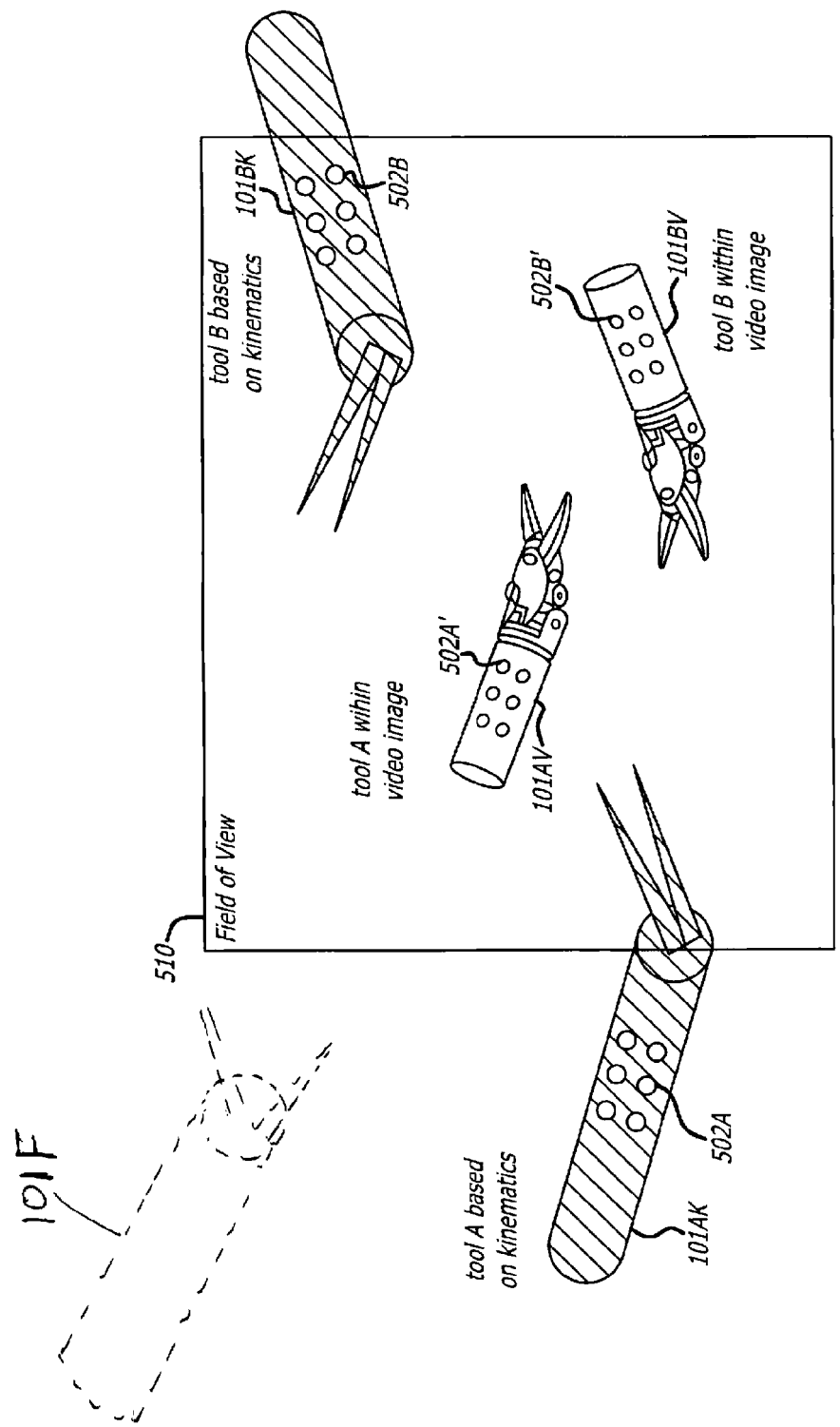
FIG. 5B illustrates different tool positions of a pair of tools in the field of view of a camera based on kenematic information and video image information.

Referring now to FIG. 5B, image matching can be significantly simplified yet made robust by exploring prior knowledge and available robotic kinematics even in the presence of more than one robotic instrument in the field of view. FIG. 5B illustrates video images 101AV and 101BV for a respective pair of tools 101A and 101B in the field of view 510. FIG. 5B further illustrates pose information 101AK and 101BK based on kinematics for the respective tools 101A and 101B in and around the field of view 510. The video images 101AV and 101BV and the pose information 101AK and 101BK for the respective tools 101A and 101B may be adaptively fused together to improve the overall pose information for each. A plurality of marker dots 502A and 502B or other types of markers, may be affixed to the respective tools 101A and 101B. Video information of the marker dots 502A' and 502B' may be ascertained from the video images 101AV and 101BV of the respective tools 101A and 101B.

For simplicity in explanation, it is assumed that image feature points (maker dots 502A'-502B') are reliably localized, and without loss of generality, it is further assumed that the image feature points form a pattern. Using the concept of a pattern, the image matching problem is simplified from many dot-to-dot matchings to a single pattern matching. A pattern matching or association is straightforward if one tool is in the field of view. If more that one robotic instrument tool is in the field of view, there are two approaches available to solving the image matching problem that can be used alone or combined together.

In one embodiment of the invention, it is assumed that the robotic kinematics information will not change the spatial arrangements (positional and/or orientational) across instruments, especially in the beginning of surgical operations. For example, if two instruments are arranged to the left and to the right in the camera coordinate system, then the robotic kinematics should represent that arrangement. However, this is not a requirement on the absolute values of the robotic kinematics information. For example, the robotic kinematics information may indicate that the one or both of the robotic surgical tools are outside the field of view. Resolving pattern association ambiguity in matching a first pattern in an image to the tool arranged to the left and a second pattern in the image to the tool arranged to the right can be carried out in either 2D image or 3D space.

In another embodiment of the invention, tool motion is used to resolve the pattern association ambiguity. As the plurality of tools move differently (e.g., different directions and/or speed), pattern images are tracked individually through temporal image matching. The motion trajectories of the pattern images are then compared against the kinematic information of each of the tools. From the comparison, the correct association of pattern images to tools can then be made.

There may be a pattern association issue for a single tool in the field of view. A pattern may be directionally ambiguous, such as a line pattern with identical markers that has a directional ambiguity of a 180-degree flip. Pattern association for a single tool is not an issue if the pattern consisting of artificial markers or natural markers is unique. For example, if the pattern of markers has directional information embedded such that the markers at each of ends of the pattern are distinctive there is no issue. In one embodiment of the invention, the design of the artificial markers on the tool provides directional information of the marker pattern.

If there is a directional ambiguity for a given tool, there are two approaches to solving the image matching problem, similar to how the pattern associations for multiple tools is handled. The first approach to solving the image matching problem is to use very rough robotic kinematics information to resolve any directional ambiguity. The robotic kinematics should not flip although it may be far away, such as outside the field of view after projection onto 2D image. The second approach to solving the image matching problem is to use motion trajectories of the pattern to remove the directional ambiguity.

View-Geometry Statistics for Adaptive Fusion

Image information may have quality issues (matching reliability and accuracy) regarding image-derived 3D information. For example, a viewing-singularity happens when a cylindrical instrument with markers on the shaft is projected to an image of small circle (see 1222S in FIG. 12A). That is, all the markers become invisible, hence there is no vision-based observation. Another extreme case for perfect viewing is when the instrument shaft lies right in the field of view so that all the markers are fully visible. That is, a circular marker is projected onto image as a circle for example. In practice, we often have scenarios between these extreme cases.

Viewing geometry is more than just pure geometry between a camera and a 3D object. Other information related to viewing geometry can impact the quality of image-derived information for fusion.

Referring now to FIG. 12A, the geometry of an illumination source 1210A-1210B with respect to the camera 1211A-1211B and the 3D object may be of interest to achieve accurate and reliable information. The position of light source 1210A with respect to the camera 1211A and the 3D object 1200 generating view 1 may differ from the position of light source 1210B with respect to the camera 1211B and the 3D object 1200 generating view 2. Moreover, the different poses of the 3D object may change how a light source strikes its features and provide different views.

Additionally, different parts of a 3D object may behave differently under the same or different viewing conditions. For example, the tip 1200T and the shaft 1200S of a 3D tool 1200 may generate different image-derived 3D information with different reliabilities. In image 1221A the shaft image 1221S may be good to use while in image 1221B the shaft image 1222S may be poor to use in forming image-derived 3D information.

The quality of image-derived 3D information also depends upon the particular image features used. For example, edge-based features are less sensitive to illumination change than intensity-based features.

These issues with regard to viewing geometry contribute toward how vision information should be generated and combined with robot kinematics for fused results that are reliable and accurate. The quality of viewing geometry may be described statistically. View-geometry statistics are used to represent how good the image-derived information for fusion is when compared to the ground-truth. That is, view-geometry statistics may be used to estimate uncertainty. The view-geometry statistics are used in the Bayesian state-space model for adaptively fusing image information and kinematics information. To be specific, the view geometry statistics may be represented in the covariance matrix of the observation equation (Eq. 13).

The following may be considered for view-geometry statistics: Digitization error/image resolution; feature/algorithm related Image matching error; Distance from object to camera; Angle between object surface normal and line of sight; Illumination and specularity. Based on certain noise assumptions (e.g., independent Gaussian noise), view-geometry statistics for these phenomenon may be computed. To make a specific example, we assume the case of parallel stereo images (FIG. 12B) were 3D points are first reconstructed and then fed into the state space. Under this ideal assumption, we have $y^r = y^l$. And the x-directional image projection are $$x^r = f_x \frac{X^s - 1/2 B_s}{Z_s} \text{ and } x^l = f_x \frac{X^s + 1/2 B_s}{Z_s},$$

where $B_s$ is the baseline distance between the two optical centers and $f_x$ is the common focal length in x-direction. Finally, the 3D reconstruction problem becomes a simple one with a parallel setup as follows:

$$\begin{cases} X_s = \frac{1}{2} B_s \left( \frac{x^l + x^r}{x^l - x^r} \right) \\ Y_s = \frac{1}{2} B_s \left( \frac{f_y}{f_x} \right) \left( \frac{y^l + y^r}{x^l - x^r} \right) \\ Z_s = B_s \left( \frac{f_x}{x^l - x^r} \right) \end{cases} \quad \text{(Eq. 14)}$$

For presentation simplicity, we use $d_x = x^l - x^r$ to represent the image disparity for the matched left and right image point.

In the following, we list equations and plots based on the assumption of independent Gaussian noise and the parallel stereo setup (Eq. 14). Assuming that we have image matching uncertainty $\sigma_x$, we can derive the following equation $$\text{Var}\{X_s\} \approx \overline{X}_s^2 \left[ \frac{\sigma_x^2}{\overline{d}_x^2} - \frac{\sigma_x^4}{\overline{d}_x^4} \right] \approx \overline{X}_s^4 \frac{\sigma_x^2}{B_s^2 f_x^2} \quad \text{(Eq. 15)}$$

$$\text{Var}\{Y_s\} \approx \overline{Y}_s^2 \left[ \frac{\sigma_x^2}{\overline{d}_x^2} - \frac{\sigma_x^4}{\overline{d}_x^4} \right] \approx \overline{Y}_s^4 \frac{\sigma_x^2}{B_s^2 f_x^2}$$

$$\text{Var}\{Z_s\} \approx \overline{Z}_s^2 \left[ \frac{\sigma_x^2}{\overline{d}_x^2} - \frac{\sigma_x^4}{\overline{d}_x^4} \right] \approx \overline{Z}_s^4 \frac{\sigma_x^2}{B_s^2 f_x^2}$$

where symbols with a bar (e.g., $\overline{Z}_s$, $\overline{d}_x$) represent the true values.

From this and the plots based on simulation of exact camera model, we can conclude that the uncertainty (standard deviations) of the X/Y/Z estimate of a 3D point is proportional to the uncertainty of image matching, the inverse of image resolution, and the square of the true value of X/Y/Z. The plot in FIG. 12E is based on simulation of exact model and Gaussian random matching error to confirm the conclusion that the estimate uncertainty of a 3D point is proportional to the uncertainty of image matching.

The plot in FIG. 12C is based on simulation of image digitization error [−0.5, 0.5] pixel and correct image matching to confirm the conclusion that the estimate uncertainty of a 3D point is proportional to the inverse of image resolution. The plot in FIG. 12D is based on simulation of varying depth to confirm the conclusion that the estimate uncertainty of a 3D point is proportional to the square of the true value of X/Y/Z:

View-geometry statistical analysis can also be applied to the most general case of camera set up, for example, a non-parallel set up. It can also be applied to the case of using 2D images rather than 3D stereo-reconstructed points as observations. In the following, we give a simple example. More specifically, let's apply the following projective equations $$x_i = \psi(K[R_C|-C]X_i),$$ (Eq. 16)

for both left and right cameras. $\psi$ is the perspective projection (Eq. 1A) and K is the 3×3 camera intrinsic parameter matrix, while $R_C$ (3×3) and C (3×1) represent the camera orientation and position, the extrinsic parameters. Overall, we can use a 3×4 matrix A to represent $K[R_C|-C]$. For left camera and right camera, we use $A^l$ and $A^r$ respectively. Hence the stereo problem becomes solving the following array of equations:

$$x_i^l = \psi(A^l X_i),$$

$$x_i^r = \psi(A^r X_i),$$ (Eq. 17)

We can linearize this array of equations to be the following with B being the 2×3 Jacobian matrix and x being the mean-subtracted variable as follows;

$$\tilde{x}_i^l \approx B^l X_i,$$

$$\tilde{x}_i^r \approx B^r X_i,$$ (Eq. 18)

From Eq. 18, we can compute the Jacobian matrix required for computing the observation covariance matrix for EKF in the case of using 2D images as observations as follows:

$$J_i = \begin{bmatrix} B^l \\ B^r \end{bmatrix}^+$$

where [ ]$^+$ represents a pseudo inverse.

Sequence Matching by Exploring Kinematics Constraints

Referring now to FIGS. 13A-13B, the concept of sequence matching is now described. A technique is chosen for matching a pair of image features 1301 and 1302 such as from left and right images respectively in a stereo setting or a real image and a synthesized image. The pair of images features may be matched over one or more sequences of images 1301A-1301E and 1302A-1302E, for example.

A rigid sequence matching (where the relative kinematics within each sequence are perfectly known or identical across sequences in the ideal case) may be employed where just one common motion parameter is used to estimate for all pairs between two sequences such as illustrated in FIG. 13A. The sequences 1301 and 1302 have identical motion relationship (relative kinematics) among the images 1301A to 1301E, and 1302A to 1302E. Alternatively, a flexible sequence matching (where the relative kinematics within each sequence are known with errors) may be employed as illustrated in FIG. 13B. The sequences 1303 and 1302 have a identical motion relationship (relative kinematics) among the images 1303A to 1303E, and 1302A to 1302E.

To match a single pair of features 1301C and 1302C in a single pair images of a sequence, there may be only a 60% chance or probability of matching the pair of image features correctly, for example. This may be an acceptable for a number of applications but typically would be unacceptable for medical or surgical applications. The probability of matching the image features should be much higher for medical and surgical applications that demand high accuracy.

If two or more two temporal sequences 1301A-1301E and 1302A-1302E of images are available for matching and the kinematics among images within each sequence is known or identical across sequences, the probability of matching image features can be improved over that of a single pair of images. Assuming statistical independence and that the chance or probability of matching a single pair of image features correctly is 60% the chance of having correct matching improves to 78% with a sequence of 3 images, 92% with a sequence of 5 images, and 99% with a sequence of just 10 images, for example. However, if the relative kinematics for each pair of images in the sequence is not accurate, the chance of having correct matches is less and a bundle adjustment procedure should be taken for improved matching. Within the bundle adjustment procedure, the relative kinematics and its uncertainty are taken into consideration.

In one example of applying sequence matching where there are two sequences of observations (e.g., image feature points) $O_1 = \{F_{1,1}, \ldots, F_{1,n}\}$ and $O_2 = \{F_{2,1}, \ldots, F_{2,n}\}$, the problem is to find out the geometric transform $T_s$ between the two sequences through sequence matching. In matching individual pairs $F_{1,i}$ and $F_{2,1}$, a geometric transform $T_{s,i}: F_{1,i} \to F_{2,i}$ may be computed. In other words, we have the following equation for individual matching $$T_{s,i}^* = \underset{T_{s,i}}{\arg\min} C\{F_{1,i}(T_{s,i}(X)), F_{2,i}(X)\}$$ (Eq. 19)

where C is the cost function of matching features $F_{1,i}$ and $F_{2,i}$ and X represents the location of the features in either two or three dimensions. For example, the geometric transformation $T_{s,i}$ may be in 3D and the features may be in 2D after known camera projection. If relative kinematics $\dot{k}_{1/2,i}$ within each sequence are perfectly known, then the geometric transformation equation for sequence matching may become $$T_s^* = \underset{T_s}{\arg\min} C\Big\{ F_{1,1}(T_s^{k_{1,1}}(X)),$$ (Eq. 20)

$$F_{2,1}(\dot{k}_{2,1}(X)); \ldots; F_{1,n}(T_s^{k_{1,n}}(X)), F_{2,n}(\dot{k}_{2,n}(X)) \Big\}$$

where $T_s^{k_{1,1}}$ represents transformation from $T_s$, typically a chosen $T_{s,i}$, through relative known kinematics.

In the geometric transformation (Eq. 20), the same amount of available information is used to estimate just one parameter $T_s$ as it is to estimate a series of parameters $T_{s,j}$ (Eq. 19). Consequently, the use of sequence of images and relative kinematics provides a result that is much more accurate and robust. Sequence matching is more accurate and robust with as many diverse images in the sequence as possible. If the sequence of images are all the same, then the assumption of statistical independence per matching is false. As a result, the matching performance with a sequence of images will not be improved. For example, in the tool acquisition operational stage 604 illustrated in FIG. 6A, diversified images sequences may be generated by translating and/or rotating the tools within the field of view of the camera.

Sequence matching methods may be applied in many different scenarios, e.g., a single view case (a sequence of real images against a sequence of synthesized images) or a stereo case (matching among two sequences of real images and two sequence of synthesized images). However, relative kinematics may not be perfect and may change over time. Hence, bundle adjustment based flexible sequence matching may be applied to estimate the optimal parameters to more accurately locate and track tools.

Tool Tracking for Image Guided Surgery

A tool tracking system for a robotic instrument has a number of applications. One application for a tool tracking system is image-guided surgery (IGS), or more specifically image-guided endoscopic surgery (IGES). The basic goal of image guided surgery is to enhance a surgeon's experience by providing real time information derived from single or multiple imaging modalities (e.g., visual, x-ray, computerized topography (CT), magnetic resonance imaging (MRI), ultrasound) during surgery or training/simulation. Two particular benefits of IGS/IGES are 1) improved visualization for easier on-line diagnostics and 2) improved localization for reliable and precise surgery. Tool tracking is one technology used for IGS/IGES since instruments are used by surgeons to navigate, sense and operate (e.g., diagnostic, cut, suture, ablation etc.) in the areas of interest. That is, the tool tracking system described herein can enable image-guided surgery without significant added operational inconvenience and/or added equipment. The tool tracking system described herein may also be used in other applications, such as dynamically reconstructing the geometry of organs, surgical simulation, and training.

Tool tracking may be used to provide automated camera control and guidance to maintain a robotic instrument in the field of view. Tool tracking can also be used to assist the surgeon to move the robotic instrument to reach a tumor either automatically or with a surgeon's assistance. Ultra-sound or pre-scanned images can also be used along with real-time tool tracking. Other applications of tool tracking include graphic user interface that facilities the entrance and re-entrance of the robotic instrument during surgery.

Tool tracking can be used to take a number of measurements during surgery as well. For example, tool tracking may be used to measure organ sizes by touching the robotic tool tip at different points of an organ. A pair of robotic tools being tracked can concurrent touch points of the organ and a distance along a line between their tips can be accurately measured with the assistance of tool tracking. Additionally, tool tracking may be used to construct a 3D model of an organ. The tip of a single robotic tool may be used to touch points across the organ's surface to construct a 3D model of the organ.

Tool tracking can be used to align different image modalities together. Referring now to FIG. 17, a perspective view of a surgical site 1700 includes a robotic ultrasound tool 1710. The robotic ultrasound (US) tool 1710 has an attached or integrated ultrasound transducer 1710A. The robotic ultrasound (US) tool 1710 may be used to guide and navigate other instruments to perform various medical or surgical procedures. By touching tissue 1705 in the surgical site with the robotic ultrasound tool 1710, two dimensional ultrasound images 1711A may be captured in a two dimensional coordinate system 1703. The two dimensional ultrasound images 1711A may be translated from the two dimensional coordinate system 1703 into a camera coordinate system 1701. The translated ultrasound images may then be overlaid onto video images of the surgical site 1700 displayed by the stereo viewer 312, such as illustrated by the translated ultrasound images 1711B-1711D in the surgical site 1700 illustrated in FIG. 17. Tool tracking may be used to flagpole ultrasound by (1) determining the transformation of the ultrasound images 1711A from the two dimensional coordinate system 1703 to the local ultrasound coordinate system 1702 in response to ultrasound calibration; (2) at the transducer 1710A, determining the transformation from the ultrasound transducer coordinate system 1702 to the camera coordinate system 1701 by using tool tracking; and then; (3) cascading the transformations together to overlay the ultrasound image in the camera coordinate system 1701 onto the surgical site as illustrated by image 1711B. The quality of image overlaying depends on tracking accuracy of the robotic ultrasound tool within a camera coordinate system (FIG. 5A) and the ultrasound calibration. Ultrasound calibration is described in the reference "A novel closed form solution for ultrasound calibration," Boctor, E.; Viswanathan, A.; Choti, M.; Taylor, R. H.; Fichtinger, G.; Hager, G., Biomedical Imaging: Nano to Macro, 2004. IEEE International Symposium on Volume, Issue, 15-18 Apr. 2004 Page(s): 527-530 Vol. 1. Tool tracking may also be used to generate 3D/volumetric ultrasound images by stacking overlaid 2D images 1711B-D from the 2D ultrasound transducer 1710A generated by rotating the ultrasound tool 1701 as illustrated by the arrow 1720.

As shown in FIG. 16, tool tracking may be used overlay one or more drop virtual point/marks 1650A-1650B on images of the tissue surface 1600 in the surgical site by using one or multiple tools 1610L, 1610R (for example, a surgical tool or an ultrasound tool) to touch point of interest. For example, in telestration operation, teaching surgeons can use tools to draw virtual marks to illustrate areas of interest to remote student surgeons on an external display. Another example is that surgeon can use one type of tracked tool (e.g., an ultrasound tool) to draw marks to indicate regions of interest and then use a different type of tracked tool (e.g., a cautery tool) to operate or perform a surgical or other medical procedure in selected regions of interest.

The tool tracking system described herein may also be used for image-guided interventional radiology (IGIR) along with other sensors. For example, active sensors/cameras (e.g. electro-magnetic sensor, or active near Infra-Red illumination plus stereo camera) may be used to scan patient bodies for navigation or 3D reconstruction with tool tracking during surgery.

Referring now to FIG. 15, a flow chart 1500 of an IGS application with tool tracking is illustrated. The flow chart 1500 illustrates a robotic surgery for a tumor in or around a liver. However, IGS with tool tracking may be used for other medical and surgical procedures for different organs and tissue that are robotically controlled or robotically assisted.

At block 1501A, a liver or other organ/tissue prior to surgery may be scanned with a computer tomography scanner 1503 to obtain a number of images of the liver such that they may be used to reconstruct a complete 3D volume of a scanned object at block 1504 by a computer as desired. There may be a slight computer tomography error ECT for 3D reconstruction that may be minimized.

At block 1505, a computer tomography volume that includes liver and surrounding area is selected to generate a computer tomographic (CT) segment that contains liver only. At this point, the CT volume segment is taken to register against a surface/depth map from other imaging modalities, e.g., stereo cameras.

The real liver during surgery 1501B may have some biological variation forming an error (EBIO) from the prior scan taken by the CT scanner.

One or more robotic instrument tips 1510 are inserted into the surgical site.

One or more endoscopic cameras 1512 take sequences of images 1513-1514 of the surgical site including the liver 1501B and the robotic instrument tips 1501. These sequences of images 1513-1514 are typically stereo image pairs but could be a sequence of single images from a mono-view. The sequence of images 1513 may be used to determine the depth of surface features to make a surface/depth map 1515. In one embodiment of the invention, a sequence of surface maps 1515 including a robotic instrument may be analyzed similar to a sequence of images 1513 as described herein to determine a location of the robotic instrument.

The surface map 1515 may be overlaid with a model of an organ after surface registration. The surface map 1515 may be further annotated with a map, outline, or other indication of the estimated tumor location 1517. For example an internal liver tumor that is not visually visible maybe easily visible in a CT scan of the liver. An error between the estimated tumor location and the actual tumor location during surgery may be a sum of errors of the scanning (Ect), surface registration (Ereg), biological changes (Ebio), and formation of the depth/surface map (Est). This error can be reduced with further information from tool tracking and touching a tool tip to the tissue.

The sequences of images 1514 may be stereo image pairs or a sequence of single images from a mono-view. The sequence of images 1514 along with kinematics information may be adaptively fused together to translate a model of the tool tip (MET) into the endoscopic camera frame of reference (ECM). The model of the tool tip formed from the adaptive fusion based tool tracking may be used to estimate the tool tip location 1518. An estimation error ($E_{ET}$) between the actual tip location 1520 and the estimated tip location 1518 may be made small by the tool tracking methods described herein. By using the tumor location 1550 and tool tip location 1520 during surgery, we can drive the tools to touch their tips to reach the tumor, one example of image-guided surgery. One or more of the robotic surgical tools may include a needle at its tip as the end effector. The operational error $E_{OP}$ between the actual location of the tumor and the actual location of tool tips is a sum of errors.

Referring now to FIG. 16, a perspective view of a surgical site to provide image guided surgery is illustrated. A pre-scanned image 1602A (for example, CT images) may be aligned to a camera coordinate system 1605 and then overlaid as an overlaid image 1602B onto a surface map or depth map 1600 of the tissue surface.

Visual information and kinematics information of the first robotic instrument 1610L and the second robotic instrument 1610R may be adaptively fused together to more accurately determine the position of the tools within the surgical site. With both position of the overlaid image 1602B and the tools 1610L,1610R aligned to the camera coordinate system 1605, the tool may be automatically or manually guided to perform a procedure on the tissue. The overlaid image 1602B may represent a tumor on the tissue surface or buried below the tissue surface that would otherwise be hidden from view. As portions of the tool 1610L or 1610R are moved below the tissue surface so that it is occluded, an image 1610B of the portion of the tool below the surface may be synthesized in response to the tool tracking information and the adaptive fusion of kinematics with a priori video information of the tool.

The one or more robotic surgical tools 1610L and 1610R may be used to take measurements or determine a surface profile. Tissue in a surgical site may be touched with the tool tip of the robotic tool 1610L at a first point and tissue in the surgical site may be touched with the tool tip of the robotic tool 1610R at a second point. A sequence of images of the surgical site including the robotic surgical tools 1610L and 1610R may be captured. Kinematics information and image information of the robotic tools may be adaptively fused together to accurately determine the tool tip locations at the first and second points. The pose of the first tool tip at the first point and the pose of the second tool tip at the second point may be compared to determine a distance between them. The tool tips may be touching external surfaces of a tumor to determine a diameter of the tumor. Alternatively, the tool tips may be touching external surfaces of an organ to measure the diameter of the organ.

Within the presented framework for adaptive fusion of vision and kinematics for tool tracking, we can also incorporate the depth maps.

In one embodiment of the invention, we use depth maps for localizing tools. A sequence of depth maps including a robotic instrument may be analyzed to determine a location of robotic instruments. Robotic instruments can be located in the camera coordinate frame using any depth map in which the tool can be identified. Kinematics datum provides an approximate location for a robotic instrument that is to be tracked. This is a priori knowledge for the next iteration of the tracking problem. The depth map is analyzed in the environs of the approximate location to locate the robotic instrument. Other information may be employed to improve the a priori knowledge, such as a dynamic model of the robotic instrument, or knowledge of the type of procedure being performed under the camera capturing the images. The locating of the robotic instrument may be performed over any number of depth maps.

If a correlation exists between sequential views, the problem of sequential location of a target robotic surgical tool is a tool tracking problem. The depth maps may be sequential views, arranged in time order, in which case there is a correlation between the successive views.

Kinematics datum provides an approximate location for a robotic instrument that is to be tracked. This is a priori knowledge for the next iteration of the tracking problem. The depth map is analyzed in the environs of the approximate location to locate the robotic instrument. Other information may be employed to improve the a priori knowledge, such as a dynamic model of the robotic instrument, or knowledge of the type of procedure being performed under the camera capturing the images. If the robotic tool is obscured, a current optimal estimate of the location of the surgical instrument may be made (an a posteriori estimate) using the a priori knowledge and the depth map. Instantaneous (re-)correction of the kinematics datum may be computed by adaptively fusing together the available kinematics data, visual information, and/or a priori information. The correction to the current state is used to update the ongoing correction of future kinematics data. In one embodiment of the invention, the correction is simply made to future data without regard for past corrections. In another embodiment of the invention, the sequence of corrections is analyzed and an optimal correction based on all available past corrections is computed and used to correct the kinematics data. Analysis by synthesis and appearance learning techniques may be used to improve the correction to the current state.

Algorithms that locate the surgical instrument in the depth map and provide the optimal kinematic correction, can be further optimized by understanding of the relative variances in corrected kinematic residual error vs. the variances in computed robotic instrument location from the depth map. Kinematics is suspected of initially having a large DC bias, but relatively small variance. A well-design image processing sub-system may have substantially zero DC bias but a relatively large variance. An example of an optimal correction that accommodates these two differing noise processes is one generated by a Kalman filter.

Tool Tracking User Interface

Previously described herein with reference to FIG. 16, if portions of the tool 1610L or 1610R are moved below the tissue surface so that it is occluded, an image 1610B of the portion of the tool below the surface may be synthesized. The synthesized image portion 1610B may be included in the tool images 400L,400R as synthesized image portion 400B displayed on the display devices 402L,402R of the stereo viewer 312 illustrated in FIG. 4.

Referring now to FIG. 5B, while tracking a robotic surgical tool, it may exit the field of view 510 of a camera entirely such, as illustrated by the tool 101F. The robotic surgical tool may no longer be in the field of view as a result of camera movement over the surgical site, robotic surgical tool movement, or a combination of both. For example, the camera may move away from the position of the robotic surgical tool in a surgical site such that the robotic surgical tool is outside the field of view of the camera. As another example, the robotic surgical tool may move away from a position of the camera in a surgical site such that the robotic surgical tool is outside the field of view of the camera. In either case, a surgeon may be left guessing where the robotic surgical tool is outside the field of view unless some indication is provided to him in the stereo viewer 312.

In FIG. 4, compass icons or a compass rose (generally referred to with reference number 420) may be displayed in the display devices of the stereo viewer 312 to provide an indication where the robotic surgical tool is located outside the field of view and a direction of tool reentrance into the field of view. For example one of a plurality of compass icons for the directions North 420N, South 420S, East 420E, and West 420W as well as directions in between such as North-East 420NE, North-West 420NW, South-East 420SE, and South-West 420SW may be indicated in the stereo viewer to indicate tool reentrance into the field of view of the camera over a surgical site.

To indicate tool reentrance into the field of view a robotic surgical tool is tracked in and out of the field of view of the camera. A determination is made by comparing positions of the camera and a tool whether or not it is outside the field of view of the camera by using the available tool tracking information of the robotic surgical tool. It the robotic surgical tool is out of the field of view, then one of a plurality of compass icons 420 may be displayed in the field of view to show a direction of tool reentrance.

Additional information, such as getting closer or farther in distance away from the field of view, may be conveyed to a surgeon looking in the stereo viewer 312 by somewhat altering the one compass icon 420 in the display that indicates the direction of the tool. For example, by flashing the icon fast or slow may indicate the robotic surgical tool is getting closer or farther away respectively from the field of view. As another example, arrowheads may be added to ends of a bar icon to indicate that the robotic surgical tool is move towards or away from the field of view. In an alternate implementation, the icon indicating direction or re-entrance may be colored to indicate movement bringing the tool closer to the field of view (e.g., red for getting warmer) or movement taking the tool further away from the field of view (e.g., green for getting colder).

CONCLUSION

The embodiments of the tool tracking system described herein provide an automatic integrated system that is accurate and reliable by adaptively fusing kinematics and visual information, synthesizing images based on a model and prior poses, and employing sequence matching.

A number of elements of the tool tracking system are implemented in software and executed by a computer and its processor, such as computer 151 and its processor 302. When implemented in software, the elements of the embodiments of the invention are essentially the code segments to perform the necessary tasks. The program or code segments can be stored in a processor readable medium or transmitted by a computer data signal embodied in a carrier wave over a transmission medium or communication link. The processor readable medium may include any medium that can store or transfer information. Examples of the processor readable medium include an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The computer data signal may include any signal that can propagate over a transmission medium such as electronic network channels, optical fibers, air, electromagnetic, RF links, etc. The code segments may be downloaded via computer networks such as the Internet, Intranet, etc.

While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, some embodiments of the invention have been described with reference to a robotic surgical system. However, these embodiments are equally applicable to other robotic systems. Thus, the embodiments of the invention should be construed according to the claims that follow below.

What is claimed is:

1. A method to locate a robotic instrument in a field of view of a camera, the method comprising:
   capturing sequential images in a field of view of a camera, the sequential images being correlated between successive views;
   receiving a kinematic datum to provide an approximate location of the robotic instrument; and
   analyzing the sequential images in response to the approximate location of the robotic instrument.

2. The method of claim 1, further comprising:
   locating the robotic instrument in the field of view in response to the analysis of the sequential images.

3. The method of claim 1, further comprising:
   estimating a current location of the robotic instrument in the field of view in response to the analysis of the sequential images and a portion of the robotic instrument being hidden from the field of view.

4. The method of claim 1, further comprising:
   synthesizing a model of the robotic instrument; and
   further analyzing the sequential images in response to the model of the robotic instrument.

5. The method of claim 1, wherein
   the kinematic datum is a current kinematic datum, and the method further comprises correcting the current kinematic datum to correct future kinematic datum without regard to corrections of past kinematic datum.

6. The method of claim 1, wherein
the kinematic datum is a current kinematic datum, and the method further comprises
correcting the current kinematic datum in response to corrections of past kinematic datum such that future kinematic datum can be corrected.

7. The method of claim 1, wherein
the sequential images form a depth map, and
the depth map is analyzed in response to the approximate location of the robotic instrument to locate the robotic instrument in the field of view.

8. A method for robotic systems, the method comprising:
receiving one or more video images of at least one robotic instrument in reference to a camera coordinate system;
receiving kinematics information associated with the at least one robotic instrument; and
localizing the at least one robotic instrument in the camera coordinate system in response to the one or more video images and the kinematics information.

9. The method of claim 8, wherein
the localizing of the at least one robotic instrument includes
predicting the position of the at least one robotic instrument in response to the kinematics information.

10. The method of claim 9, wherein
the localizing of the at least one robotic instrument includes
synthesizing an image of the at least one robotic instrument in response to a computer aided design (CAD) model of the at least one robotic instrument; and
analyzing the video images to match the synthesized tool image to an actual tool image to determine a position of the robotic instrument.

11. The method of claim 10, wherein
the analyzing to determine the position includes
minimizing a cost function of comparing the synthesized tool image with the actual tool image, and
minimizing a sum of squared differences between geometries of the synthesized tool image and the actual tool image.

12. The method of claim 11, wherein
the minimizing of the sum of squared differences includes
non-linearly mapping a three dimensional synthesized tool image into a two dimensional synthesized tool image.

13. The method of claim 12, further comprising:
learning a change in appearance of the at least one robotic instrument in response to a different view of the at least one robotic instrument.

14. The method of claim 13, wherein
the change in appearance includes a change in one or more of lighting, occlusion, wear, and the surrounding environment of the robotic instrument.

15. The method of claim 8, further comprising:
after localizing the at least one robotic instrument,
tracking the motion of the at least one robotic instrument in the camera coordinate system in response to the one or more video images and the kinematics information.

16. The method of claim 15, wherein
if while tracking the motion the at least one instrument is occluded so as to become untrackable, then
the localizing of the at least one robotic instrument in the camera coordinate system is repeated to locate the robotic instrument in the camera coordinate system.

17. The method of claim 15, wherein
the tracking of the motion of the at least one robotic instrument includes
adaptively fusing the video images and the kinematics information together to determine a position of the at least one robotic instrument.

18. The method of claim 17, wherein
the adaptively fusing includes
weighting the kinematics information more than the video images if the video images are unreliable indicators of a location of the at least one robotic instrument.

19. The method of claim 17, wherein
the adaptively fusing includes
weighting the video images more than kinematics information if the kinematics information are unreliable indicators of a location of the at least one robotic instrument.

20. The method of claim 17, wherein
the adaptively fusing includes
weighting the video images more than kinematics information if the video images are reliable indicators of a location of the at least one robotic instrument.

21. The method of claim 17, wherein
the adaptively fusing includes
using a covariance matrix with a state space model to adaptively fuse the video images and kinematics information together to provide a reliable indicator of a location of the at least one robotic instrument.

22. A method for indicating tool entrance into a field of view of a camera, the method comprising:
tracking a robotic surgical tool in and out of a field of view of a camera;
determining that the robotic surgical tool is outside the field of view of the camera in response to the tracking of the robotic surgical tool; and
displaying one of a plurality of compass icons in a display of the field of view to indicate a direction of tool reentrance into the field of view.

23. The method of claim 22, further comprising:
altering the one compass icon in the display by flashing, adding arrowheads, or changing color to indicate an increase and a decrease in a distance between an edge of the field of view of the camera and the robotic surgical tool.

24. The method of claim 22, wherein
the camera has moved away from the position of the robotic surgical tool in a surgical site such that the robotic surgical tool is outside the field of view of the camera.

25. The method of claim 22, wherein
the robotic surgical tool has moved away from a position of the camera in a surgical site such that the robotic surgical tool is outside the field of view of the camera.

* * * * *